(12) United States Patent
Marcin et al.

(10) Patent No.: US 9,738,642 B2
(45) Date of Patent: Aug. 22, 2017

(54) TRIAZOLOPYRIDINE ETHER DERIVATIVES AND THEIR USE IN NEUROLOGICAL AND PYSCHIATRIC DISORDERS

(71) Applicant: BRISTOL-MYERS SQUIBB COMPANY, Princeton, NJ (US)

(72) Inventors: Lawrence R. Marcin, Bethany, CT (US); Mendi A. Higgins, Meriden, CT (US); Joanne J. Bronson, Durham, CT (US); F. Christopher Zusi, Hamden, CT (US); John E. Macor, Washington Crossing, PA (US); Min Ding, Glastonbury, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/022,072

(22) PCT Filed: Sep. 18, 2014

(86) PCT No.: PCT/US2014/056273
§ 371 (c)(1),
(2) Date: Mar. 15, 2016

(87) PCT Pub. No.: WO2015/042243
PCT Pub. Date: Mar. 26, 2015

(65) Prior Publication Data
US 2016/0237081 A1 Aug. 18, 2016

Related U.S. Application Data

(60) Provisional application No. 61/879,925, filed on Sep. 19, 2013.

(51) Int. Cl.
C07D 471/04 (2006.01)
A61K 31/437 (2006.01)
C07B 59/00 (2006.01)

(52) U.S. Cl.
CPC .......... *C07D 471/04* (2013.01); *C07B 59/002* (2013.01); *C07B 2200/05* (2013.01)

(58) Field of Classification Search
None
See application file for complete search history.

(56) References Cited

U.S. PATENT DOCUMENTS

| 7,572,807 B2 | 8/2009 | Li et al. |
| 8,765,767 B2 | 7/2014 | Mattson et al. |
| 2006/0281750 A1* | 12/2006 | Li ........................ C07D 471/04 514/248 |
| 2015/0152113 A1 | 6/2015 | Mattson et al. |

FOREIGN PATENT DOCUMENTS

| WO | WO 2010/130423 A1 | 11/2010 |
| WO | WO 2012/062750 A1 | 5/2012 |
| WO | WO 2012/062752 A1 | 5/2012 |

* cited by examiner

*Primary Examiner* — Alicia L Otton
(74) *Attorney, Agent, or Firm* — James Epperson

(57) ABSTRACT

The disclosure generally relates to compounds of formula I, including their salts, as well as compositions and methods of using the compounds. The compounds modulate the mGluR2 receptor and may be useful for the treatment of various disorders of the central nervous system.

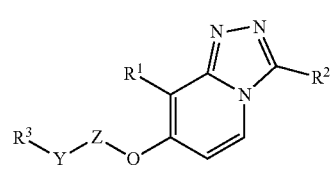

(I)

11 Claims, No Drawings

US 9,738,642 B2

TRIAZOLOPYRIDINE ETHER DERIVATIVES AND THEIR USE IN NEUROLOGICAL AND PYSCHIATRIC DISORDERS

CROSS-REFERENCE TO RELATED APPLICATIONS

This application claims priority to Provisional Patent Application U.S. Ser. No. 61/879,925 filed Sep. 19, 2013, hereby incorporated by reference in its entirety.

BACKGROUND OF THE INVENTION

The disclosure generally relates to compounds of formula I, including their salts, as well as compositions and methods of using the compounds. The compounds are ligands, agonists, or partial agonists for the mGluR2 PAM receptor and may be useful for the treatment of various disorders of the central nervous system.

Glutamate is the major excitatory neurotransmitter in the mammalian brain, playing an important physiological role in a wide variety of processes. Glutamatergic neurotransmission is predominantly mediated through activation of cell surface receptors including ligand-gated ion channels (ionotropic receptors) and metabotropic glutamate G protein coupled receptors (mGluRs). The metabotropic glutamate receptor family is comprised of 8 family members that are part of the family 3 GPCR superfamily. These receptors are further subdivided into Group I (mGluR 1, 5), Group II (mGluR 2, 3) and Group III (mGluR 4, 6, 7, 8) based upon sequence homology, receptor signaling, and pharmacology.

At the cellular level, mGluR2 plays a key role as an autoreceptor in glutamate terminals, though it is generally thought to be localized at the periphery of the synapse, away from the active zone. Activation of the mGluR2 receptor by glutamate or other orthosteric ligands results in a reduction of adenylate cyclase via a Gai protein and a subsequent reduction of glutamate release from the presynaptic terminal. mGluR2 receptors are localized to regions of the brain involved with psychiatric disorders, including the prefrontal cortex, striatum, hippocampus, and amygdala. Excessive glutamate release has been hypothesized to contribute to the underlying pathophysiology in both anxiety and schizophrenia; therefore, activators of mGluR2 receptors may offer therapeutic benefits in these disorders. This biological phenomenon was demonstrated pre-clinically in a study by Moghaddam and Adams (1998) in which they treated rats with phencyclidine (PCP), an NMDA receptor blocker, and detected increased glutamate release in the mPFC and striatum of these animals as well as hyper-locomotion and working memory deficits. The mGluR2/3 agonist, LY-354740, lowered brain glutamate levels and reversed the behavioral effects of PCP. Many more studies have demonstrated efficacy in a variety of pre-clinical models of psychosis and anxiety with mGluR2/3 agonists. Such pre-clinical work led to the development of mGluR2/3 agonists for both anxiety and schizophrenia. Eli Lilly reported therapeutic effects of LY-544344 for anxiety in GAD patients (Dunayevich et al., 2008) and with LY-2140023 for relief of positive and negative symptoms in schizophrenia (Patil et al., 2007).

To date, most of the available pharmacological tools targeting the mGluR2 receptor have been structural analogues of glutamate and act as orthosteric agonists. While demonstrating proof of principle for use in psychiatric disease, agonists have poor pharmacokinetic profiles and poor brain penetration. Furthermore, several pre-clinical studies have demonstrated tolerance to mGluR2/3 agonists upon repeated dosing in rodents (Cartmell et al., 2000; Galici et al., 2005; Jones et al., 2005). Unlike orthosteric agonists, positive allosteric modulators (PAMs) only activate the receptor when glutamate or another orthosteric agonist is present. Therefore, PAMs are thought to retain spatial and temporal activity of glutamate transmission in the brain and would not continuously stimulate the mGluR2 receptor, potentially avoiding tolerance or unwanted side effects of the agonists. Furthermore, since PAMs bind to an allosteric site on the receptor, they can be designed to be selective for the mGluR2 receptor. Pre-clinical studies and early development of mGluR2 PAMs suggest that they will be effective therapies for positive and negative symptoms and co-morbidy anxiety in schizophrenia.

Based on the expression pattern and functional role of mGluR2, this receptor has emerged as an important target for drug discovery in a number of therapeutic indications. In clinical trials, activating mGluR2 was shown to be efficacious in treating anxiety disorders. In addition, activating mGluR2 has been shown to be efficacious in various animal models of schizophrenia, epilepsy, addiction/drug dependence, Parkinson's disease, pain, sleep disorders, and Huntington's disease. See the following publications: Positive allosteric modulators of the metabotropic glutamate receptor 2 for the treatment of schizophrenia. Mark E Fraley; *Expert Opin. Ther. Patents* (2009) 19(8); Biphenyl-indanone A, a positive allosteric modulator of the metabotropic glutamate receptor subtype 2, has antipsychotic- and anxiolytic-like effects in mice. Galici Ruggero; et al. *The Journal of Pharmacology and Experimental Therapeutics* (2006), 318 (1), 173-85; Potential psychiatric applications of metabotropic glutamate receptor agonists and antagonists. Krystal, John; et al. *CNS Drugs* (2010), 24(8), 669-693; Postsynaptic and presynaptic group II metabotropic glutamate receptor activation reduces neuronal excitability; in rat midline paraventricular thalamic nucleus. Hermes M L H J; et al.; *The Journal of Pharmacology and Experimental Therapeutics* (2011), 336(3), 840-9; Scaffold hopping from pyridones to imidazo[1,2-a]pyridines. New positive allosteric modulators of metabotropic glutamate 2 receptor. Gary Tresadern, et al.; *Bioorganic & Medicinal Chemistry Letters* 20 (2010) 175-179; 3-Benzyl-1,3-oxazolidin-2-ones as mGluR2 positive allosteric modulators: Hit-to lead and lead optimization. Allen J. Duplantier, et al.; *Bioorganic & Medicinal Chemistry Letters* 19 (2009) 2524-2529. Use of mGluR2 PAMs for the treatment of cocaine dependence: Design and synthesis of an orally active metabotropic glutamate receptor subtype-2 (mGluR2) positive allosteric modulator (PAM) that decreases cocaine self-administration in rats. Dhanya, Raveendra-Panickar; et al.; *Journal of Medicinal Chemistry* (2011), 54(1), 342-353; The mGluR2 Positive Allosteric Modulator BINA Decreases Cocaine Self-Administration and Cue-Induced Cocaine-Seeking and Counteracts Cocaine-Induced Enhancement of Brain Reward Function in Rats. Jin, Xinchun; et al.; *Neuropsychopharmacology* (2010), 35(10), 2021-2036.

The invention provides technical advantages, for example, the compounds are novel and are ligands for the mGluR2 receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating anxiety, schizophrenia, epilepsy, addiction/drug dependence, Parkinson's disease, pain, sleep disorders, or Huntington's disease, or other neurological or psychiatric disorders associated with glutamate dysfunction.

One aspect of the invention is a compound of formula I

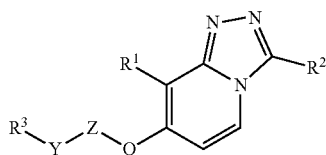

wherein:
R$^1$ is selected from the group consisting of hydrogen, cyano, halo, alkyl, haloalkyl, (cycloalkyl)alkyl, cycloalkyl, alkoxy, and haloalkoxy;
R$^2$ is selected from the group consisting of alkyl, haloalkyl, (cycloalkyl)alkyl, (halocycloalkyl)alkyl, (alkoxy)alkyl, (haloalkoxy)alkyl, cycloalkyl, halocycloalkyl, (alkyl)cycloalkyl, and (dialkyl)cycloalkyl;
R$^3$ is Ar$^1$ or OAr$^1$;
Ar$^1$ is phenyl, pyridinyl, pyridazinyl, pyrimidinyl, pyrazinyl, or triazinyl, and is substituted with 0-3 substituents selected from cyano, halo, alkyl, haloalkyl, cycloalkyl, alkoxy, cycloalkylalkoxy, and haloalkoxy;
Y is a bond or C$_{3-6}$ cycloalkyl substituted with 0-3 substituents selected from cyano, halo, alkyl, haloalkyl, hydroxy, alkoxy, and haloalkoxy; and
Z is a bond or C$_{1-3}$ alkyl substituted with 0-3 substituents selected from cyano, halo, alkyl, haloalkyl, hydroxy, alkoxy, and haloalkoxy;
provided that where Y and Z are bonds, R$^3$ is Ar$^1$;
or a pharmaceutically acceptable salt thereof.

Another aspect of the invention is a compound of formula I where:
R$^1$ is selected from the group consisting of hydrogen, cyano, halo, alkyl, haloalkyl, (cycloalkyl)alkyl, cycloalkyl, alkoxy, and haloalkoxy;
R$^2$ is selected from the group consisting of alkyl, haloalkyl, (cycloalkyl)alkyl, (halocycloalkyl)alkyl, (alkoxy)alkyl, (haloalkoxy)alkyl, cycloalkyl, and halocycloalky;
R$^3$ is Ar$^1$ or OAr$^1$;
Ar$^1$ is phenyl, pyridinyl, pyridazinyl, pyrimidinyl, pyrazinyl, or triazinyl, and is substituted with 0-3 substituents selected from cyano, halo, alkyl, haloalkyl, cycloalkyl, alkoxy, cycloalkoxy, and haloalkoxy;
Y is a bond or C$_{3-6}$ cycloalkyl substituted with 0-3 substituents selected from cyano, halo, alkyl, haloalkyl, hydroxy, alkoxy, and haloalkoxy; and
Z is a bond or C$_{1-3}$ alkyl substituted with 0-3 substituents selected from cyano, halo, alkyl, haloalkyl, hydroxy, alkoxy, and haloalkoxy;
provided that where Y and Z are bonds, R$^3$ is Ar$^1$;
or a pharmaceutically acceptable salt thereof.

Another aspect of the invention is a compound of formula I where R$^1$ is haloalkyl; R$^2$ is (cycloalkyl)alkyl; R$^3$ is Ar$^1$ or OAr$^1$; Ar$^1$ is phenyl, pyridinyl, or pyrimidinyl, and is substituted with 0-3 substituents selected from cyano, halo, alkyl, haloalkyl, cycloalkyl, alkoxy, cycloalkoxy, and haloalkoxy; Y is a bond or C$_{3-6}$ cycloalkyl substituted with 0-3 substituents selected from cyano, halo, alkyl, haloalkyl, hydroxy, alkoxy, and haloalkoxy; and Z is a bond or C$_{1-3}$ alkyl substituted with 0-3 substituents selected from cyano, halo, alkyl, haloalkyl, hydroxy, alkoxy, and haloalkoxy; or a pharmaceutically acceptable salt thereof.

Another aspect of the invention is a compound of formula I where R$^1$ is haloalkyl.

Another aspect of the invention is a compound of formula I where R$^2$ (cycloalkyl)alkyl.

Another aspect of the invention is a compound of formula I where R$^3$ is Ar$^1$.

Another aspect of the invention is a compound of formula I where Ar$^1$ is phenyl, pyridinyl, or pyrimidinyl, and is substituted with 0-3 substituents selected from cyano, halo, alkyl, haloalkyl, cycloalkyl, alkoxy, cycloalkoxy, and haloalkoxy.

Another aspect of the invention is a compound of formula I where Ar$^1$ is phenyl substituted with 0-3 substituents selected from cyano, halo, alkyl, haloalkyl, cycloalkyl, alkoxy, cycloalkoxy, and haloalkoxy.

Another aspect of the invention is a compound of formula I where Y is C$_{3-6}$ cycloalkyl substituted with 0-3 substituents selected from cyano, halo, alkyl, haloalkyl, hydroxy, alkoxy, and haloalkoxy.

Another aspect of the invention is a compound of formula I where Y is a bond and Z is C$_{1-3}$ alkyl substituted with 0-3 substituents selected from cyano, halo, alkyl, haloalkyl, hydroxy, alkoxy, and haloalkoxy.

Another aspect of the invention is a compound of formula I where —Y—Z— is 1,4-cyclohexanddiyl, 1,3-cyclobutanddiyl, or (cyclopropyl)methyl, and is substituted with 1 substituent selected from cyano, halo, alkyl, haloalkyl, hydroxy, alkoxy, and haloalkoxy.

For a compound of formula I, the scope of any instance of available substituent, including R$^1$, R$^2$, R$^3$, Ar$^1$, X$^1$, X$^2$, X$^3$, Y, and Z, can be used independently with the scope of any other instance of a variable substituent. As such, the invention includes combinations of the different aspects.

Unless specified otherwise, these terms have the following meanings "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. For clarity, a cycloalkyl moiety may be substituted at different positions, for example vicinal-disubstituted or gem-disubstituted. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The formula and variable designations used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Triazolopyridine ethers of formula (I) can be prepared in a number of ways known to those skilled in the art. Schemes 1-4 illustrate different methods that can be useful for the preparation of the titled compounds. In scheme 1, variously substituted alcohols $R^3OH$ can be added to 2,4-dichloropyridines 2 to afford 2-chloropyridyl ethers 3. The pyridyl ethers can be readily converted to the corresponding 2-hydrazinylpyridine ethers 3 upon treatment with hydrazine. A wide variety of acylhydrazides 5 can be prepared from the coupling of 2-hydrozinylpyridine ethers 3 with acylchlorides or carboxylic acids under standard conditions known to one skilled in the art. Cyclization of the acylhydrazide 4 to afford triazolopyridine ethers of formula (I) can be accomplished using mild dehydrating reagents including, but not limited to, 1-methoxy-N-triethylammoniosulfonyl-methanimidate, otherwise known as the Burgess reagent. Alcohols $R^3OH$, 2,4-dichloropyridines 2, carboxylic acids $R^1CO_2H$, and acyl chlorides $R^1C(O)Cl$ used to prepared compounds of formula (I) may be commercially available or readily prepared by employing standard methods known to those skilled in the art.

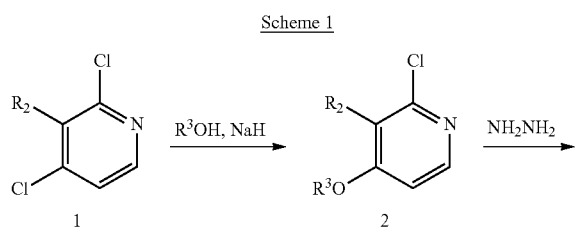

Scheme 1

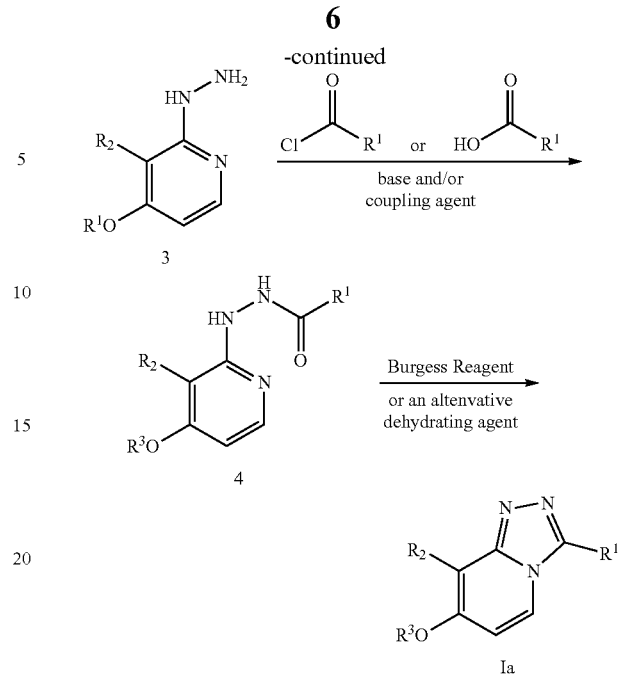

A second approach to the formation of triazolopyridine compounds of formula (I), is depicted in scheme 2. Benzylic ethers of formula 4a where Ar is phenyl or substituted phenyl, can be converted in a single reaction using phosphoryl chloride into the substituted 7-chlorotriazolopyridines 5. Coupling of the 7-chlorotriazolopyridines 5 with various alcohols $R^3OH$ under modified Buchwald-Hartwig type conditions can afford the titled compounds of formula (I). The ether coupling may be conducted using a mixture of reagents including, but not limited to, cesium carbonate, (S)—(R)-JOSIPHOS, and allylpalladium chloride dimer.

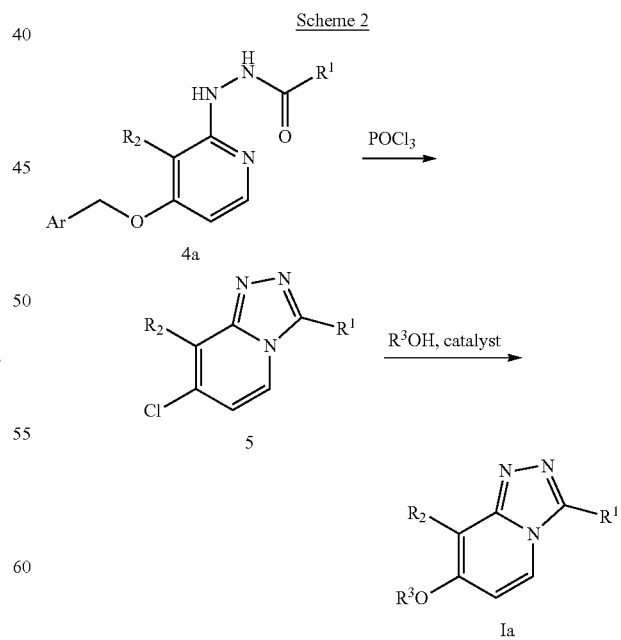

Another approach to the formation of triazolopyridine compounds of formula (I), is outlined in scheme 3. In this route, benzylic triazolopyridine ethers of formula 6, which can be obtained via scheme 1, are hydrogenolytically cleaved to provide the 7-hydroxyltriazolopyridines 7. Alkylation of 7-hydroxyltriazolopyridines 7 with electrophiles R³X under a variety of standard conditions known to one skilled in the art can provide compounds of formula (Ia). Electrophiles that are useful for this reaction include, but are not limited to, substituted benzylic halides.

Scheme 3

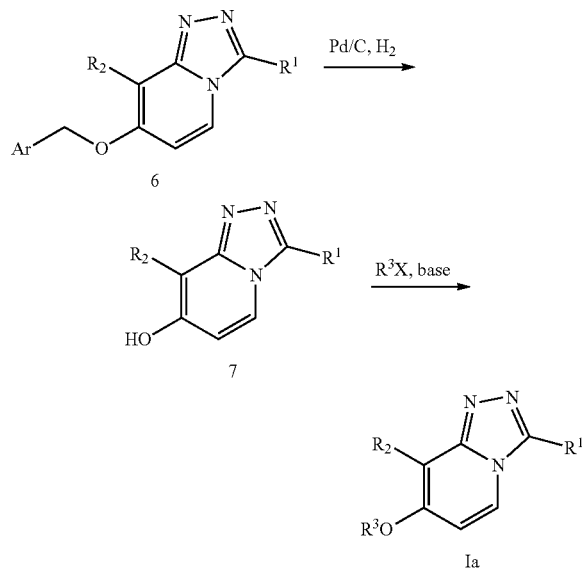

Chlorotriazolopyridine ethers of formula (Ib) can be prepared according to the route illustrated in scheme 4. The ethers (Ib) can result from a metal mediated coupling of a triazolopyridine iodide 10 with an alcohol R³OH. The requisite iodide can be prepared in two steps from the known iodopyridine 8 using standard conditions known one skilled in the art.

Scheme 4

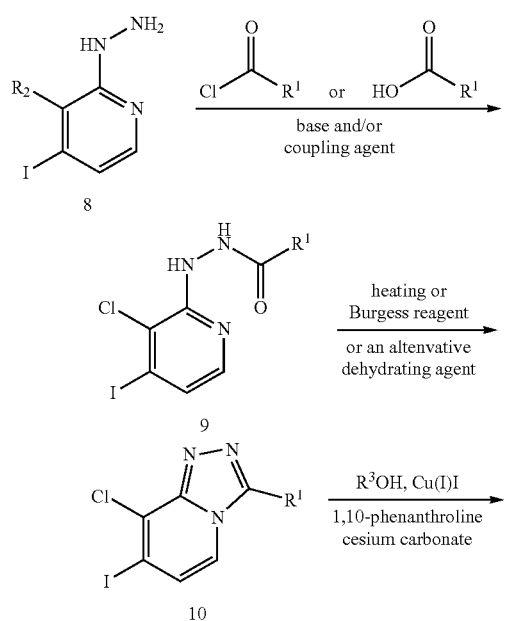

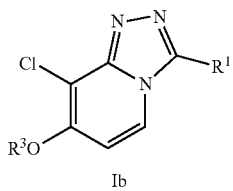

Biological Methods

Cell Culture.
Clonally expressed human mGluR2 in HEK293 background was glutamate starved overnight in media without glutamine (GIBCO MEM 12360), containing 10% FBS, 1% penicillin streptomycin.

cAMP Measurement.
On the day of the assay, media was removed, cells washed with PBS, cells harvested and pelleted by centrifugation. Cell pellets were resuspended in stimulation buffer without forskolin and counted. A solution of $1.25 \times 10^6$ cells/mL was prepared and dispensed to plates using a Combi liquid handler (Thermo). A standard curve was created using a top concentration of cAMP of 1 μM in the stimulation buffer, 1:3 dilutions over 14 points in the absence of cells. Plates were read by time-resolved fluorescence at 665 nM and 618 nM and a ratio was calculated via in house software, (665 nM/618 nM)*$10^4$. In house software converted the fluorescence value ratios to units of cAMP concentration, which is then used to calculate % inhibition for each test compound.

MGluR2 cAMP Assay Materials and Methods.
Compounds were added to white, standard volume 384 non-binding surface plates (Corning 3574). Cells were resuspended in stimulation buffer consisting of Hanks Balanced Salt Solution (14175-095) pH 7.0, 20 mM HEPES, 2.0 mM $CaCl_2$, 5.0 mM $MgCl_2$, and 1 mM IBMX (Sigma 15879), 1 μM forskolin, and 1 μM LY-341495 for 30 min. Buffer without forskolin was used as a negative control. Solutions of D2 and cryptate detection reagents from the CISBIO dynamic cAMP kit (62AM4PEJ) were diluted 1:40 in lysis buffer. Lysis buffer consisted of 50 mM Phosphate Buffer pH 7.0, 800 mM Potassium Fluoride, 0.2% BSA, and 1.0% Triton. Assay reaction was terminated by addition of detection reagents in lysis buffer. One hour later, plates were read on a PE Viewlux. Data was extracted, and concentration response curves generated by fitting the data to a standard 4 parameter logistic equation from which $EC_{50}$ values were determined. See table 1.

TABLE 1

| Activity in mGluR2 cAMP assay for examples 1-85 | |
|---|---|
| Example No. | $EC_{50}$ (nM) |
| 1 | 1.8 |
| 2 | 5.5 |
| 3 | 11 |
| 4 | 10 |
| 5 | 1.0 |
| 6 | 11 |
| 7 | 13 |
| 8 | 11 |
| 9 | 0.8 |
| 10 | 0.8 |
| 11 | 18 |
| 12 | 130 |
| 13 | 13 |

TABLE 1-continued

Activity in mGluR2 cAMP assay for examples 1-85

| Example No. | $EC_{50}$ (nM) |
|---|---|
| 14 | 230 |
| 15 | 80 |
| 16 | 15 |
| 17 | 1.4 |
| 18 | 5.9 |
| 19 | 0.3 |
| 20 | 0.4 |
| 21 | 31 |
| 22 | 4.9 |
| 23 | 120 |
| 24 | 36 |
| 25 | 25 |
| 26 | 0.8 |
| 27 | 0.6 |
| 28 | 0.7 |
| 29 | 13 |
| 30 | 16 |
| 31 | 1.3 |
| 32 | 0.3 |
| 33 | 4.0 |
| 34 | 1.6 |
| 35 | 0.2 |
| 36 | 0.2 |
| 37 | 0.2 |
| 38 | 1.4 |
| 39 | 0.6 |
| 40 | 1.4 |
| 41 | 2.2 |
| 42 | 1.9 |
| 43 | 1.4 |
| 44 | 1.9 |
| 45 | 1.3 |
| 46 | 0.5 |
| 47 | 0.8 |
| 48 | 0.5 |
| 49 | 0.4 |
| 50 | 2.7 |
| 51 | 43 |
| 52 | 1.6 |
| 53 | 0.3 |
| 54 | 2.2 |
| 55 | 20 |
| 56 | 22 |
| 57 | 0.5 |
| 58 | 60 |
| 59 | 530 |
| 60 | 18 |
| 61 | 40 |
| 62 | 270 |
| 63 | 100 |
| 64 | 32 |
| 65 | 110 |
| 66 | 11 |
| 67 | 55 |
| 68 | 68 |
| 69 | 32 |
| 70 | 140 |
| 71 | 11 |
| 72 | 42 |
| 73 | 22 |
| 74 | 21 |
| 75 | 29 |
| 76 | 4.1 |
| 77 | 1.7 |
| 78 | 2.6 |
| 79 | 1.1 |
| 80 | 0.4 |
| 81 | 1.5 |
| 82 | 20 |
| 83 | 6.1 |
| 84 | 5.8 |
| 85 | 25 |
| 86 | 6.9 |
| 87 | 61 |
| 88 | 3.1 |
| 89 | 41 |
| 90 | 19 |
| 91 | 83 |
| 92 | 35 |
| 93 | 20 |
| 94 | 12 |
| 95 | 1.0 |
| 96 | 0.4 |
| 97 | 1.0 |
| 98 | 5.1 |
| 99 | 0.5 |

Pharmaceutical Compositions and Methods of Treatment

Compounds of formula I modulate to mGluR2 and can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of anxiety, schizophrenia, epilepsy, addiction/drug dependence, Parkinson's disease, pain, sleep disorders, or Huntington's disease, or other neurological or psychiatric disorders associated with glutamate dysfunction, which comprises administering to a patient a therapeutically affective amount of a compound of formula I.

Another aspect of the invention is a method for the treatment of anxiety or schizophrenia which comprises administering to a patient a therapeutically affective amount of a compound of formula I.

Another aspect of the invention is a method for the treatment of anxiety which comprises administering to a patient a therapeutically affective amount of a compound of formula I.

Another aspect of the invention is a method for the treatment of schizophrenia which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of anxiety, schizophrenia, epilepsy, addiction/drug dependence, Parkinson's disease, pain, sleep disorders, or Huntington's disease, or other neurological or psychiatric disorders associated with glutamate dysfunction.

Another aspect of the invention is the use of a compound of formula I in the manufacture of a medicament for the treatment of anxiety.

Another aspect of the invention is the use of a compound of formula I in the manufacture of a medicament for the treatment of schizophrenia.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tic" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art. Standard conditions typically used for preparative LC-MS are as follows: column=XBridge C18, 19×200 mm, 5-µm particles; mobile phase A=5:95 acetonitrile:water with 10-mM ammonium acetate; mobile phase B=95/5 acetonitrile:water with 10-mM ammonium acetate; gradient=30-70% B over 20 minutes, then a 7-minute hold at 100% B; flow=20 mL/min. Standard conditions typically used for reverse phase preparative HPLC are as follows: column=Sunfire PrepC18 OBD 10 µm, 50×250 mm column; mobile phase A=90% MeOH/10% water with 0.1% TFA; mobile phase B=90% MeOH/10% water with 0.1% TFA; linear gradient 10-100% B over 34 min, then a 20 minute hold at 100% B; flow=50 mL/min.

Preparation A

2-Hydrazinyl-4-((1-phenylcyclohexyl)methoxy)-3-(trifluoromethyl)pyridine

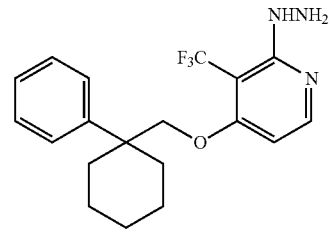 [SMILES: NNc1nccc(OCC2(c3ccccc3)CCCCC2)c1C(F)(F)F]

Step A1

A solution of (1-phenylcyclohexyl)methanol (commercially available, 500 mg, 2.63 mmol) in DMF (3 mL) was added to a mixture of 60% sodium hydride dispersion in mineral oil (163 mg, 4.07 mmol) and DMF (10 mL) in an ice bath at 0° C. The mixture was allowed to stir at 0° C. for 30 min, then a solution of 2,4-dichloro-3-(trifluoromethyl)pyridine (WO 2010/130422, 596 mg, 2.76 mmol) in DMF (3 mL) was quickly added. The resulting mixture was stirred at 0° C. for 1 hour, then quenched by the addition of water. The aqueous mixture was extracted with ethyl acetate. The combined organic layers were washed with brine, dried over magnesium sulfate, filtered, and concentrated in vacuo. The residue was purified using silica gel column chromatography (5:1 hexanes/ethyl acetate) to afford 2-chloro-4-((1-phenyl-cyclohexyl)methoxy)-3-(trifluoromethyl)pyridine (875 mg, 90% yield) as a clear viscous oil. LC-MS (M+H)$^+$ 370.0. $^1$H NMR (500 MHz, chloroform-d) δ ppm 8.25 (d, J=6.0 Hz, 1H), 7.53-7.42 (m, 2H), 7.42-7.33 (m, 2H), 7.27-7.22 (m, 1H), 6.73 (d, J=6.0 Hz, 1H), 3.91 (s, 2H), 2.30 (d, J=13.3 Hz, 2H), 1.90-1.77 (m, 2H), 1.68-1.57 (m, 3H), 1.48-1.35 (m, 3H).

Step A2

A mixture of 2-chloro-4-((1-phenylcyclohexyl)methoxy)-3-(trifluoromethyl)pyridine (from step A1, 479 mg, 1.30 mmol), dioxane (10 mL), and hydrazine monohydrate (1.28 mL, 16.8 mmol) was heated together in a sealed vial for 18 h in an oil bath at 100° C. The reaction mixture was cooled to rt and concentrated in vacuo. The residue was partitioned between aqueous sodium bicarbonate and dichloromethane. The aqueous layer was extracted with dichloromethane. The combined organic extracts were washed with brine, dried over magnesium sulfate, filtered, and concentrated in vacuo to afford 2-hydrazinyl-4-((1-phenylcyclohexyl)methoxy)-3-(trifluoromethyl)pyridine (437 mg, 92% yield) as a white solid. LC-MS (M+H)$^+$ 366.1. $^1$H NMR (500 MHz, DMSO-d$_6$) δ 8.10 (d, J=5.8 Hz, 1H), 7.44 (d, J=7.5 Hz, 2H), 7.33 (t, J=7.7 Hz, 3H), 7.24-7.12 (m, 1H), 6.46 (d, J=6.0 Hz, 1H), 4.25 (s, 2H), 3.96 (s, 2H), 2.19 (d, J=13.7 Hz, 2H), 1.84-1.69 (m, 2H), 1.62-1.41 (m, 3H), 1.39-1.20 (m, 3H).

Preparation B 4-(2-(4-Chlorophenyl)-2-methylpropoxy)-2-hydrazinyl-3-(trifluoromethyl)pyridine

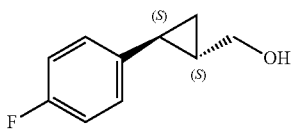

Step B1

2-Chloro-4-(2-(4-chlorophenyl)-2-methylpropoxy)-3-(trifluoromethyl)pyridine (810 mg, 82% yield) was prepared from 2-(4-chlorophenyl)-2-methylpropan-1-ol (commercially available) and 2,4-dichloro-3-(trifluoromethyl)pyridine (WO 2010/130422) following a procedure analogous to step A1. LC-MS (M+H)$^+$ 363.9. $^1$H NMR (500 MHz, chloroform-d) δ 8.32 (d, J=5.8 Hz, 1H), 7.39-7.29 (m, 4H), 6.82 (d, J=5.8 Hz, 1H), 4.00 (s, 2H), 1.49 (s, 6H).

Step B2

4-(2-(4-Chlorophenyl)-2-methylpropoxy)-2-hydrazinyl-3-(trifluoromethyl)pyridine (457 mg, quantitative yield) was prepared from 2-chloro-4-(2-(4-chlorophenyl)-2-methylpropoxy)-3-(trifluoromethyl)pyridine (from step B1) following a procedure analogous to step A2. LC-MS (M+H)$^+$ 360.1. $^1$H NMR (500 MHz, DMSO-d$_6$) δ 8.16 (d, J=5.8 Hz, 1H), 7.52-7.41 (m, 2H), 7.41-7.30 (m, 3H), 6.55 (d, J=6.0 Hz, 1H), 4.26 (s, 2H), 4.11 (s, 2H), 1.37 (s, 6H).

Preparation C (((1S,2S)-2-(4-Fluorophenyl)cyclopropyl)methanol

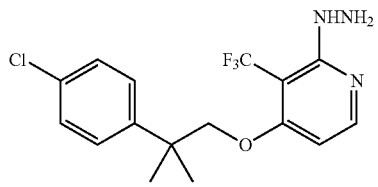 [SMILES: CC(C)(COc1ccnc(NN)c1C(F)(F)F)c1ccc(Cl)cc1]

((1S,2S)-2-(4-fluorophenyl)cyclopropyl)methanol (737 mg, 4.43 mmol, 89% yield) was prepared from (1S,2S)-2-(4-fluorophenyl)cyclopropanecarboxylic acid (WO 2012/155199) following a procedure analogous to preparation F2. LC-MS (M−H$_2$O+H)$^+$=149.2.

Preparation D 4-(((1S,2S)-2-(4-Fluorophenyl)cyclopropyl)methoxy)-2-hydrazinylnicotinonitrile

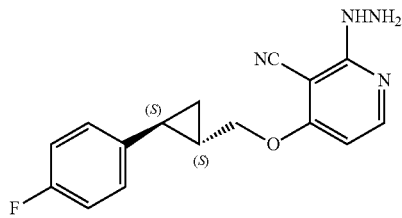

Step D1

2-Bromo-4-(((1S,2S)-2-(4-fluorophenyl)cyclopropyl)methoxy)nicotinonitrile (244 mg, 47% yield) was prepared from ((1S,2S)-2-(4-fluorophenyl)cyclopropyl)methanol (from preparation F) and 2,4-dibromonicotinonitrile (WO 2009/062676) following a procedure analogous to step A1. The crude was purified using silica gel column chromatography (2:1-1:1 hexanes/ethyl acetate). $^1$H NMR (500 MHz, chloroform-d) δ 8.37 (d, J=6.0 Hz, 1H), 7.16-7.07 (m, 2H), 7.03-6.94 (m, 2H), 6.89 (d, J=6.0 Hz, 1H), 4.21 (qd, J=10.4, 6.8 Hz, 2H), 2.10-2.01 (m, 1H), 1.61-1.53 (m, 1H), 1.13 (ddt, J=24.0, 8.8, 5.5 Hz, 2H).

Step D2

4-(((1S,2S)-2-(4-Fluorophenyl)cyclopropyl)methoxy)-2-hydrazinylnicotinonitrile (186 mg, 90% yield) was prepared in from 2-bromo-4-(((1S,2S)-2-(4-fluorophenyl)cyclopropyl)methoxy)nicotinonitrile (from step D1, 240 mg, 0.691 mmol) following a procedure analogous to step A2. LC-MS (M+H)$^+$ 299.2.

Preparation E 2-(4-fluorophenyl)propan-1-ol

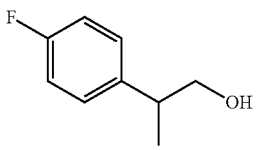

Step E1

To a solution of diisopropylamine (4.24 mL, 29.7 mmol) in THF (100 mL) at −5° C. under nitrogen was added a solution of 2.5 M n-butyllithium in hexanes (11.9 mL, 29.7 mmol) dropwise via syringe. After stirring for 15 min, methyl 2-(4-fluorophenyl)acetate (commercially available, 5.0 g, 29.7 mmol) was added. The mixture was stirred at −5° C. for 30 min and then treated with iodomethane (1.86 mL, 29.7 mmol). The reaction mixture was allowed to gradually warm to rt. After 4 h at rt, the reaction mixture was poured into a solution of aqueous ammonium chloride. The resulting mixture was extracted with diethyl ether. The combined organic extracts were washed with brine, dried (magnesium sulfate), filtered, and concentrated in vacuo. The crude product was purified using silica gel column chromatography (20:1 hexane/ethyl acetate) to afford methyl 2-(4-fluorophenyl)propanoate (2.32 g, 43% yield) as a clear liquid. $^1$H NMR (500 MHz, chloroform-d) δ 7.33-7.25 (m, 2H), 7.09-6.98 (m, 2H), 3.73 (q, J=7.2 Hz, 1H), 3.69 (s, 3H), 1.51 (d, J=7.2 Hz, 3H).

Step E2

Sodium borohydride (2.41 g, 63.7 mmol) was added portionwise to a solution of methyl 2-(4-fluorophenyl)propanoate (from step E1, 2.32 g, 12.7 mmol) in THF (25 ml) at rt. The mixture was allowed to stir at rt for 18 h. The reaction was quenched with water and adjusted to pH 3-4 with 1 M aqueous hydrochloric acid. The resulting mixture was extracted with ethyl acetate. The combined organic layers were washed with brine, dried (magnesium sulfate), filtered and concentrated in vacuo. The crude product was purified using silica gel column chromatography (2:1-1:1 hexane/ethyl acetate) to afford 2-(4-fluorophenyl)propan-1-ol (0.746 g, 38% yield). $^1$H NMR (400 MHz, chloroform-d) δ 7.25-7.16 (m, 2H), 7.08-6.97 (m, 2H), 3.77-3.62 (m, 2H), 2.95 (sxt, J=6.9 Hz, 1H), 1.32 (dd, J=6.7, 5.6 Hz, 1H), 1.27 (d, J=7.0 Hz, 3H).

Preparation F 2-(2-Chloro-6-fluorophenyl)propan-1-ol

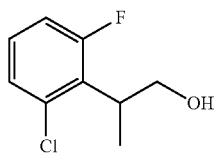

Step F1

A solution of 1.0 M potassium tert-butoxide in tert-butanol (12.3 mL, 12.3 mmol) was added to a mixture of methyl 2-(2-chloro-6-fluorophenyl)acetate (2.5 g, 12.3 mmol), iodomethane (0.772 mL, 12.3 mmol), and THF (50 mL) maintained at 0° C. After complete addition, the cold bath was removed and the mixture was allowed to stir at rt for 4 days. The reaction was quenched with a solution of aqueous ammonium chloride, poured into water, and extracted with ethyl acetate. The combined organics extracts were washed with brine, dried (magnesium sulfate), filtered, and concentrated in vacuo. The crude product was purified using silica gel column chromatography (50:1 hexane/ethyl acetate) to afford a sample of methyl 2-(2-chloro-6-fluorophenyl)propanoate (318 mg, 11% yield) contaminated with ~14% of methyl 2-(2-chloro-6-fluorophenyl)acetate. The impure sample of methyl 2-(2-chloro-6-fluorophenyl)propanoate was carried forward without further purification. LC-MS (M+H)$^+$ 217.1.

Step F2

A solution of methyl 2-(2-chloro-6-fluorophenyl)propanoate (from step F1, 318 mg, 1.47 mmol) (contaminated with approximately 14% methyl 2-(2-chloro-6-fluorophenyl)acetate) in dry THF (10 mL) was carefully added over 2 min to solution of LAH (111 mg, 2.94 mmol) in dry THF (20 mL) at 0° C. The reaction mixture was allowed to warm to rt and was stirred for 2 h. The reaction was quenched with 0.110 mL of water and then 0.110 mL of 15% NaOH/water. After stirring for 10 min, an additional 0.22 mL of water was added. The mixture was allowed to stir for 3 hours and it was filtered through celite. The filtrate was concentrated in vacuo. The residue was dried under high vacuum for 16 h to afford 2-(2-chloro-6-fluorophenyl)propan-1-ol (0.276 g, 99% yield) as a clear viscous oil. HPLC and 1H NMR data indicated that the product was approximately 86% pure. The impure crude product was carried forward without purification. $^1$H NMR (500 MHz, chloroform-d) δ 7.22-7.18 (m, 1H), 7.14 (td, J=8.1, 5.7 Hz, 1H), 7.00-6.93 (m, 1H), 3.99-3.92 (m, 1H), 3.92-3.85 (m, 1H), 3.73-3.64 (m, 1H), 1.36 (dd, J=7.0, 1.5 Hz, 3H).

Preparation G 4-(2-(2-Chloro-6-fluorophenyl)propoxy)-2-hydrazinyl-3-(trifluoromethyl)pyridine

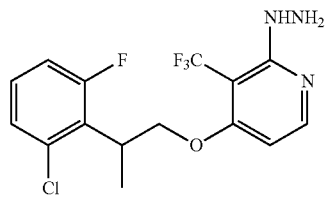 [SMILES: CC(COc1ccnc(NN)c1C(F)(F)F)c1c(F)cccc1Cl]

Step G1

2-Chloro-4-(2-(2-chloro-6-fluorophenyl)propoxy)-3-(trifluoromethyl)pyridine (304 mg, 56% yield) was prepared from 2-(2-chloro-6-fluorophenyl)propan-1-ol (from preparation F) and 2,4-dichloro-3-(trifluoromethyl)pyridine (WO 2010/130422) following a procedure analogous to step A1. LC-MS (M+H)$^+$ 368.0.

Step G2

4-(2-(2-Chloro-6-fluorophenyl)propoxy)-2-hydrazinyl-3-(trifluoromethyl)pyridine (292 mg, 97% yield) was prepared from 2-chloro-4-(2-(2-chloro-6-fluorophenyl)propoxy)-3-(trifluoromethyl)pyridine (from step G1) according to the methods described in step A2. LC-MS (M+H)+ 364.1.

Preparation H 2-(4-Fluorophenyl)-2-methylpropan-1-ol

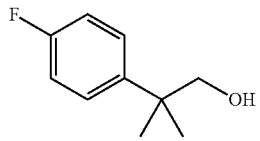

Step H1

A solution of 1.0 M potassium tert-butoxide in tert-butanol (92 mL, 92 mmol) was added to a mixture of 2-(4-fluorophenyl)acetonitrile (commercially available, 5.0 g, 37.0 mmol), iodomethane (6.36 mL, 102 mmol), and THF (100 mL) maintained at 0° C. After complete addition, the cold bath was removed and the mixture was allowed to stir at rt for 18 h. The reaction was quenched with a saturated aqueous solution of ammonium chloride, poured into water, and extracted with ethyl acetate. The combined organics were washed with brine, dried (magnesium sulfate), filtered, and concentrated in vacuo. The crude product was purified using silica gel column chromatography (40:1 hexane/ethyl acetate) to afford 2-(4-fluorophenyl)-2-methylpropanenitrile (5.2 g, 84% yield) as a clear liquid. $^1$H NMR (500 MHz, chloroform-d) δ 7.50-7.41 (m, 2H), 7.14-7.03 (m, 2H), 1.73 (s, 6H).

Step H2

A mixture of 2-(4-fluorophenyl)-2-methylpropanenitrile (from step H1, 5.2 g, 31.9 mmol) and 15% aqueous sodium hydroxide (80 mL) was heated at reflux for 16 h. The mixture was cooled to rt and extracted with diethyl ether. The aqueous layer was made acidic with 1 N aqueous hydrochloric acid (300 mL) and was then extracted with diethyl ether. The acidic organic extract was washed with brine, dried (magnesium sulfate), filtered and concentrated in vacuo. The residue was dried under high vacuum for several hours to afford 2-(4-fluorophenyl)-2-methylpropanoic acid (1.89 g, 33% yield) as a white solid. $^1$H NMR (500 MHz, chloroform-d) δ 7.44-7.32 (m, 2H), 7.09-6.97 (m, 2H), 1.60 (s, 6H).

Step H3

2-(4-Fluorophenyl)-2-methylpropan-1-ol (1.77 g, quantitative yield) was prepared from 2-(4-fluorophenyl)-2-methylpropanoic acid (from step H2) following a procedure analogous to step F2. $^1$H NMR (500 MHz, chloroform-d) δ 7.42-7.32 (m, 2H), 7.08-6.98 (m, 2H), 3.61 (s, 2H), 1.34 (s, 6H).

Preparation I 2-(4-Fluorophenoxy)-2-methylpropan-1-ol

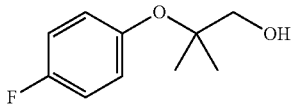

A solution of 2-(4-fluorophenoxy)-2-methylpropanoic acid (commercially available, 2.5 g, 12.6 mmol) in dry THF (10 mL) was carefully added over 2 min to solution of LAH (0.718 g, 18.92 mmol) in dry THF (20 mL) at 0° C. The reaction mixture was allowed to warm to rt and was stirred for 4 h. The reaction was quenched with 0.7 mL of water and 0.7 mL of 1M NaOH. After stirring for 10 min, an additional 1.4 mL of water was added. The mixture was allowed to stir for 2 h, and then was filtered through celite. The filtrate was concentrated in vacuo. The residue was purified using silica gel column chromatography (2:1 hexane/ethyl acetate) to afford 2-(4-fluorophenoxy)-2-methylpropan-1-ol (606 mg, 25% yield) as a clear viscous oil. $^1$H NMR (500 MHz, chloroform-d) δ 7.03-6.88 (m, 4H), 3.59 (s, 2H), 1.25 (s, 6H).

Preparation J 4-(2-(4-Fluorophenoxy)-2-methylpropoxy)-2-hydrazinyl-3-(trifluoromethyl)pyridine

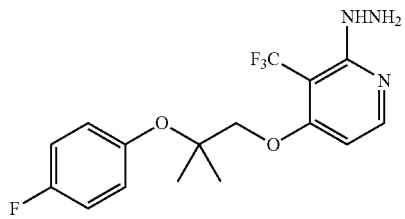 [SMILES: CC(C)(COc1ccnc(NN)c1C(F)(F)F)Oc1ccc(F)cc1]

Step J1

2-Chloro-4-(2-(4-fluorophenoxy)-2-methylpropoxy)-3-(trifluoromethyl)pyridine (515 mg, 87% yield) was prepared from 2-(4-fluorophenoxy)-2-methylpropan-1-ol (from preparation I) and 2,4-dichloro-3-(trifluoromethyl)pyridine (WO 2010/130422) following a procedure analogous to step A1. LC-MS (M+H)+ 364.0. $^1$H NMR (500 MHz, chloroform-d) δ 8.38 (d, J=5.8 Hz, 1H), 7.01-6.92 (m, 4H), 6.91 (d, J=5.3 Hz, 1H), 4.07 (s, 2H), 1.42 (s, 6H).

Step J2

4-(2-(4-fluorophenoxy)-2-methylpropoxy)-2-hydrazinyl-3-(trifluoromethyl)pyridine (482 mg, 95% yield) was prepared from 2-chloro-4-(2-(4-fluorophenoxy)-2-methylpropoxy)-3-(trifluoromethyl)pyridine (from step J1) following a procedure analogous to step A2. LC-MS (M+H)+ 360.1.

Preparation K

2-(4-Fluorophenyl)-3-hydroxy-2-methylpropanenitrile

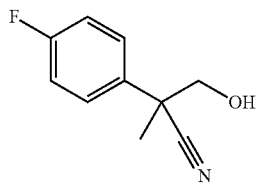

Step K1

A solution of 1.0 M potassium tert-butoxide in tert-butanol (55.5 mL, 55.5 mmol) was added to a mixture of 2-(4-fluorophenyl)acetonitrile (commercially available, 5.0 g, 37.0 mmol), iodomethane (2.31 mL, 37.0 mmol), and THF (100 mL) maintained at 0° C. After complete addition, the cold bath was removed and the mixture was allowed to stir at rt for 18 h. The reaction was quenched with a saturated aqueous solution of ammonium chloride, poured into water, and extracted with ethyl acetate. The combined organics were washed with brine, dried (magnesium sulfate), filtered, and concentrated in vacuo. The crude product was purified using silica gel column chromatography (40:1 hexane/ethyl acetate) to afford 2-(4-fluorophenyl)propanenitrile (2.9 g, 53% yield) as a clear liquid. $^1$H NMR (500 MHz, chloroform-d) δ 7.38-7.30 (m, 2H), 7.12-7.05 (m, 2H), 3.90 (q, J=7.2 Hz, 1H), 1.65 (d, J=7.2 Hz, 3H).

Step K2

A 40% solution of benzyltrimethylammonium hydroxide in methanol (2.80 g, 6.70 mmol) was added to a mixture of 2-(4-fluorophenyl)propanenitrile (from step K1, 1.0 g, 6.70 mmol) and paraformaldehyde (0.805 g, 26.8 mmol) in pyridine (7 mL). The mixture was left to stir at rt for 18 h. The reaction mixture was poured into water, and extracted with ether. The combined organic extracts were washed brine and dried over magnesium sulfate. The mixture was filtered and concentrated in vacuo. The residue was purified using silica gel column chromatography (2:1 ethyl acetate/hexanes) to afford 2-(4-fluorophenyl)-3-hydroxy-2-methylpropanenitrile (1.2 g, 98% yield) as a clear viscous oil. $^1$H NMR (500 MHz, chloroform-d) δ 7.50-7.43 (m, 2H), 7.17-7.09 (m, 2H), 3.90-3.79 (m, 2H), 2.01 (br. s., 1H), 1.75 (s, 3H).

Preparation L

2-(4-Fluorophenyl)-3-(2-hydrazinyl-3-(trifluoromethyl)pyridin-4-yloxy)-2-methylpropanenitrile

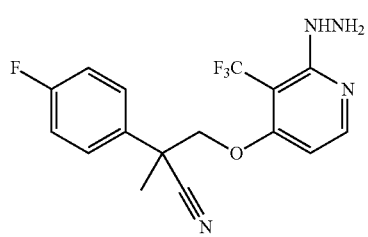 [SMILES: CC(C#N)(COc1ccnc(NN)c1C(F)(F)F)c1ccc(F)cc1]

Step L1

3-((2-Chloro-3-(trifluoromethyl)pyridin-4-yl)oxy)-2-(4-fluorophenyl)-2-methylpropanenitrile (899 mg, 75% yield) was prepared from 2-(4-fluorophenyl)-3-hydroxy-2-methylpropanenitrile (from preparation K, 600 mg, 3.35 mmol) and 2,4-dichloro-3-(trifluoromethyl)pyridine (WO 2010/130422) following a procedure analogous to step A1. LC-MS (M+H)$^+$ 359.0.

Step L2

2-(4-Fluorophenyl)-3-((2-hydrazinyl-3-(trifluoromethyl)pyridin-4-yl)oxy)-2-methylpropanenitrile (934 mg, quantitative yield) was prepared from 34-(2-chloro-3-(trifluoromethyl)pyridin-4-yl)oxy)-2-(4-fluorophenyl)-2-methylpropanenitrile (from step L1, 890 mg, 2.48 mmol) following a procedure analogous to step A2. LC-MS (M+H)$^+$ 355.1.

Preparation M

2-(4-Chlorophenoxy)-2-methylpropan-1-ol

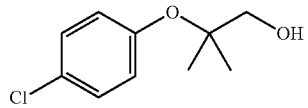

2-(4-Chlorophenoxy)-2-methylpropan-1-ol (2.3 g, 11.46 mmol, 98% yield) was prepared from 2-(4-chlorophenoxy)-2-methylpropanoic acid (commercially available) following a procedure analogous to preparation I. $^1$H NMR (500 MHz, chloroform-d) δ 7.27-7.23 (m, 2H), 6.96-6.90 (m, 2H), 3.59 (s, 2H), 1.27 (s, 6H).

Preparation N

4-(2-(4-chlorophenoxy)-2-methylpropoxy)-2-hydrazinyl-3-(trifluoromethyl)pyridine

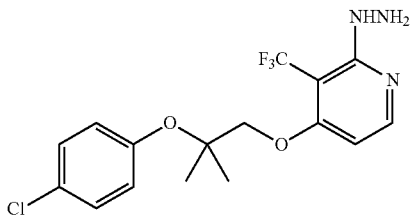 [SMILES: CC(C)(COc1ccnc(NN)c1C(F)(F)F)Oc1ccc(Cl)cc1]

Step N1

2-Chloro-4-(2-(4-chlorophenoxy)-2-methylpropoxy)-3-(trifluoromethyl)pyridine (657 mg, 87% yield) was prepared from 2-(4-chlorophenoxy)-2-methylpropan-1-ol (from preparation M) and 2,4-dichloro-3-(trifluoromethyl)pyridine (WO 2010/130422) following a procedure analogous to step A1. LC-MS (M+H)$^+$ 380.0.

Step N2

4-(2-(4-Chlorophenoxy)-2-methylpropoxy)-2-hydrazinyl-3-(trifluoromethyl)pyridine (647 mg, quantitative yield)

was prepared from 2-chloro-4-(2-(4-chlorophenoxy)-2-methylpropoxy)-3-(trifluoromethyl)pyridine (from step N1) following a procedure analogous to step A2. LC-MS (M+H)+ 376.1.

Preparation O 2-(2,4-Difluorophenoxy)-2-methylpropan-1-ol

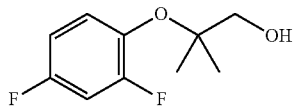

Step O1

A mixture of 2,4-difluorophenol (commercially available, 10 g, 77 mmol), ethyl 2-bromo-2-methylpropanoate (15 g, 77 mmol), and potassium carbonate (10.6 g, 77 mmol) in DMF (50 mL) was stirred at rt for 3 days. The reaction mixture was poured into water. The aqueous mixture was extracted with ethyl acetate/hexane (90/10). The combined organics were washed with water and then brine. The organic layer was dried (magnesium sulfate), filtered and concentrated in vacuo. The residue was purified by silica gel column chromatography (5:1 hexane/ethyl acetate) to afford ethyl 2-(2,4-difluorophenoxy)-2-methylpropanoate (7.07 g, 37% yield) as a clear thin liquid. LC-MS (M+H)+ 245.1. 1H NMR (500 MHz, chloroform-d) δ 7.04 (td, J=9.1, 5.6 Hz, 1H), 6.84 (ddd, J=10.8, 8.2, 3.1 Hz, 1H), 6.75 (dddd, J=9.2, 7.7, 3.0, 1.8 Hz, 1H), 4.26 (q, J=7.1 Hz, 2H), 1.56 (s, 7H), 1.31 (t, J=7.1 Hz, 3H).

Step O2

2-(2,4-Difluorophenoxy)-2-methylpropan-1-ol (2.05 g, 10.14 mmol, 94% yield) was prepared from ethyl 2-(2,4-difluorophenoxy)-2-methylpropanoate (from step 01) following a procedure analogous to step F2. 1H NMR (500 MHz, chloroform-d) δ 7.04 (td, J=9.1, 5.6 Hz, 1H), 6.90-6.84 (m, 1H), 6.79 (dddd, J=9.1, 7.7, 3.1, 1.7 Hz, 1H).

Preparation P 4-(2-(2,4-Difluorophenoxy)-2-methylpropoxy)-2-hydrazinyl-3-(trifluoromethyl)pyridine

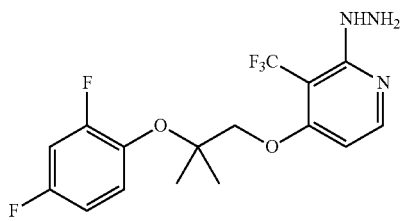 [SMILES: CC(C)(COc1ccnc(NN)c1C(F)(F)F)Oc1ccc(F)cc1F]

Step P1

2-Chloro-4-(2-(2,4-difluorophenoxy)-2-methylpropoxy)-3-(trifluoromethyl)pyridine (555 mg, 72% yield) was prepared from 2-(2,4-difluorophenoxy)-2-methylpropan-1-ol (from preparation O) and 2,4-dichloro-3-(trifluoromethyl)pyridine (WO 2010/130422) following a procedure analogous to step A1. LC-MS (M+H)+ 382.0. 1H NMR (500 MHz, chloroform-d) δ 8.39 (d, J=5.8 Hz, 1H), 7.03 (td, J=9.0, 5.7 Hz, 1H), 6.94 (d, J=6.0 Hz, 1H), 6.86 (ddd, J=10.5, 8.4, 3.0 Hz, 1H), 6.83-6.75 (m, 1H), 4.14 (s, 2H), 1.50-1.36 (m, 6H).

Step P2

4-(2-(2,4-Difluorophenoxy)-2-methylpropoxy)-2-hydrazinyl-3-(trifluoromethyl)pyridine (536 mg, 99% yield) was prepared from 2-chloro-4-(2-(2,4-difluorophenoxy)-2-methylpropoxy)-3-(trifluoromethyl)pyridine (from step P1) following a procedure analogous to step A2. LC-MS (M+H)+ 378.1.

Preparation Q (1s,4s)-1-(4-Fluorophenyl)-4-hydroxycyclohexanecarbonitrile

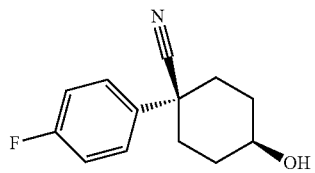 [SMILES: N#C[C@]1(c2ccc(F)cc2)CC[C@H](O)CC1]

Sodium borohydride (47.1 mg, 1.246 mmol) was added to a stirred solution of 1-(4-fluorophenyl)-4-oxocyclohexanecarbonitrile [(from J. Med. Chem. 1975, 18, 593) 246 mg, 1.13 mmol] in ethanol (15 mL) maintained in a 0° C. ice bath. After 2 h, the reaction was diluted with water and the pH was adjusted to 2 by the addition of 1 N aqueous hydrochloric acid. The mixture was extracted with ethyl acetate. The combined organics were washed with brine, dried (magnesium sulfate), filtered and concentrated in vacuo to afford (1s,4s)-1-(4-fluorophenyl)-4-hydroxycyclohexanecarbonitrile (250 mg, 99% yield). LC-MS (M+H)+ 220.1.

Preparation R (1s,4s)-1-(4-Fluorophenyl)-4-(2-hydrazinyl-3-(trifluoromethyl)pyridin-4-yloxy)cyclohexanecarbonitrile

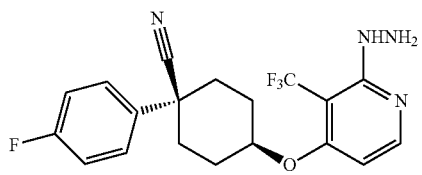 [SMILES: N#C[C@]1(c2ccc(F)cc2)CC[C@H](Oc2ccnc(NN)c2C(F)(F)F)CC1]

Step R1

(1s,4s)-4-((2-Chloro-3-(trifluoromethyl)pyridin-4-yl)oxy)-1-(4-fluorophenyl)cyclohexanecarbonitrile (270 mg, 58% yield) was prepared from (1s,4s)-1-(4-fluorophenyl)-4-hydroxycyclohexanecarbonitrile (from preparation Q) and 2,4-dichloro-3-(trifluoromethyl)pyridine (WO 2010/130422) following a procedure analogous to step A1. LC-MS (M+H)+ 399.1. $^1$H NMR (500 MHz, DMSO-d$_6$) δ 8.50 (d, J=6.0 Hz, 1H), 7.67-7.55 (m, 2H), 7.50 (d, J=6.0 Hz, 1H), 7.37-7.25 (m, 2H), 4.93-4.79 (m, 1H), 2.25 (d, J=10.5 Hz, 4H), 2.18-2.07 (m, 2H), 1.84-1.72 (m, 2H).

Step R2

(1s,4s)-1-(4-Fluorophenyl)-4-((2-hydrazinyl-3-(trifluoromethyl)pyridin-4-yl)oxy)cyclohexanecarbonitrile (255 mg, 0.647 mmol, 97% yield) was prepared from (1s,4s)-4-((2-chloro-3-(trifluoromethyl)pyridin-4-yl)oxy)-1-(4-fluorophenyl)cyclohexanecarbonitrile (265 mg, 0.665 mmol) (from step R1) following a procedure analogous to step A2. LC-MS (M+H)+ 395.1.

Preparation S 4-((1s,4s)-4-(4-Fluorophenyl)-4-methoxycyclohexyloxy)-2-hydrazinyl-3-(trifluoromethyl)pyridine

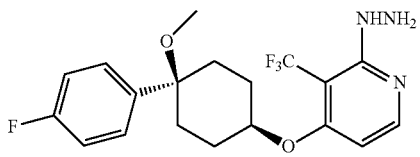 [SMILES: CO[C@]1(c2ccc(F)cc2)CC[C@H](Oc2ccnc(NN)c2C(F)(F)F)CC1]

Step S1

2-Chloro-4-(((1s,4s)-4-(4-fluorophenyl)-4-methoxycyclohexyl)oxy)-3-(trifluoromethyl)pyridine (257 mg, 57% yield) was prepared from (1s,4s)-4-(4-fluorophenyl)-4-methoxycyclohexanol (J. Med. Chem 1973, 16, 1251) and 2,4-dichloro-3-(trifluoromethyl)pyridine (WO 2010/130422) following a procedure analogous to step A1. LC-MS (M+H)+ 404.1. $^1$H NMR (500 MHz, chloroform-d) δ 8.33 (d, J=6.0 Hz, 1H), 7.44-7.34 (m, 2H), 7.11-7.02 (m, 2H), 6.90 (d, J=5.8 Hz, 1H), 4.45 (tt, J=9.9, 4.8 Hz, 1H), 2.98 (s, 3H), 2.27-2.17 (m, 2H), 2.12-1.96 (m, 4H), 1.86-1.73 (m, 2H).

Step S2

4-(((1s,4s)-4-(4-Fluorophenyl)-4-methoxycyclohexyl)oxy)-2-hydrazinyl-3-(trifluoromethyl)pyridine (247 mg, 97% yield) was prepared from 2-chloro-4-(((1s,4s)-4-(4-fluorophenyl)-4-methoxycyclohexyl)oxy)-3-(trifluoromethyl)pyridine (from step S1) following a procedure analogous to step A2. LC-MS (M+H)+ 400.1.

Preparation T

2-Hydrazinyl-4-((1r,4r)-4-phenylcyclohexyloxy)-3-(trifluoromethyl)pyridine

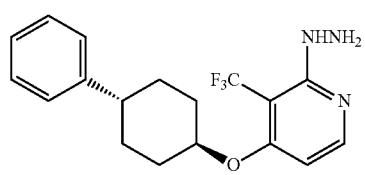 [SMILES: NNc1nccc(O[C@H]2CC[C@H](c3ccccc3)CC2)c1C(F)(F)F]

Step T1

2-Chloro-4-(((1r,4r)-4-phenylcyclohexyl)oxy)-3-(trifluoromethyl)pyridine (395 mg, 1.11 mmol, 65% yield) was prepared from (1r,4r)-4-phenylcyclohexanol (commercially available) and 2,4-dichloro-3-(trifluoromethyl)pyridine (WO 2010/130422) following a procedure analogous to step A1. LC-MS (M+H)+ 356.1. $^1$H NMR (500 MHz, chloroform-d) δ 8.33 (d, J=5.8 Hz, 1H), 7.37-7.30 (m, 2H), 7.26-7.19 (m, 3H), 6.93 (d, J=6.0 Hz, 1H), 4.55-4.42 (m, 1H), 2.64 (tt, J=11.9, 3.5 Hz, 1H), 2.35-2.23 (m, 2H), 2.13-2.02 (m, 2H), 1.83-1.70 (m, 2H), 1.70-1.59 (m, 2H).

Step T2

2-Hydrazinyl-4-(((1I,4I)-4-phenylcyclohexyl)oxy)-3-(trifluoromethyl)pyridine (385 mg, 100% yield) was prepared from 2-chloro-4-(((1r,4r)-4-phenylcyclohexyl)oxy)-3-(trifluoromethyl)pyridine (from step T1) following a procedure analogous to step A2. LC-MS (M+H)+ 352.2.

Preparation U 2-(4-Fluorophenyl)-3-hydroxy-2-methylpropanenitrile

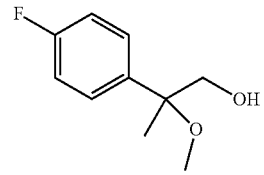

1-Fluoro-4-(prop-1-en-2-yl)benzene (3.1 g, 22.77 mmol) was added dropwise over 10 min to a solution of mCPBA (5.66 g, 25.3 mmol) in methanol (50 mL) maintained in an ice-bath. After complete addition, the mixture was allowed to warm to rt. After stirring at rt for 30 min, the reaction mixture was heated in an oil bath at 40° C. for 16 h. The reaction mixture was diluted with 50 mL of water. The mixture was concentrated in vacuo. The resulting white aqueous slurry was diluted with 1 N NaOH (50 mL) and extracted with diethyl ether. The combined organics layers were washed with brine, dried (magnesium sulfate), filtered, and concentrated in vacuo. The crude product was purified using silica gel column chromatography (2:1 hexanes/ethyl acetate) to afford 2-(4-fluorophenyl)-2-methoxypropan-1-ol (2.89 g, 66% yield) as a clear oil. $^1$H NMR (500 MHz, chloroform-d) δ 7.40-7.33 (m, 2H), 7.10-7.02 (m, 2H), 3.63 (d, J=11.1 Hz, 1H), 3.49 (d, J=11.1 Hz, 1H), 3.14 (s, 3H), 1.61 (s, 3H).

Preparation V 4-(2-(4-fluorophenyl)-2-methoxypropoxy)-2-hydrazinyl-3-(trifluoromethyl)pyridine

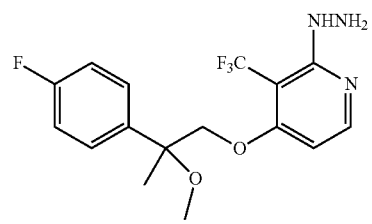 [SMILES: COC(C)(COc1ccnc(NN)c1C(F)(F)F)c1ccc(F)cc1]

Step V1

2-Chloro-4-(2-(4-fluorophenyl)-2-methoxypropoxy)-3-(trifluoromethyl)pyridine (387 mg, 53% yield) was prepared from 2-(4-fluorophenyl)-2-methoxypropan-1-ol (from preparation U) and 2,4-dichloro-3-(trifluoromethyl)pyridine (WO 2010/130422) following a procedure analogous to step A1. LC-MS (M+H)+ 364.1. $^1$H NMR (400 MHz, chloroform-d) δ 8.31 (d, J=6.0 Hz, 1H), 7.47-7.39 (m, 2H), 7.12-7.03 (m, 2H), 6.82 (d, J=5.8 Hz, 1H), 4.05 (dd, J=56.5, 9.0 Hz, 2H), 3.17 (s, 3H), 1.76 (s, 3H).

Step V2

4-(2-(4-Fluorophenyl)-2-methoxypropoxy)-2-hydrazinyl-3-(trifluoromethyl)pyridine (375 mg, 100% yield) was prepared from 2-chloro-4-(2-(4-fluorophenyl)-2-methoxypropoxy)-3-(trifluoromethyl)pyridine (from step V1) following a procedure analogous to step A2. LC-MS (M+H)+ 360.1.

Preparation W (1s,4s)-1-(3,4-Difluorophenyl)cyclohexane-1,4-diol

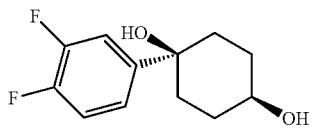

(1s,4s)-1-(3,4-Difluorophenyl)cyclohexane-1,4-diol (491 mg, 97% yield) was prepared from 4-(3,4-difluorophenyl)-4-hydroxycyclohexanone (U.S. Pat. No. 5,391,570) following a procedure analogous to preparation Q. The crude product was obtained as a >9:1 mixture of diasteromers and was carried forward without purification. $^1$H NMR (500 MHz, chloroform-d) δ 7.22 (ddd, J=12.1, 7.8, 1.8 Hz, 1H), 7.16-7.07 (m, 2H), 3.72-3.63 (m, 1H), 2.98 (s, 3H), 2.11-2.03 (m, 2H), 1.92-1.85 (m, 2H), 1.79-1.61 (m, 4H).

Preparation X (1s,4s)-1-(3,4-Difluorophenyl)-4-(2-hydrazinyl-3-(trifluoromethyl)pyridin-4-yloxy)cyclohexanol

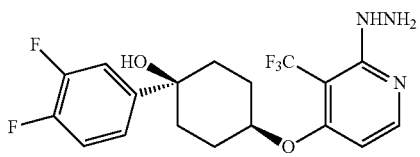 [SMILES: NNc1nccc(O[C@H]2CC[C@](O)(c3ccc(F)c(F)c3)CC2)c1C(F)(F)F]

Step X1

(1s,4s)-4-((2-chloro-3-(trifluoromethyl)pyridin-4-yl)oxy)-1-(3,4-difluorophenyl)cyclohexanol (267 mg, 50% yield) was prepared from (1s,4s)-Difluorophenyl)cyclohexane-1,4-diol (from preparation W) and 2,4-dichloro-3-(trifluoromethyl)pyridine (WO 2010/130422) following a procedure analogous to step A1. LC-MS (M+H)+ 408.0. $^1$H NMR (500 MHz, chloroform-d) δ 8.34 (d, J=5.8 Hz, 1H), 7.35 (ddd, J=11.9, 7.6, 2.3 Hz, 1H), 7.25-7.19 (m, 1H), 7.19-7.12 (m, 1H), 6.91 (d, J=5.8 Hz, 1H), 4.56-4.42 (m, 1H), 2.20-2.10 (m, 2H), 2.10-2.03 (m, 2H), 2.01-1.90 (m, 4H).

Step X2

(1s,4s)-1-(3,4-Difluorophenyl)-4-((2-hydrazinyl-3-(trifluoromethyl)pyridin-4-yl)oxy)cyclohexanol (262 mg, quantitative yield) was prepared from (1s,4s)-4-((2-chloro-3-(trifluoromethyl)pyridin-4-yl)oxy)-1-(3,4-difluorophenyl)cyclohexanol (from step X1) following a procedure analogous to step A2. LC-MS (M+H)+ 404.1.

Preparation Y 4-((1s,4s)-4-(3,4-difluorophenyl)-4-methoxycyclohexyloxy)-2-hydrazinyl-3-(trifluoromethyl)pyridine

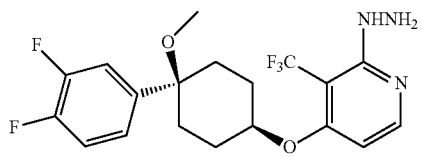 [SMILES: CO[C@]1(c2ccc(F)c(F)c2)CC[C@H](Oc2ccnc(NN)c2C(F)(F)F)CC1]

Step Y1

2-Chloro-4-(((1s,4s)-4-(3,4-difluorophenyl)-4-methoxycyclohexyl)oxy)-3-(trifluoromethyl)pyridine (260 mg, 37% yield) was prepared from (1s,4s)-4-(3,4-difluorophenyl)-4-methoxycyclohexanol (J. Med. Chem 1973, 16, 1251) and 2,4-dichloro-3-(trifluoromethyl)pyridine (WO 2010/130422) following a procedure analogous to step A1. LC-MS (M+H)+ 422.1. $^1$H NMR (500 MHz, chloroform-d) δ 8.33 (d, J=6.0 Hz, 1H), 7.24 (ddd, J=11.9, 7.6, 2.1 Hz, 1H), 7.20-7.10 (m, 2H), 6.90 (d, J=6.0 Hz, 1H), 4.48-4.41 (m, 1H), 3.00 (s, 3H), 2.23-2.14 (m, 2H), 2.08-1.99 (m, 4H), 1.83-1.71 (m, 2H).

Step Y2

4-((1s,4s)-4-(3,4-Difluorophenyl)-4-methoxycyclohexyloxy)-2-hydrazinyl-3-(trifluoromethyl)pyridine (257 mg, quantitative yield) was prepared from 2-chloro-4-(((1s,4s)-4-(3,4-difluorophenyl)-4-methoxycyclohexyl)oxy)-3-(trifluoromethyl)pyridine (from step Y1) following a procedure analogous to step A2. LC-MS (M+H)+ 418.3.

Preparation Z 4-((1-(4-Chlorophenyl)cyclopropyl)methoxy)-2-hydrazinyl-3-(trifluoromethyl)pyridine

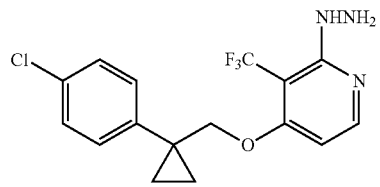 [SMILES: NNc1nccc(OCC2(c3ccc(Cl)cc3)CC2)c1C(F)(F)F]

Step Z1

2-Chloro-4-((1-(4-chlorophenyl)cyclopropyl)methoxy)-3-(trifluoromethyl)pyridine (438 mg, 74% yield) was prepared from (1-(4-chlorophenyl)cyclopropyl)methanol (commercially available) and 2,4-dichloro-3-(trifluoromethyl)pyridine (WO 2010/130422) following a procedure analogous to step A1. LC-MS (M+H)$^+$ 362.0. $^1$H NMR (500 MHz, chloroform-d) δ 8.31 (d, J=5.8 Hz, 1H), 7.39-7.35 (m, 2H), 7.32-7.29 (m, 2H), 6.75 (d, J=6.0 Hz, 1H), 4.11 (s, 2H), 1.09-1.02 (m, 4H).

Step Z2

4-((1-(4-Chlorophenyl)cyclopropyl)methoxy)-2-hydrazinyl-3-(trifluoromethyl)pyridine (439 mg, quantitative yield) was prepared from 2-chloro-4-((1-(4-chlorophenyl)cyclopropyl)methoxy)-3-(trifluoromethyl)pyridine (from step Z1) following a procedure analogous to step A2. LC-MS (M+H)$^+$ 358.0.

Preparation AA 4-((1-(4-Fluorophenyl)cyclopropyl)methoxy)-2-hydrazinyl-3-(trifluoromethyl)pyridine

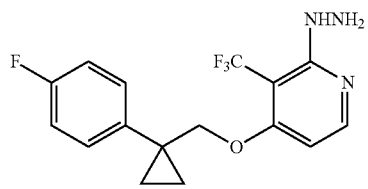 [SMILES: NNc1nccc(OCC2(c3ccc(F)cc3)CC2)c1C(F)(F)F]

Step AA1

2-Chloro-4-((1-(4-fluorophenyl)cyclopropyl)methoxy)-3-(trifluoromethyl)pyridine (537 mg, 86% yield) was prepared from (1-(4-fluorophenyl)cyclopropyl)methanol (commercially available) and 2,4-dichloro-3-(trifluoromethyl)pyridine (WO 2010/130422) following a procedure analogous to step A1. LC-MS (M+H)$^+$ 346.0. $^1$H NMR (500 MHz, chloroform-d) δ 8.30 (d, J=6.0 Hz, 1H), 7.43-7.38 (m, 2H), 7.04-6.98 (m, 2H), 6.75 (d, J=5.8 Hz, 1H), 4.10 (s, 2H), 1.08-1.00 (m, 4H).

Step AA2

4-((1-(4-Fluorophenyl)cyclopropyl)methoxy)-2-hydrazinyl-3-(trifluoromethyl)pyridine (500 mg, 94% yield) was prepared from 2-chloro-4-((1-(4-fluorophenyl)cyclopropyl)methoxy)-3-(trifluoromethyl)pyridine (from step AA1) following a procedure analogous to step A2. LC-MS (M+H)$^+$ 342.0.

Preparation AB (trans-2-(4-Chlorophenyl)cyclopropyl)methanol

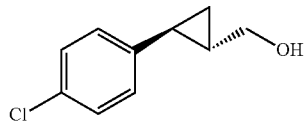 [SMILES: OC[C@H]1C[C@@H]1c1ccc(Cl)cc1]

Step AB1

A mixture of trans-2-(4-chlorophenyl)cyclopropanecarboxylic acid (commercially available, 1.0 g, 5.09 mmol), methanol (29.1 ml), and sulfuric acid (0.813 ml, 15.3 mmol) was heated in a sealed vial at 72° C. for 18 h. The reaction was carefully neutralized by the addition of aqueous 10% sodium carbonate solution. The resulting mixture was evaporated in vacuo. The residue was partitioned between ethyl acetate and water. The aqueous phase was extracted with ethyl acetate. The combined organic layers were washed with brine, dried (sodium sulfate), filtered, and concentrated in vacuo to afford methyl trans-2-(4-chlorophenyl)cyclopropanecarboxylate (1.07 g, quantitative % yield) as a light brown oil. $^1$H NMR (500 MHz, chloroform-d) δ 7.29-7.26 (m, 2H), 7.07-7.03 (m, 2H), 3.74 (s, 3H), 2.52 (ddd, J=9.3, 6.4, 4.2 Hz, 1H), 1.89 (ddd, J=8.5, 5.3, 4.3 Hz, 1H), 1.65-1.60 (m, 1H), 1.33-1.29 (m, 1H).

Step AB2

To a stirring suspension of LAH (0.589 g, 15.5 mmol) in THF (2.5 mL) was added dropwise a solution of methyl 2-(4-chlorophenyl)cyclopropanecarboxylate (from step AB1, 1.07 g, 5.07 mmol) in THF (5 mL). The resulting mixture was stirred at rt for 18 h. The reaction was quenched by the addition of aqueous ammonium hydroxide solution. The reaction mixture was slurried in a bilayer of water and ethyl acetate and filtered through celite. The layers were separated and the aqueous layer was extracted with ethyl acetate. The combined organic layers were washed with brine, dried (magnesium sulfate), filtered, and concentrated in vacuo. The residue was purified by silica-gel column chromatography (0-35% ethyl acetate/hexane) to afford (trans-2-(4-chlorophenyl)cyclopropyl)methanol (582 mg, 3.19 mmol, 62.8% yield). LC-MS (M–H$_2$O+H)$^+$ 165.0.

Preparation AC (±)-4-(((1S,2S)-2-(4-chlorophenyl)cyclopropyl)methoxy)-2-hydrazinyl-3-(trifluoromethyl)pyridine

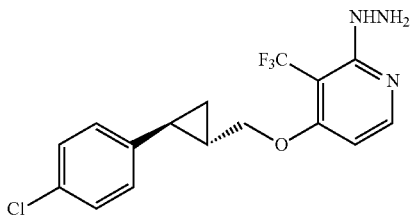 [SMILES: NNc1nccc(OC[C@H]2C[C@@H]2c2ccc(Cl)cc2)c1C(F)(F)F]

Step AC1

(±)-2-Chloro-4-(((1S,2S)-2-(4-chlorophenyl)cyclopropyl)methoxy)-3-(trifluoromethyl)pyridine (450 mg, 76% yield) was prepared from (trans-2-(4-chlorophenyl)cyclopropyl)methanol (from preparation AB) and 2,4-dichloro-3-(trifluoromethyl)pyridine (WO 2010/130422) following a procedure analogous to step A1. $^1$H NMR (500 MHz, chloroform-d) δ 8.38 (d, J=4.7 Hz, 1H), 7.28-7.25 (m, 2H), 7.09-7.05 (m, 2H), 6.89 (d, J=4.6 Hz, 1H), 4.27 (dd, J=9.8, 6.1 Hz, 1H), 4.16-4.07 (m, 1H), 2.07-2.01 (m, 1H), 1.56 (dd, J=12.6, 6.3 Hz, 1H), 1.18-1.10 (m, 2H).

Step AC2

4-((1-(4-Fluorophenyl)cyclopropyl)methoxy)-2-hydrazinyl-3-(trifluoromethyl)pyridine (451 mg, quantitative yield) was prepared from (±)-2-chloro-4-(((1S,2S)-2-(4-chlorophenyl)cyclopropyl)methoxy)-3-(trifluoromethyl)pyridine (from step AC1) following a procedure analogous to step A2. LC-MS (M+H)+ 358.0.

Preparation AD (trans-2-(2-fluoro-6-methoxyphenyl)cyclopropyl)methanol

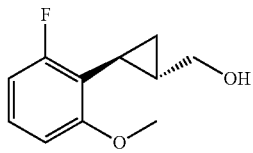

Step AD1

A solution of (E)-3-(2-fluoro-6-methoxyphenyl)acrylic acid (commercially available, 1.8 g, 9.18 mmol) in thionyl chloride (30 mL) was heated to reflux for 2 h. The resulting mixture was concentrated in vacuo to afford a tan solid. The solid was dissolved in ethyl acetate (50 mL) and added to a solution of N,O-dimethylhydroxylamine, HCl (1.1 g, 11.3 mmol) and potassium carbonate (3.80 g, 27.5 mmol) in water (50 mL). The mixture was stirred for 1 hr. The ethyl acetate layer was separated, washed with water, washed with brine, and concentrated to afford (E)-3-(2-fluoro-6-methoxyphenyl)-N-methoxy-N-methylacrylamide as a brown oil (2.15 g, 98% yield). LC-MS (M+H)+ 240.1.

Step AD2

A 60% dispersion of sodium hydride in mineral (3.01 g, 75 mmol) was added in 1 g portions to vigorously stirred DMSO (75 mL). After the foaming subsided, trimethylsulfoxonium iodide (16.6 g, 75 mmol) was added portion wise over 1 h, while maintaining the internal temperature below 35° C. After an additional 30 min, a solution of (E)-3-(2-fluoro-6-methoxyphenyl)-N-methoxy-N-methylacrylamide (from step AD1, 6.0 g, 25 mmol) in DMSO (50 mL) was added dropwise while still maintaining the internal temperature between 30-35° C. The resulting mixture was stirred for 1.5 h at rt. The rxn was quenched with aqueous ammonium chloride solution (25 mL). The resulting mixture was diluted with EtOAc and washed with water. The organic layer was washed with brine, dried (magnesium sulfate), filtered, and concentrated in vacuo to afford to afford trans-2-(2-fluoro-6-methoxyphenyl)-N-methoxy-N-methylcyclopropanecarboxamide (8.1 g, quantitative yield) as a clear oil. LC-MS (M+H)+ 254.1.

Step AD3 trans-2-(2-Fluoro-6-methoxyphenyl)-N-methoxy-N-methylcyclopropanecarboxamide (from step AD2, 7.0 g, 27.6 mmol) was treated at rt with a solution of 2.5 M aqueous sodium hydroxide (75 ml, 188 mmol). The reaction mixture was stirred at rt for 18 h and heated at reflux for and additional 1.5 h. The reaction mixture was diluted with water, and extracted with DCM. The aqueous layer was made acidic with concentrated hydrochloric acid. The resulting white precipitate was collected and dried under high vacuum to afford trans-2-(2-fluoro-6-methoxyphenyl)cyclopropanecarboxylic acid (4.4 g, 76% yield) as a white solid. 1H NMR (400 MHz, chloroform-d) δ 7.15 (td, J=8.3, 6.5 Hz, 1H), 6.72-6.60 (m, 2H), 3.86 (s, 3H), 2.59 (ddd, J=9.5, 7.0, 4.5 Hz, 1H), 2.15 (dt, J=7.8, 5.0 Hz, 1H), 1.68 (td, J=7.5, 4.5 Hz, 1H), 1.65-1.57 (m, 1H).

Step AD4 trans-methyl 2-(2-fluoro-6-methoxyphenyl)cyclopropanecarboxylate (395 mg, 99% yield) was prepared from trans-2-(2-fluoro-6-methoxyphenyl)cyclopropanecarboxylic acid (from step AD3) following a procedure analogous to step AB1. LC-MS (M+H)+ 225.0. 1H NMR (500 MHz, chloroform-d) δ 7.13 (td, J=8.3, 6.6 Hz, 1H), 6.67-6.61 (m, 2H), 3.84 (s, 3H), 3.76-3.74 (m, 3H), 2.58-2.49 (m, 1H), 2.18 (dt, J=8.2, 4.9 Hz, 1H), 1.60 (dt, J=7.6, 3.8 Hz, 1H), 1.54-1.51 (m, 1H).

Step AD5

(trans-2-(2-fluoro-6-methoxyphenyl)cyclopropyl)methanol (175 mg, 51% yield) was prepared from trans-methyl 2-(2-fluoro-6-methoxyphenyl)cyclopropanecarboxylate (from step AD4) following a procedure and purification method analogous to step AB2. LCMS (M-H2O+H)+ 179.0. 1H NMR (500 MHz, chloroform-d) δ 7.14 (td, J=8.4, 6.5 Hz, 1H), 6.70-6.63 (m, 2H), 3.96-3.86 (m, 4H), 3.31 (dd, J=10.8, 8.9 Hz, 1H), 1.60 (dt, J=8.9, 5.3 Hz, 1H), 1.47-1.39 (m, 1H), 1.31-1.23 (m, 1H), 0.93 (dt, J=9.0, 5.3 Hz, 1H).

Preparation AE (±)-4-(((1S,2S)-2-(2-Fluoro-6-methoxyphenyl)cyclopropyl)methoxy)-2-hydrazinyl-3-(trifluoromethyl)pyridine

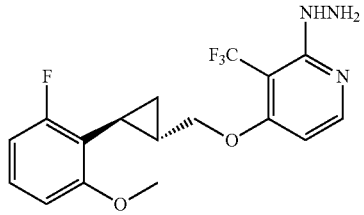 [SMILES: COc1cccc(F)c1[C@H]1C[C@@H]1COc1ccnc(NN)c1C(F)(F)F]

Step AE1

(±)-2-Chloro-4-(((1S,2S)-2-(2-fluoro-6-methoxyphenyl)cyclopropyl)methoxy)-3-(trifluoromethyl)pyridine (298 mg, 89% yield) was prepared from (trans-2-(2-fluoro-6-methoxyphenyl)cyclopropyl)methanol (from preparation AD) and 2,4-dichloro-3-(trifluoromethyl)pyridine (WO 2010/130422) following a procedure analogous to step A1. 1H NMR (500 MHz, chloroform-d) δ 8.36 (d, J=6.0 Hz, 1H), 7.13 (td, J=8.3, 6.4 Hz, 1H), 6.93 (d, J=5.8 Hz, 1H), 6.71-6.61 (m, 2H), 4.33 (dd, J=10.1, 5.9 Hz, 1H), 4.14 (dd, J=10.1, 6.6 Hz, 1H), 3.83 (s, 3H), 1.94 (dt, J=9.2, 5.5 Hz, 1H), 1.83 (dt, J=8.2, 5.9 Hz, 1H), 1.34 (dt, J=8.4, 5.5 Hz, 1H), 1.11-1.02 (m, 1H).

Step AE2

(±)-4-(((1S,2S)-2-(2-Fluoro-6-methoxyphenyl)cyclopropyl)methoxy)-2-hydrazinyl-3-(trifluoromethyl)pyridine (294 mg, quantitative yield) was prepared from (±)-2-chloro-4-(((1S,2S)-2-(2-fluoro-6-methoxyphenyl)cyclopropyl)methoxy)-3-(trifluoromethyl)pyridine (from step AE1) following a procedure analogous to step A2. LC-MS (M+H)⁺ 371.1.

Preparation AF (trans-2-(2-methoxyphenyl)cyclopropyl)methanol

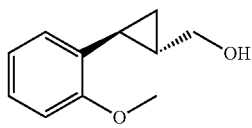

Step AF1 trans-Methyl 2-(2-methoxyphenyl)cyclopropanecarboxylate (1.07 g, quantitative yield) was prepared from trans-methyl 2-(2-methoxyphenyl)cyclopropanecarboxylic (commercially available) following a procedure analogous to step AB1. LC-MS (M+H)⁺ 206.4.

Step AF2

(trans-2-(2-Methoxyphenyl)cyclopropyl)methanol (959 mg, quantitative yield) was prepared from trans-methyl 2-(2-methoxyphenyl)cyclopropanecarboxylate (from step AF1) following a procedure analogous to step AB2. $^1$H NMR (400 MHz, chloroform-d) δ 7.24-7.18 (m, 1H), 7.01-6.97 (m, 1H), 6.94-6.85 (m, 2H), 3.91 (s, 3H), 3.90-3.87 (m, 1H), 3.31 (dd, J=10.8, 8.8 Hz, 1H), 1.92 (dt, J=8.6, 5.2 Hz, 1H), 1.26-1.19 (m, 1H), 1.14-1.07 (m, 1H), 0.89 (dt, J=8.7, 5.1 Hz, 1H).

Preparation AG (±)-2-Hydrazinyl-4-(((1S,2S)-2-(2-methoxyphenyl)cyclopropyl)methoxy)-3-(trifluoromethyl)pyridine

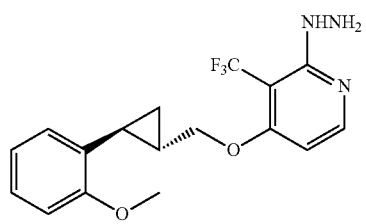 [SMILES: COc1ccccc1[C@H]1C[C@@H]1COc1ccnc(NN)c1C(F)(F)F]

Step AG1

(±)-2-Chloro-4-(((1S,2S)-2-(2-methoxyphenyl)cyclopropyl)methoxy)-3-(trifluoromethyl)pyridine (360 mg, 60% yield) was prepared from (trans-2-(2-methoxyphenyl)cyclopropyl)methanol (from preparation AF) and 2,4-dichloro-3-(trifluoromethyl)pyridine (WO 2010/130422) following a procedure analogous to step A1. $^1$H NMR (500 MHz, chloroform-d) δ 8.36 (d, J=5.8 Hz, 1H), 7.20 (ddd, J=8.1, 7.1, 2.1 Hz, 1H), 6.94-6.87 (m, 4H), 4.30 (dd, J=10.1, 6.3 Hz, 1H), 4.13 (dd, J=10.1, 6.9 Hz, 1H), 3.86 (s, 3H), 2.25 (dt, J=8.9, 5.3 Hz, 1H), 1.55-1.49 (m, 1H), 1.14 (dt, J=8.4, 5.5 Hz, 1H), 1.06 (dt, J=9.0, 5.3 Hz, 1H).

Step AG2

(±)-2-Hydrazinyl-4-(((1S,2S)-2-(2-methoxyphenyl)cyclopropyl)methoxy)-3-(trifluoromethyl)pyridine (312 mg, 88% yield) was prepared from (±)-2-chloro-4-(((1S,2S)-2-(2-methoxyphenyl)cyclopropyl)methoxy)-3-(trifluoromethyl)pyridine (from step AG1) following a procedure analogous to step A2. LC-MS (M+H)⁺ 354.1.

Preparation AH (trans-2-(2-(Trifluoromethoxy)phenyl)cyclopropyl)methanol

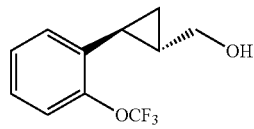 [SMILES: OC[C@H]1C[C@@H]1c1ccccc1OC(F)(F)F]

Step AH1 trans-Methyl 2-(2-trifluoromethoxyphenyl)cyclopropanecarboxylate (0.700 mg, 80% yield) was prepared from trans-methyl 2-(2-trifluoromethoxyphenyl)cyclopropanecarboxylic (commercially available) following a procedure analogous to step AB1. LC-MS (M+H)⁺ 261.1. $^1$H NMR (400 MHz, chloroform-d) δ 7.29-7.21 (m, 3H), 7.06-7.00 (m, 1H), 3.76 (s, 3H), 2.74 (ddd, J=9.3, 6.7, 4.4 Hz, 1H), 1.90 (ddd, J=8.4, 5.3, 4.4 Hz, 1H), 1.71-1.61 (m, 1H), 1.40-1.27 (m, 1H).

Step AH2

(trans-2-(2-Trifluoromethoxyphenyl)cyclopropyl)methanol (210 mg, 34% yield) was prepared from trans-methyl 2-(2-trifluoromethoxyphenyl)cyclopropanecarboxylate (from step AH1) following a procedure analogous to step AB2.

Preparation AI (±)-2-Hydrazinyl-4-(((1S,2S)-2-(2-(trifluoromethoxy)phenyl)cyclopropyl)methoxy)-3-(trifluoromethyl)pyridine

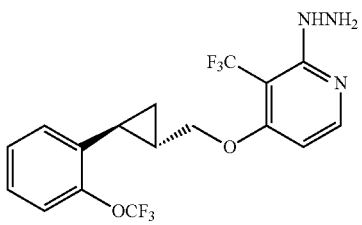 [SMILES: NNc1nccc(OC[C@H]2C[C@@H]2c2ccccc2OC(F)(F)F)c1C(F)(F)F]

(±)-2-Hydrazinyl-4-(((1S,2S)-2-(2-(trifluoromethoxy)phenyl)-cyclopropyl)methoxy)-3-(trifluoromethyl)pyridine (312 mg, 42% yield over 2 steps) was prepared from (trans-2-(2-trifluoromethoxyphenyl)-cyclopropyl)methanol (from preparation AH) following procedures analogous to steps A1 and A2. LC-MS (M+H)+ 408.1.

Preparation AJ (trans-2-(2-fluorophenyl)cyclopropyl)methanol

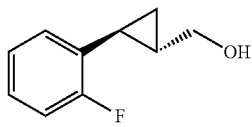 [SMILES: OC[C@H]1C[C@@H]1c1ccccc1F]

(trans-2-(2-Fluorophenyl)cyclopropyl)methanol (280 mg, 34% yield) was prepared from trans-2-(2-fluorophenyl)cyclopropanecarboxylic acid (commercially available) following the procedures analogous to step AB1 and AB2. LC-MS (M+H)+ 149.2. $^1$H NMR (500 MHz, chloroform-d) δ 7.19-7.13 (m, 1H), 7.09-7.00 (m, 2H), 6.96 (td, J=7.6, 1.5 Hz, 1H), 3.76-3.68 (m, 1H), 3.66-3.59 (m, 1H), 2.04-1.98 (m, 1H), 1.52-1.44 (m, 2H), 1.08-1.02 (m, 1H), 0.97 (dt, J=8.9, 5.2 Hz, 1H).

Preparation AK (trans-2-(2,5-Difluorophenyl)cyclopropyl)methanol

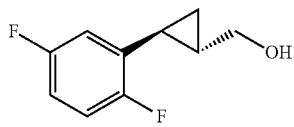 [SMILES: OC[C@H]1C[C@@H]1c1cc(F)ccc1F]

(trans-2-(2,5-Difluorophenyl)cyclopropyl)methanol was prepared from trans-2-(2,5-difluorophenyl)cyclopropanecarboxylic acid (commercially available) following the procedures analogous to step AB1 and AB2. LC-MS (M+H)+ 167.1 $^1$H NMR (500 MHz, chloroform-d) δ 6.97 (td, J=9.2, 4.7 Hz, 1H), 6.86-6.79 (m, 1H), 6.62 (ddd, J=9.2, 6.0, 3.1 Hz, 1H), 3.75-3.68 (m, 1H), 3.65-3.59 (m, 1H), 2.04-1.98 (m, 1H), 1.52 (t, J=5.0 Hz, 1H), 1.49-1.42 (m, 1H), 1.05-0.98 (m, 2H).

Preparation AL (trans-2-(4-Methoxyphenyl)cyclopropyl)methanol

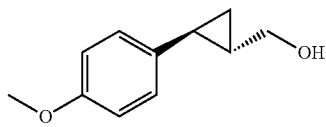

(trans-2-(4-Methoxyphenyl)cyclopropyl)methanol was prepared from trans-2-(4-methoxyphenyl)cyclopropanecarboxylic acid (commercially available) following the procedures analogous to step AB1 and AB2. LC-MS (M−H$_2$O+ H)+=161.2. $^1$H NMR (500 MHz, chloroform-d) δ 7.10-6.98 (m, 2H), 6.92-6.77 (m, 2H), 3.84-3.77 (m, 3H), 3.70-3.56 (m, 2H), 1.87-1.76 (m, 1H), 1.45-1.34 (m, 2H), 0.96-0.86 (m, 2H).

Preparation AM (1s,3s)-1-(3-Fluorophenyl)-3-(2-hydrazinyl-3-(trifluoromethyl)pyridin-4-yloxy)cyclobutanecarbonitrile

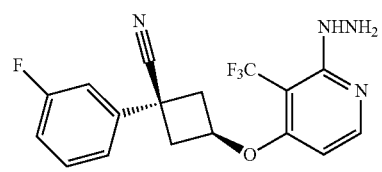 [SMILES: N#C[C@]1(c2cccc(F)c2)C[C@H](Oc2ccnc(NN)c2C(F)(F)F)C1]

Step AM1

(1s,3s)-3-(2-Chloro-3-(trifluoromethyl)pyridin-4-yloxy)-1-(3-fluorophenyl)cyclobutanecarbonitrile (298 mg, 67% yield) was prepared from (1s,3s)-1-(3-fluorophenyl)-3-hydroxycyclobutanecarbonitrile (WO 2003/063797) and 2,4-dichloro-3-(trifluoromethyl)pyridine (WO 2010/130422) following a procedure analogous to step A1. LCMS (M+H)+ 371.0. $^1$H NMR (500 MHz, chloroform-d) δ 8.37 (d, J=5.6 Hz, 1H), 7.48 (td, J=8.1, 6.0 Hz, 1H), 7.32-7.09 (m, 4H), 6.62 (d, J=5.8 Hz, 1H), 4.96 (t, J=6.6 Hz, 1H), 3.24 (d, J=6.6 Hz, 4H).

Step AM2

(1s,3s)-1-(3-Fluorophenyl)-3-(2-hydrazinyl-3-(trifluoromethyl)pyridin-4-yloxy)cyclobutanecarbonitrile (294 mg, quantitative yield) was prepared from (1s,3s)-3-(2-chloro-3-(trifluoromethyl)pyridin-4-yloxy)-1-(3-fluorophenyl)cyclobutanecarbonitrile (from step AM1) following a procedure analogous to step A2. LC-MS (M+H)+ 367.1.

Preparation AN (trans-2-(3,6-Difluoro-2-methoxyphenyl)cyclopropyl)methanol

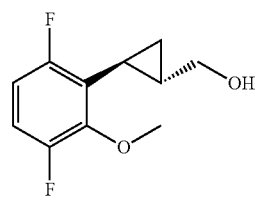

Step AN1

A 60% dispersion of sodium hydride in mineral oil (0.906 g, 37.8 mmol) was added to a chilled 0° C. solution of diethyl (2-(methoxy(methyl)amino)-2-oxoethyl)phosphonate (7.64 g, 32.0 mmol) in diethyl ether (250 mL). After 30 minutes, 3,6-difluoro-2-methoxybenzaldehyde (5.0 g, 29.0 mmol) was slowly added. The resulting mixture was allowed to warm to rt and stir for 18 h. The reaction was quenched with 1N HCl (10 mL), then poured into water. The aqueous layer was made acidic with 1N HCl and extracted with ethyl acetate. The combined organic layers were washed with brine, dried over sodium sulfate, filtered and concentrated in vacuo. The crude product mixture was purified by silica-gel column chromatography (0-50% EtOAc/hexanes) to afford (E)-3-(3,6-difluoro-2-methoxyphenyl)-N-methoxy-N-methylacrylamide (4.96 g, 66% yield). LC-MS (M+H)$^+$ 258.1.

Step AN2 trans-2-(3,6-Difluoro-2-methoxyphenyl)-N-methoxy-N-methylcyclopropanecarboxamide (2.12 g, quantitative yield) was prepared from trans-3-(3,6-difluoro-2-methoxyphenyl)-N-methoxy-N-methylacrylamide (from step AN1) following a procedure analogous to step AD2. LC-MS (M+H)$^+$ 272.1. $^1$H NMR (500 MHz, chloroform-d) δ 6.98-6.85 (m, 1H), 6.69 (td, J=9.5, 4.0 Hz, 1H), 3.94 (s, 3H), 3.77 (s, 3H), 3.27 (s, 3H), 1.71 (br. s., 1H), 1.59-1.50 (m, 2H), 0.91-0.83 (m, 1H).

Step AN3 trans-2-(3,6-difluoro-2-methoxyphenyl)cyclopropanecarboxylic acid (1.38 g, 78% yield) was prepared from trans-2-(3,6-Difluoro-2-methoxyphenyl)-N-methoxy-N-methylcyclopropanecarboxamide (from step AN2) following a procedure analogous to step AD3. $^1$H NMR (500 MHz, chloroform-d) δ 6.93 (ddd, J=10.7, 9.2, 5.1 Hz, 1H), 6.70 (td, J=9.5, 4.0 Hz, 1H), 3.98 (s, 3H), 2.62 (ddd, J=9.5, 7.1, 4.4 Hz, 1H), 2.18 (dt, J=7.8, 5.1 Hz, 1H), 1.71-1.62 (m, 2H).

Step AN4

(trans-2-(3,6-Difluoro-2-methoxyphenyl)cyclopropyl)methanol (1.15 g, 5.37 mmol, 89% yield) was prepared from trans-2-(3,6-difluoro-2-methoxyphenyl)cyclopropanecarboxylic acid (from step AN3) following a procedure and purification method analogous to step F2. LC-MS (M−H$_2$O+H)$^+$ 197.1. $^1$H NMR (500 MHz, chloroform-d) δ 6.89 (ddd, J=10.7, 9.3, 5.0 Hz, 1H), 6.68 (td, J=9.5, 4.0 Hz, 1H), 3.99 (s, 3H), 3.82 (dd, J=11.0, 6.0 Hz, 1H), 3.48 (dd, J=11.1, 7.9 Hz, 1H), 1.77-1.69 (m, 1H), 1.59 (dtd, J=8.2, 5.3, 2.4 Hz, 1H), 1.33-1.25 (m, 1H), 0.97-0.91 (m, 1H).

Preparation AO (trans-2-(2-Chloro-6-fluorophenyl)cyclopropyl)methanol

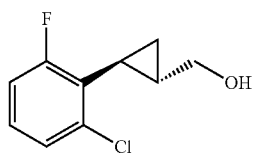 [SMILES: OC[C@H]1C[C@@H]1c1c(F)cccc1Cl]

(trans-2-(2-Chloro-6-fluorophenyl)cyclopropyl)methanol (1.12 g, 42% yield over 2 steps) was prepared from trans-2-(2-chloro-6-fluorophenyl)cyclopropanecarboxylic acid (commercially available) following procedures analogous to step AB1 and AB2. LC-MS (M−H$_2$O+H)$^+$=183.1. $^1$H NMR (500 MHz, chloroform-d) δ 7.20-7.16 (m, 1H), 7.15-7.10 (m, 1H), 6.94 (ddd, J=10.3, 8.3, 1.2 Hz, 1H), 3.77-3.69 (m, 2H), 1.75 (dt, J=9.1, 5.3 Hz, 1H), 1.62-1.57 (m, 2H), 1.22-1.16 (m, 1H), 1.04 (dtd, J=9.1, 5.4, 1.2 Hz, 1H).

Preparation AP (trans-2-(4-fluoro-2-methoxyphenyl)cyclopropyl)methanol

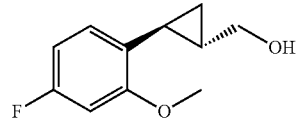

Step AP1

(E)-3-(4-fluoro-2-methoxyphenyl)-N-methoxy-N-methylacrylamide (4.96 g, 64% yield) was prepared from 4-fluoro-2-methoxybenzaldehyde (commercially available) following a procedure analogous to step AN1. LC-MS (M+H)$^+$ 240.1. $^1$H NMR (400 MHz, chloroform-d) δ 7.95 (d, J=15.8 Hz, 1H), 7.52 (dd, J=8.4, 6.7 Hz, 1H), 7.04 (d, J=15.8 Hz, 1H), 6.71-6.58 (m, 2H), 3.87 (s, 3H), 3.76 (s, 3H), 3.30 (s, 3H).

Step AP2 trans-2-(4-Fluoro-2-methoxyphenyl)-N-methoxy-N-methylcyclopropanecarboxamide (870 mg, 41% yield) was prepared from (E)-3-(4-fluoro-2-methoxyphenyl)-N-methoxy-N-methylacrylamide (from step AP1) following a procedure analogous to step AD2. LC-MS (M+H)$^+$ 254.1. $^1$H NMR (500 MHz, chloroform-d) δ 6.92 (dd, J=9.2, 6.6 Hz, 1H), 6.62-6.56 (m, 2H), 3.83 (s, 3H), 3.73 (s, 3H), 3.27 (s, 3H), 2.63 (ddd, J=9.1, 6.6, 4.5 Hz, 1H), 2.30 (br. s., 1H), 1.61-1.58 (m, 1H), 1.30-1.28 (m, 1H).

Step AP3 trans-2-(4-Fluoro-2-methoxyphenyl)cyclopropanecarboxylic acid (371 mg, 51% yield) was prepared from trans-2-(4-Fluoro-2-methoxyphenyl)-N-methoxy-N-methylcyclopropanecarboxamide (from step AP2) following a procedure analogous to step AD3. $^1$H NMR (500 MHz, chloroform-d) δ 6.89 (dd, J=7.9, 6.6 Hz, 1H), 6.65-6.54 (m, 2H), 3.86 (s, 3H), 2.72 (ddd, J=9.2, 6.8, 4.4 Hz, 1H), 1.82-1.76 (m, 1H), 1.64-1.61 (m, 1H), 1.39 (ddd, J=8.2, 6.9, 4.5 Hz, 1H).

Step AP4

(trans-2-(4-Fluoro-2-methoxyphenyl)cyclopropyl)methanol (367 mg, quantitative yield) was prepared from trans-2-(4-fluoro-2-methoxyphenyl)cyclopropanecarboxylic acid (from step AP3) following a procedure and purification method analogous to step F2. LC-MS (M−H$_2$O+H)$^+$ 179.1.

Preparation AQ (1s,3s)-1-(4-Fluorophenyl)-3-(2-hydrazinyl-3-(trifluoromethyl)pyridin-4-yloxy)cyclobutanecarbonitrile

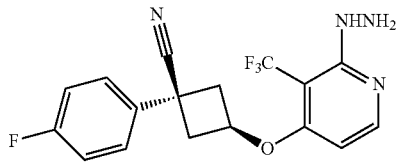 [SMILES: N#C[C@]1(c2ccc(F)cc2)C[C@H](Oc2ccnc(NN)c2C(F)(F)F)C1]

Step AQ1

(1s,3s)-3-(2-Chloro-3-(trifluoromethyl)pyridin-4-yloxy)-1-(4-fluorophenyl)cyclobutanecarbonitrile (370 mg, 20% yield) was prepared from (1s,3s)-1-(4-fluorophenyl)-3-hydroxycyclobutanecarbonitrile (4:1 trans/cis mixture, WO 2009/156100) and 2,4-dichloro-3-(trifluoromethyl)pyridine (WO 2010/130422) following a procedure analogous to step A1. LCMS (M+H)+371.0. $^1$H NMR (500 MHz, chloroform-d) δ 8.37 (d, J=5.8 Hz, 1H), 7.51-7.45 (m, 2H), 7.23-7.16 (m, 2H), 6.61 (d, J=5.8 Hz, 1H), 4.94 (t, J=6.6 Hz, 1H), 3.24 (d, J=6.6 Hz, 4H).

Step AQ2

(1s,3s)-1-(4-Fluorophenyl)-3-(2-hydrazinyl-3-(trifluoromethyl)pyridin-4-yloxy)cyclobutanecarbonitrile (368 mg, quantitative yield) was prepared from (1s,3s)-3-(2-chloro-3-(trifluoromethyl)pyridin-4-yloxy)-1-(4-fluorophenyl)cyclobutanecarbonitrile (from step AQ1) following a procedure analogous to step A2. LC-MS (M+H)+ 367.1.

Preparation AR (1-(2,4-difluorophenyl)cyclopropyl)methanol

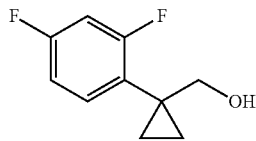 [SMILES: OCC1(c2ccc(F)cc2F)CC1]

(1-(2,4-Difluorophenyl)cyclopropyl)methanol (810 mg, 87% yield) was prepared from 1-(2,4-difluorophenyl)cyclopropanecarboxylic acid (*Angew. Chem., Int. Ed.* 2011, 50, 314) following a procedure analogous to step F2. LC-MS (M−H$_2$O+H)+ 167.1.

Preparation AS 4-(((1S,2S)-2-(4-Fluorophenyl)cyclopropyl)methoxy)-2-hydrazinyl-3-(trifluoromethyl)pyridine

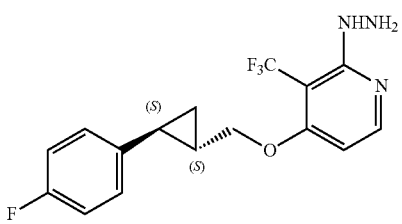

Step AS1

2-Chloro-4-(((1S,2S)-2-(4-fluorophenyl)cyclopropyl)methoxy)-3-(trifluoromethyl)pyridine (1.0, 99% yield) was prepared from ((1S,2S)-2-(4-fluorophenyl)cyclopropyl)methanol (from preparation C) and 2,4-dichloro-3-(trifluoromethyl)pyridine (WO 2010/130422) following a procedure analogous to step A1. LC-MS (M+H)+ 346.1.

Step AS2

4-(((1S,2S)-2-(4-Fluorophenyl)cyclopropyl)methoxy)-2-hydrazinyl-3-(trifluoromethyl)pyridine (342 mg, 97% yield) was prepared from 2-chloro-4-(((1S,2S)-2-(4-fluorophenyl)cyclopropyl)methoxy)-3-(trifluoromethyl)pyridine (from step AS1) following a procedure analogous to step A2. LC-MS (M+H)+ 342.1.

Preparation AT (1s,3s)-3-Hydroxy-1-(2-methoxyphenyl)cyclobutanecarbonitrile

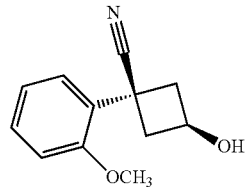 [SMILES: COc1ccccc1[C@]1(C#N)C[C@@H](O)C1]

To a solution of 2-(2-methoxyphenyl)acetonitrile (5.0 g, 34.0 mmol) in THF (100 mL) was added a solution of methyllithium (1.6 M in hexane, 21.2 mL, 34.0 mmol) dropwise and the resulting solution was stirred for 1 h at −78° C. To the solution was added 2-(bromomethyl)oxirane (2.91 mL, 34.0 mmol) in THF (50 mL) dropwise over 30 min and the reaction mixture was stirred for 1 h at −78° C. A solution of methylmagnesium bromide (3.0 M in THF, 11.3 mL, 34.0 mmol) was added into the reaction mixture and the resulting mixture was stirred for 12 h at room temperature. The reaction mixture was diluted with ethyl acetate and washed with brine. The organic layer was dried (sodium sulfate), filtered, and concentrated in vacuo. The oily residue was purified by silica gel column chromatography (0-100% ethyl acetate/hexanes) to afford (1s,3s)-3-hydroxy-1-(2-methoxyphenyl)cyclobutanecarbonitrile (4.61 g, 67% yield) as a 4:1 ((1s,3s)/(1s,3r)) mixture of diastereomers. Data for (1s,3s) isomer only: $^1$H NMR (500 MHz, chloroform-d) δ 7.39-7.29 (m, 2H), 7.02-6.95 (m, 2H), 4.34-4.26 (m, 1H), 3.94 (s, 3H), 3.10-3.03 (m, 2H), 2.86-2.79 (m, 2H).

Preparation AU (1s,3s)-3-(2-Hydrazinyl-3-(trifluoromethyl)pyridin-4-yloxy)-1-(2-methoxyphenyl)cyclobutanecarbonitrile

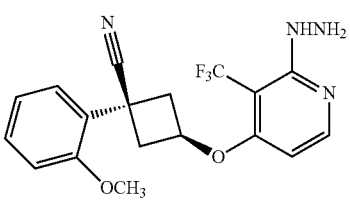 [SMILES: COc1ccccc1[C@]1(C#N)C[C@@H](Oc2ccnc(NN)c2C(F)(F)F)C1]

Step AU1

(1s,3s)-3-(2-Chloro-3-(trifluoromethyl)pyridin-4-yloxy)-1-(2-methoxyphenyl)cyclobutanecarbonitrile (856 mg, 46% yield) was prepared from (1s,3s)-3-hydroxy-1-(2-methoxyphenyl)cyclobutanecarbonitrile (from preparation AT) and 2,4-dichloro-3-(trifluoromethyl)pyridine (WO 2010/130422) following a procedure analogous to step A1. LC-MS (M+H)$^+$ 383.0. $^1$H NMR (500 MHz, chloroform-d) δ 8.32 (dd, J=5.6, 1.8 Hz, 1H), 7.43-7.37 (m, 1H), 7.33-7.27 (m, 1H), 7.06-6.98 (m, 2H), 6.60 (d, J=5.8 Hz, 1H), 4.79 (t, J=6.0 Hz, 1H), 3.94 (s, 3H), 3.32-3.24 (m, 2H), 3.18-3.10 (m, 2H).

Step AU2

(1s,3s)-3-(2-Hydrazinyl-3-(trifluoromethyl)pyridin-4-yloxy)-1-(2-methoxyphenyl)cyclobutanecarbonitrile (820 mg, 97% yield) was prepared from (1s,3s)-3-(2-Chloro-3-(trifluoromethyl)pyridin-4-yloxy)-1-(2-methoxyphenyl)cyclobutanecarbonitrile (from step AU1) following a procedure analogous to step A2. LC-MS (M+H)$^+$ 379.1.

Preparation AV (1s,3s)-1-(3,5-Difluorophenyl)-3-hydroxycyclobutanecarbonitrile

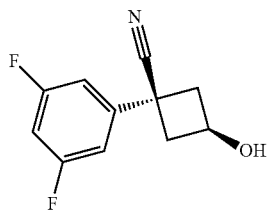 [SMILES: N#C[C@]1(c2cc(F)cc(F)c2)C[C@H](O)C1]

(1s,3s)-1-(3,5-Difluorophenyl)-3-hydroxycyclobutanecarbonitrile (3.87 g, 57% yield) was prepared from 2-(3,5-difluorophenyl)acetonitrile following a procedure analogous to preparation AT. The product was isolated as a 4:1 ((1s,3s)/(1s,3r)) mixture of diastereomers. Data for (1s,3s) isomer only: $^1$H NMR (500 MHz, chloroform-d) δ 7.02-6.99 (m, 2H), 6.85-6.80 (m, 1H), 4.57-4.47 (m, 1H), 3.02-2.90 (m, 4H), 2.18 (d, J=5.6 Hz, 1H).

Preparation AW (1s,3s)-1-(3,5-Difluorophenyl)-3-(2-hydrazinyl-3-(trifluoromethyl)pyridin-4-yloxy)cyclobutanecarbonitrile

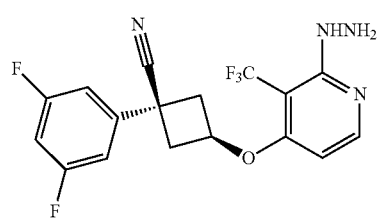 [SMILES: N#C[C@]1(c2cc(F)cc(F)c2)C[C@H](Oc2ccnc(NN)c2C(F)(F)F)C1]

Step AW1

(1s,3s)-3-(2-Chloro-3-(trifluoromethyl)pyridin-4-yloxy)-1-(3,5-difluorophenyl)cyclobutanecarbonitrile (427 mg, 23% yield) was prepared from (1s,3s)-1-(3,5-difluorophenyl)-3-hydroxycyclobutanecarbonitrile (from preparation AV) and 2,4-dichloro-3-(trifluoromethyl)pyridine (WO 2010/130422) following a procedure analogous to step A1. LCMS (M+H)+389.0.

Step AW2

(1s,3s)-1-(3,5-Difluorophenyl)-3-(2-hydrazinyl-3-(trifluoromethyl)pyridin-4-yloxy)cyclobutanecarbonitrile (405 mg, 96% yield) was prepared from (1s,3s)-3-(2-Chloro-3-(trifluoromethyl)pyridin-4-yloxy)-1-(3,5-difluorophenyl)cyclobutanecarbonitrile (from step AW1) following a procedure analogous to step A2. LC-MS (M+H)$^+$ 385.1.

Preparation AX (1-(3,5-Difluorophenyl)cyclopropyl)methanol

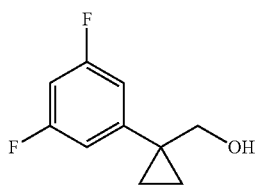 [SMILES: OCC1(c2cc(F)cc(F)c2)CC1]

(1-(3,5-Difluorophenyl)cyclopropyl)methanol (860 mg, 93% yield) was prepared from 1-(3,5-difluorophenyl)cyclopropanecarboxylic acid (commercially available) following a procedure analogous to step F2. LC-MS (M–H$_2$O+H)$^+$ 167.1.

Preparation AY 4-((1-(3,5-Difluorophenyl)cyclopropyl)methoxy)-2-hydrazinyl-3-(trifluoromethyl)pyridine

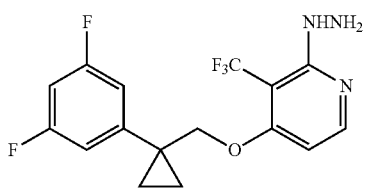 [SMILES: NNc1nccc(OCC2(c3cc(F)cc(F)c3)CC2)c1C(F)(F)F]

Step AY1

2-Chloro-4-((1-(3,5-difluorophenyl)cyclopropyl)methoxy)-3-(trifluoromethyl)pyridine (943 mg, 56% yield) was prepared from (1-(3,5-difluorophenyl)cyclopropyl)methanol (from preparation AX) and 2,4-dichloro-3-(trifluoromethyl)pyridine (WO 2010/130422) following a procedure analogous to step A1. LCMS (M+H)+364.0.

Step AY2

4-((1-(3,5-Difluorophenyl)cyclopropyl)methoxy)-2-hydrazinyl-3-(trifluoromethyl)pyridine (850 mg, 91% yield) was prepared from 2-chloro-4-((1-(3,5-difluorophenyl)cyclopropyl)methoxy)-3-(trifluoromethyl)pyridine (from step AY1) following a procedure analogous to step A2. LC-MS (M+H)+ 360.2.

Preparation AZ (1-(3,5-Dichlorophenyl)cyclopropyl)methanol

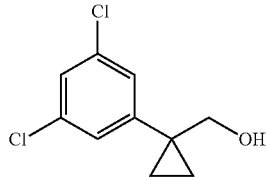 [SMILES: OCC1(c2cc(Cl)cc(Cl)c2)CC1]

(1-(3,5-Dichlorophenyl)cyclopropyl)methanol (660 mg, 70% yield) was prepared from 1-(3,5-dichlorophenyl)cyclopropanecarboxylic acid (commercially available) following a procedure analogous to step F2. LC-MS (M–H$_2$O+H)+ 199.1.

Preparation AAA 4-((1-(3,5-Dichlorophenyl)cyclopropyl)methoxy)-2-hydrazinyl-3-(trifluoromethyl)pyridine

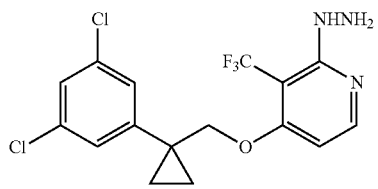 [SMILES: NNc1nccc(OCC2(c3cc(Cl)cc(Cl)c3)CC2)c1C(F)(F)F]

Step AAA1

2-Chloro-4-((1-(3,5-dichlorophenyl)cyclopropyl)methoxy)-3-(trifluoromethyl)pyridine (856 mg, 71% yield) was prepared from (1-(3,5-dichlorophenyl)cyclopropyl)methanol (from preparation AZ) and 2,4-dichloro-3-(trifluoromethyl)pyridine (WO 2010/130422) following a procedure analogous to step A1. LCMS (M+H)+ 396.0.

Step AAA2

4-((1-(3,5-Dichlorophenyl)cyclopropyl)methoxy)-2-hydrazinyl-3-(trifluoromethyl)pyridine (800 mg, 95% yield) was prepared from 2-chloro-4-((1-(3,5-dichlorophenyl)cyclopropyl)methoxy)-3-(trifluoromethyl)pyridine (from step AAA1) following a procedure analogous to step A2. LC-MS (M+H)+ 392.1.

Preparation AAB (1r,3r)-3-Phenylcyclobutanol

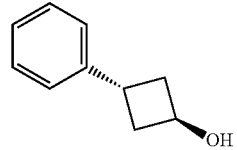 [SMILES: O[C@H]1C[C@H](c2ccccc2)C1]

Sodium borohydride (108 mg, 2.86 mmol) was added to a stirred solution of 3-phenylcyclobutanone (380 mg, 2.60 mmol) in ethanol (15 mL) maintained in a 0° C. ice bath. After 2 h, the reaction was diluted with water and the pH was adjusted to 2 by the addition of 1 N aqueous hydrochloric acid. The mixture was extracted with ethyl acetate. The combined organics were washed with brine, dried (magnesium sulfate), filtered and concentrated in vacuo to afford (1r,3r)-3-phenylcyclobutanol (423 mg, quantitative yield). The product was used without purification. $^1$H NMR was consistent with the desired product, but suggested a 2:1 (trans/cis) mixture of diastereomers. Data major diastereomer: $^1$H NMR (500 MHz, chloroform-d) δ 7.33-7.31 (m, 2H), 7.25 (d, J=7.8 Hz, 3H), 4.35-4.28 (m, 1H), 3.03-2.95 (m, 1H), 2.84-2.77 (m, 2H), 2.07-2.01 (m, 2H).

Preparation AAC

2-Hydrazinyl-4-((1r,3r)-3-phenylcyclobutoxy)-3-(trifluoromethyl)pyridine

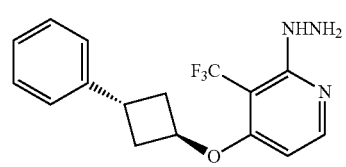 [SMILES: NNc1nccc(O[C@H]2C[C@H](c3ccccc3)C2)c1C(F)(F)F]

Step AAC1

2-Chloro-4-((1r,3r)-3-phenylcyclobutoxy)-3-(trifluoromethyl)pyridine (100 mg, 11% yield) was prepared from (1-(3,5-dichlorophenyl)cyclopropyl)methanol (from preparation AAB) and 2,4-dichloro-3-(trifluoromethyl)pyridine (WO 2010/130422) following a procedure analogous to step A1. LCMS (M+H)+ 328.2. $^1$H NMR (500 MHz, chloroform-d) δ 8.36 (d, J=5.8 Hz, 1H), 7.39-7.33 (m, 2H), 7.28-7.24 (m, 3H), 6.81 (d, J=5.8 Hz, 1H), 4.82 (quin, J=7.2 Hz, 1H), 3.31-3.22 (m, 1H), 3.06-2.97 (m, 2H), 2.41 (tdq, J=9.9, 7.5, 2.5 Hz, 2H).

Step AAC2

2-Hydrazinyl-4-((1r,3r)-3-phenylcyclobutoxy)-3-(trifluoromethyl)pyridine (103 mg, quantitative yield) was prepared from 2-chloro-4-((1r,3r)-3-phenylcyclobutoxy)-3-(trifluoromethyl)pyridine (from step AAC1) following a procedure analogous to step A2. LC-MS (M+H)+ 324.2.

Preparation AAD 3-(Cyclopropylmethyl)-8-(trifluoromethyl)-[1,2,4]
triazolo[4,3-a]pyridin-7-ol

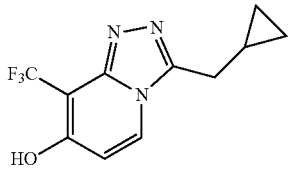 [SMILES: Oc1ccn2c(CC3CC3)nnc2c1C(F)(F)F]

Step AAD1

4-(Benzyloxy)-2-chloro-3-(trifluoromethyl)pyridine (508 mg, 72% yield) was prepared from benzylalcohol (commercially available) and 2,4-dichloro-3-(trifluoromethyl)pyridine (WO 2010/130422) following a procedure analogous to step A1. $^1$H NMR (500 MHz, chloroform-d) δ 8.33 (d, J=5.8 Hz, 1H), 7.46-7.35 (m, 5H), 6.95 (d, J=5.3 Hz, 1H), 5.27 (s, 1H).

Step AAD2

4-(Benzyloxy)-2-hydrazinyl-3-(trifluoromethyl)pyridine (500 mg, quantitative yield) was prepared from 4-(benzyloxy)-2-chloro-3-(trifluoromethyl)pyridine (from step AAD1) following a procedure analogous to step A2. LC-MS (M+H)$^+$ 284.0.

Step AAD3

7-(Benzyloxy)-3-(cyclopropylmethyl)-8-(trifluoromethyl)-[1,2,4]triazolo[4,3-a]pyridine (205 mg, 33% yield over 2 steps) was prepared from 4-(benzyloxy)-2-hydrazinyl-3-(trifluoromethyl)pyridine (from step AAD2) following procedures analogous to steps 1A and 1B of example 1. The final product was purified by silica gel column chromatography (100% EtOAc). LC-MS (M+H)$^+$ 348.2. $^1$H NMR (400 MHz, methanol-d$_4$) δ 8.97 (d, J=7.8 Hz, 1H), 7.75 (d, J=7.8 Hz, 1H), 7.58-7.50 (m, 2H), 7.50-7.37 (m, 3H), 5.66 (s, 2H), 3.14 (d, J=6.8 Hz, 2H), 1.41-1.25 (m, 1H), 0.75-0.68 (m, 2H), 0.42 (q, J=4.9 Hz, 2H).

Step AAD4

A mixture of 5% palladium-on-charcoal (23 mg, 7-(benzyloxy)-3-(cyclopropylmethyl)-8-(trifluoromethyl)-[1,2,4]triazolo[4,3-a]pyridine (from step AAD3, 203 mg, 0.58 mmol), and methanol (15 mL) was subjected to a balloon hydrogenation for 21 days. The hydrogen atmosphere was removed under vacuum and the catalyst was filtered off and washed with dichloromethane. The filtrate was concentrated in vacuo. The residue was purified using silica gel column chromatography (5% methanol/ethyl acetate) to afford 3-(cyclopropylmethyl)-8-(trifluoromethyl)-[1,2,4]triazolo[4,3-a]pyridin-7-ol (104 mg, 69% yield) as a white solid. LC-MS (M+H)$^+$ 258.1. $^1$H NMR (500 MHz, Methanol-d$_4$) δ 8.18 (d, J=7.8 Hz, 1H), 6.56 (d, J=7.8 Hz, 1H), 2.94 (d, J=6.9 Hz, 2H), 1.30-1.18 (m, 1H), 0.72-0.62 (m, 2H), 0.42-0.31 (m, 2H).

Preparation AAE (trans-2-(4-fluorophenyl)cyclopropyl)methanol

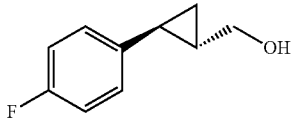 [SMILES: OC[C@H]1C[C@@H]1c1ccc(F)cc1]

Step AAE1 trans-Methyl 2-(4-fluorophenyl)cyclopropanecarboxylate (167 mg, 97% yield) was prepared from trans-2-(4-fluorophenyl)cyclopropanecarboxylic acid (commercially available) following a procedure analogous to step AB1. $^1$H NMR (500 MHz, chloroform-d) δ 7.11-7.06 (m, 2H), 7.01-6.95 (m, 2H), 3.74 (s, 3H), 2.53 (ddd, J=9.3, 6.4, 4.1 Hz, 1H), 1.87 (ddd, J=8.4, 5.2, 4.2 Hz, 1H), 1.64-1.58 (m, 1H), 1.32-1.25 (m, 2H).

Step AAE2

(trans-2-(4-fluorophenyl)cyclopropyl)methanol (119 mg, 83% yield) was prepared from trans-methyl 2-(4-fluorophenyl)cyclopropanecarboxylate (from step AAE1) following a procedure analogous to step AB2. $^1$H NMR (500 MHz, chloroform-d) δ 7.10-7.01 (m, 2H), 6.98-6.93 (m, 2H), 3.63 (d, J=6.7 Hz, 2H), 1.86-1.80 (m, 1H), 1.68 (br. s., 1H), 1.45-1.37 (m, 1H), 0.97-0.85 (m, 3H).

Preparation AAF (±)-4-(((1S,2S)-2-(4-fluorophenyl)cyclopropyl)
methoxy)-2-hydrazinyl-3-(trifluoromethyl)pyridine

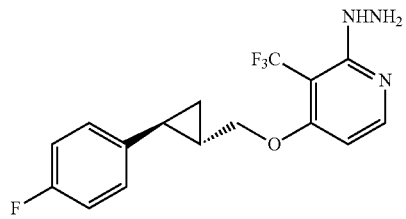 [SMILES: NNc1nccc(OC[C@H]2C[C@@H]2c2ccc(F)cc2)c1C(F)(F)F]

Step AAF1

(±)-2-chloro-4-(((1S,2S)-2-(4-fluorophenyl)cyclopropyl)methoxy)-3-(trifluoromethyl)pyridine (183 mg, 76% yield) was prepared from (trans-2-(4-fluorophenyl)cyclopropyl)methanol (from preparation AAE) and 2,4-dichloro-3-(trifluoromethyl)pyridine (WO 2010/130422) following a procedure analogous to step A1. $^1$H NMR (500 MHz, chloroform-d) δ 8.34 (d, J=5.8 Hz, 1H), 7.12-7.07 (m, 2H), 7.01-6.94 (m, 2H), 6.88 (d, J=5.8 Hz, 1H), 4.26 (dd, J=9.9, 6.0 Hz, 1H), 4.07 (dd, J=9.8, 6.9 Hz, 1H), 1.57-1.49 (m, 1H), 1.16-1.06 (m, 2H), 0.96-0.83 (m, 1H).

Step AAF2

(±)-4-(((1S,2S)-2-(4-fluorophenyl)cyclopropyl)methoxy)-2-hydrazinyl-3-(trifluoromethyl)pyridine (181 mg, quantitative yield) was prepared from (±)-2-chloro-4-(((1S,2S)-2-(4-fluorophenyl)cyclopropyl)methoxy)-3-(trifluoromethyl)pyridine (from step AAF1) following a procedure analogous to step A2. LC-MS (M+H)⁺ 342.1. ¹H NMR (500 MHz, Methanol-d₄) δ 8.19-8.16 (m, 1H), 7.17-7.13 (m, 2H), 6.98 (s, 2H), 6.59-6.53 (m, 1H), 4.29-4.23 (m, 1H), 4.10-4.03 (m, 1H), 1.55-1.46 (m, 1H), 1.11-1.04 (m, 2H), ¹⁹F NMR m-56.19, -119.87.

Preparation AAG 4-(2-Chloro-6-fluorophenethoxy)-2-hydrazinyl-3-(trifluoromethyl)pyridine

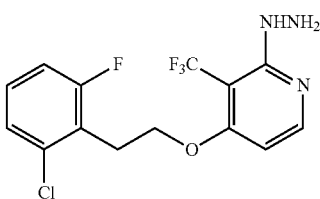 [SMILES: NNc1nccc(OCCc2c(F)cccc2Cl)c1C(F)(F)F]

Step AAG1

2-Chloro-4-(2-chloro-6-fluorophenethoxy)-3-(trifluoromethyl)pyridine (241 mg, 58% yield) was prepared from 2-(2-chloro-6-fluorophenyl)ethanol (commercially available) and 2,4-dichloro-3-(trifluoromethyl)pyridine (WO 2010/130422) following a procedure analogous to step A1. LC-MS (M+H)⁺ 355.8.

Step AAG2

4-(2-Chloro-6-fluorophenethoxy)-2-hydrazinyl-3-(trifluoromethyl)pyridine (142 mg, 68% yield) was prepared from 2-chloro-4-(2-chloro-6-fluorophenethoxy)-3-(trifluoromethyl)pyridine (from step AAF1) following a procedure analogous to step A2. LC-MS (M+H)⁺ 350.0.

Preparation AAH 2-(2,6-Difluorophenyl)ethanol

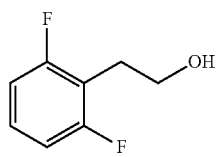 [SMILES: OCCc1c(F)cccc1F]

Step AAH1

Methyl 2-(2,6-difluorophenyl)acetate (331 g, 60% yield) was prepared from 2-(2,6-difluorophenyl)acetic acid (commercially available) following a procedure analogous to step AB1. ¹H NMR (500 MHz, chloroform-d) δ 7.30-7.20 (m, 1H), 6.95-6.87 (m, 2H), 3.77-3.71 (m, 5H).

Step AAH2

2-(2,6-Difluorophenyl)ethanol (165 mg, 59% yield) was prepared from methyl methyl 2-(2,6-difluorophenyl)acetate (from step AAH1) following a procedure analogous to step AB2. ¹H NMR (400 MHz, chloroform-d) δ 7.14 (tt, J=8.4, 6.4 Hz, 1H), 6.88-6.78 (m, 2H), 3.78 (t, J=6.1 Hz, 2H), 2.92 (t, J=6.9 Hz, 2H), 2.34 (br. s., 1H).

Preparation AAI 4-(2,6-Difluorophenethoxy)-2-hydrazinyl-3-(trifluoromethyl)pyridine

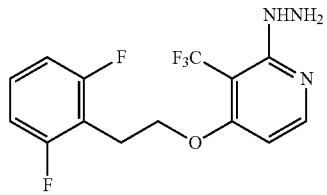 [SMILES: NNc1nccc(OCCc2c(F)cccc2F)c1C(F)(F)F]

Step AAI1

2-Chloro-4-(2,6-difluorophenethoxy)-3-(trifluoromethyl)pyridine (243 mg, 69% yield) was prepared from 2-(2,6-difluorophenyl)ethanol (from preparation AAH) and 2,4-dichloro-3-(trifluoromethyl)pyridine (WO 2010/130422) following a procedure analogous to step A1. LC-MS (M+H)⁺ 338.02. ¹H NMR (500 MHz, chloroform-d) δ 8.34 (d, J=5.8 Hz, 1H), 7.28-7.18 (m, 1H), 6.96-6.84 (m, 3H), 4.33 (t, J=6.8 Hz, 2H), 3.29-3.22 (m, 2H).

Step AAI2

4-(2,6-Difluorophenethoxy)-2-hydrazinyl-3-(trifluoromethyl)pyridine (230 mg, 96% yield) was prepared from 2-chloro-4-(2,6-difluorophenethoxy)-3-(trifluoromethyl)pyridine (from step AAI1) following a procedure analogous to step A2. LC-MS (M+H)⁺ 334.1. ¹H NMR (500 MHz, chloroform-d) δ 8.15 (d, J=6.0 Hz, 1H), 7.26-7.16 (m, 1H), 6.94-6.85 (m, 2H), 6.52 (d, J=2.0 Hz, 1H), 6.34 (d, J=5.8 Hz, 1H), 4.26 (t, J=6.9 Hz, 2H), 4.01 (br. s., 2H), 3.21 (t, J=6.9 Hz, 2H).

Preparation AAJ 2,2-Difluoro-2-phenylethanol

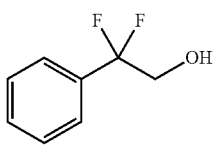 [SMILES: OCC(F)(F)c1ccccc1]

Step AAJ1

2,2-difluoro-2-phenylethanol (179 mg, 66% yield) was prepared from ethyl 2,2-difluoro-2-phenylacetate (commercially available) following a procedure analogous to step AB2. ¹H NMR (400 MHz, chloroform-d) δ 7.58-7.36 (m, 5H), 3.98 (td, J=13.4, 6.0 Hz, 2H), 2.14 (t, J=6.4 Hz, 1H).

Preparation AAK 4-(2,2-Difluoro-2-phenylethoxy)-2-hydrazinyl-3-(trifluoromethyl)pyridine

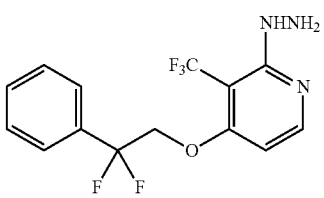 [SMILES: NNc1nccc(OCC(F)(F)c2ccccc2)c1C(F)(F)F]

Step AAK1

2-Chloro-4-(2,2-difluoro-2-phenylethoxy)-3-(trifluoromethyl)pyridine (221 mg, 58% yield) was prepared from 2,2-difluoro-2-phenylethanol (from preparation AAJ) and 2,4-dichloro-3-(trifluoromethyl)pyridine (WO 2010/130422) following a procedure analogous to step A1. ¹H NMR (500 MHz, chloroform-d) δ 8.37 (d, J=5.8 Hz, 1H), 7.62-7.55 (m, 2H), 7.54-7.45 (m, 3H), 6.85 (d, J=5.8 Hz, 1H), 4.49 (t, J=11.1 Hz, 2H).

Step AAK2

4-(2,2-Difluoro-2-phenylethoxy)-2-hydrazinyl-3-(trifluoromethyl)pyridine (186 mg, 86% yield) was prepared from 2-chloro-4-(2,2-difluoro-2-phenylethoxy)-3-(trifluoromethyl)pyridine (from step AAI1) following a procedure analogous to step A2. ¹H NMR (500 MHz, chloroform-d) δ 8.23-8.12 (m, 1H), 7.62-7.43 (m, 5H), 6.54 (br s, 1H), 6.28 (d, J=6.0 Hz, 1H), 4.43 (t, J=11.1 Hz, 2H), 3.99 (t, J=13.4 Hz, 2H).

Preparation AAL

2-Fluoro-2-phenylethanol

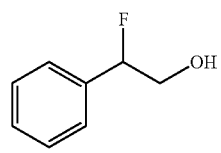

Step AAJ1

2,2-difluoro-2-phenylethanol (371 mg, 73% yield) was prepared from methyl 2-fluoro-2-phenylacetate (commercially available) following a procedure analogous to step AB2. ¹H NMR (500 MHz, chloroform-d) δ 7.45-7.24 (m, 1H), 5.65-5.51 (m, 1H), 4.01-3.78 (m, 3H), 2.26 (dd, J=8.4, 4.6 Hz, 1H).

Preparation AAM 4-(2-Fluoro-2-phenylethoxy)-2-hydrazinyl-3-(trifluoromethyl)pyridine

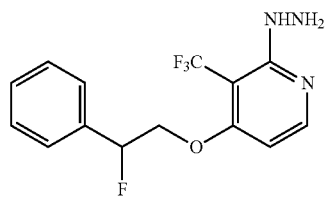 [SMILES: NNc1nccc(OCC(F)c2ccccc2)c1C(F)(F)F]

Step AAM1

2-Chloro-4-(2-fluoro-2-phenylethoxy)-3-(trifluoromethyl)pyridine (174 mg, 78% yield) was prepared from 2-fluoro-2-phenylethanol (from preparation AAL) and 2,4-dichloro-3-(trifluoromethyl)pyridine (WO 2010/130422) following a procedure analogous to step A1. ¹H NMR (500 MHz, chloroform-d) δ 8.37 (d, J=5.8 Hz, 1H), 7.50-7.39 (m, 6H), 6.92-6.85 (m, 1H), 5.95-5.81 (m, 1H), 4.47 (ddd, J=16.9, 10.7, 7.3 Hz, 1H), 4.39-4.25 (m, 1H).

Step AAM2

4-(2-Fluoro-2-phenylethoxy)-2-hydrazinyl-3-(trifluoromethyl)pyridine (172 mg, quantitative yield) was prepared from 2-chloro-4-(2-fluoro-2-phenylethoxy)-3-(trifluoromethyl)pyridine (from step AAM1) following a procedure analogous to step A2. ¹H NMR (500 MHz, Methanol-d₄) δ 8.18 (d, J=6.0 Hz, 1H), 7.50-7.37 (m, 5H), 6.58-6.53 (m, 1H), 5.90-5.75 (m, 1H), 4.52-4.34 (m, 2H).

Preparation AAN (1s,4s)-1-(4-fluorophenyl)cyclohexane-1,4-diol

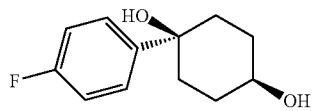

Step AAN1

1M Aqueous hydrochloric acid (7.5 mL, 7.50 mmol) was added to a solution of 8-(4-fluorophenyl)-1,4-dioxaspiro[4.5]decan-8-ol (2.0 g, 7.93 mmol, J. Am. Chem. Soc. 2012, 134, 17023) in acetone (20 mL). The mixture was left to stir at rt for 24 h. The reaction mixture was carefully quenched with aqueous sodium bicarbonate solution. The mixture was concentrated in vacuo to remove the acetone. The aqueous concentrate was extracted with ethyl acetate. The combined organic layers were washed with brine, dried over magnesium sulfate, filter and concentrated in vacuo. The residue was dissolved in minimal dichloromethane and loaded onto a prepacked silica cartridge (80 g). The crude product was purified using silica gel column chromatography (2:1 hexanes/ethyl acetate) to afford 4-(4-fluorophenyl)-4-hydroxycyclohexanone (1.3 g, 6.24 mmol, 79% yield) as a white solid. ¹H NMR (500 MHz, CHLOROFORM-d) δ 7.55-7.46 (m, 2H), 7.11-7.03 (m, 2H), 2.92 (td, J=14.0, 6.4 Hz, 2H), 2.43-2.34 (m, 2H), 2.34-2.23 (m, 2H), 2.23-2.13 (m, 2H).

Step AAN2

Sodium borohydride (0.590 g, 15.61 mmol) was added to a stirred solution of 4-(4-fluorophenyl)-4-hydroxycyclohexanone (1.3 g, 6.24 mmol) in ethanol (50 mL) maintained in a 0° C. ice bath. After 2 h, the reaction was diluted with water and the pH was adjusted to 2 by the addition of 1 N aqueous hydrochloric acid. The mixture was poured into water and extracted with ethyl acetate. The combined organics were washed with brine, dried (magnesium sulfate), filtered and concentrated in vacuo to afford (1s,4s)-1-(4-fluorophenyl)cyclohexane-1,4-diol (1.18 g, 5.61 mmol, 90% yield). ¹H NMR integration was consistent with the desired product as a >10:1 ratio of diasteromers (cis/trans). Data for cis isomer: ¹H NMR (500 MHz, DMSO-d₆) δ 7.53-7.45 (m, 2H), 7.12-7.05 (m, 2H), 4.76 (s, 1H), 4.47 (d, J=4.6 Hz, 1H), 3.47 (tq, J=9.6, 4.7 Hz, 1H), 1.78-1.55 (m, 8H).

Preparation AAO (1s,4s)-1-(4-Fluorophenyl)-4-(2-hydrazinyl-3-(trifluoromethyl)pyridin-4-yloxy)cyclohexanol

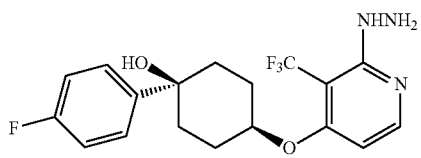 [SMILES: NNc1nccc(O[C@H]2CC[C@](O)(c3ccc(F)cc3)CC2)c1C(F)(F)F]

Step AAO1

(1s,4s)-4-(2-Chloro-3-(trifluoromethyl)pyridin-4-yloxy)-1-(4-fluorophenyl)cyclohexanol (1.21 g, 62% yield) was prepared from (1s,4s)-1-(4-fluorophenyl)cyclohexane-1,4-diol (from preparation AAN) and 2,4-dichloro-3-(trifluoromethyl)pyridine (WO 2010/130422) following a procedure analogous to step A1. The crude product was purified using silica gel column chromatography (hexanes/ethyl acetate, 3:1-1:1). LC-MS (M+H)⁺ 390.2. ¹H NMR (500 MHz, DMSO-d₆) δ 8.46 (d, J=6.0 Hz, 1H), 7.57-7.45 (m, 3H), 7.22-7.09 (m, 2H), 5.05 (s, 1H), 4.89-4.74 (m, 1H), 2.00-1.88 (m, 6H), 1.78-1.67 (m, 2H).

Step AAO2

(1s,4s)-1-(4-Fluorophenyl)-4-((2-hydrazinyl-3-(trifluoromethyl)pyridin-4-yl)oxy)cyclohexanol (255 mg, 96% yield) was prepared from (1s,4s)-4-(2-chloro-3-(trifluoromethyl)pyridin-4-yloxy)-1-(4-fluorophenyl)cyclohexanol (from step AAO1) following a procedure analogous to step A2. LC-MS (M+H)⁺ 386.2.

Preparation AAP (1r,3r)-3-(4-Fluorophenyl)cyclobutanol

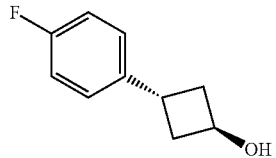 [SMILES: O[C@H]1C[C@H](c2ccc(F)cc2)C1]

Sodium borohydride (0.253 g, 6.70 mmol) was added to a stirred solution of 3-(4-fluorophenyl)cyclobutanone (1.0 g, 6.09 mmol) in ethanol (40 mL) maintained in a 0° C. ice bath. After 2 h, the reaction was diluted with water and the pH was adjusted to 2 by the addition of 1 N aqueous hydrochloric acid. The mixture was extracted with ethyl acetate. The combined organics were washed with brine, dried (magnesium sulfate), filtered and concentrated in vacuo to afford (1r,3r)-3-(4-fluorophenyl)cyclobutanol (1.12 g, quantitative yield). The product was used without purification. ¹H NMR integration suggested a 6:1 mixture of diastereomers (trans/cis). Data for trans isomer: ¹H NMR (500 MHz, CHLOROFORM-d) δ 7.21-7.17 (m, 2H), 7.02-6.98 (m, 2H), 4.34-4.27 (m, 1H), 3.00-2.91 (m, 1H), 2.82-2.75 (m, 2H), 2.07 (d, J=2.0 Hz, 1H), 2.02-1.97 (m, 2H).

Preparation AAQ 4-((1r,3r)-3-(4-Fluorophenyl)cyclobutoxy)-2-hydrazinyl-3-(trifluoromethyl)pyridine

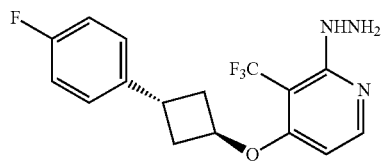 [SMILES: NNc1nccc(O[C@H]2C[C@H](c3ccc(F)cc3)C2)c1C(F)(F)F]

Step AAQ1

2-Chloro-4-((1r,3r)-3-(4-fluorophenyl)cyclobutoxy)-3-(trifluoromethyl)pyridine (1.22 g, 59% yield) was prepared from (1r,3r)-3-(4-fluorophenyl)cyclobutanol (from preparation AAP) and 2,4-dichloro-3-(trifluoromethyl)pyridine (WO 2010/130422) following a procedure analogous to step A1. LC-MS (M+H)⁺=346.1. ¹H NMR (500 MHz, chlforoform-d) δ 8.35 (d, J=5.8 Hz, 1H), 7.24-7.19 (m, 2H), 7.07-7.01 (m, 2H), 6.79 (d, J=5.8 Hz, 1H), 4.80 (t, J=7.1 Hz, 1H), 3.28-3.19 (m, 1H), 3.04-3.00 (m, 2H), 2.39-2.32 (m, 2H).

Step AAQ2

4-((1r,3r)-3-(4-Fluorophenyl)cyclobutoxy)-2-hydrazinyl-3-(trifluoromethyl)pyridine (486 mg, quantitative yield) was prepared from 2-chloro-4-((1r,3r)-3-(4-fluorophenyl)cyclobutoxy)-3-(trifluoromethyl)pyridine (from step AAQ1) following a procedure analogous to step A2. LC-MS (M+H)⁺ 345.1.

Preparation AAR 4-((1s,4s)-4-(4-Fluorophenyl)-4-(methoxy-d₃)cyclohexyloxy)-2-hydrazinyl-3-(trifluoromethyl)pyridine

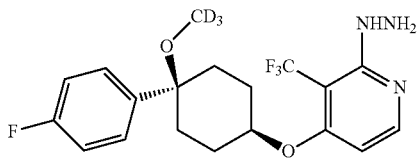 [SMILES: [2H]C([2H])([2H])O[C@]1(c2ccc(F)cc2)CC[C@H](Oc2ccnc(NN)c2C(F)(F)F)CC1]

Step AAR1

A solution of (1s,4s)-4-(2-Chloro-3-(trifluoromethyl)pyridin-4-yloxy)-1-(4-fluorophenyl)cyclohexanol (1s,4s)-4-((2-chloro-3-(trifluoromethyl)pyridin-4-yl)oxy)-1-(4-fluorophenyl)cyclohexanol (250 mg, 0.641 mmol, from step AAO1) in DMF (2 mL) was added to a stirred mixture of sodium hydride 60% dispersion in mineral oil (51.3 mg, 1.283 mmol) and DMF (5 mL) maintained at 0° C. After 30 min, a solution of iodomethane-d₃ (232 mg, 1.604 mmol) in DMF (1 mL) was added. The resulting mixture was allowed to stir for 2 h at 0° C. The crude reaction was carefully quenched was water. The mixture was poured into water and extracted with ethyl acetate. The combined organics were washed with brine, dried over magnesium sulfate, filtered and concentrated in vacuo to afford 2-chloro-4-(((1s,4s)-4-(4-fluorophenyl)-4-(methoxy-d₃)cyclohexyl)oxy)-3-(trifluoromethyl)pyridine. No purification was conducted. LC-MS (M+H)⁺ 407.2.

Step AAR2

A mixture of 4-(((1s,4s)-4-(4-fluorophenyl)-4-(methoxy-d₃)cyclohexyl)oxy)-2-hydrazinyl-3-(trifluoromethyl)pyridine (261 mg, 0.641 mmol), dioxane (50 mL), and hydrazine monohydrate (0.243 mL, 3.21 mmol) was heated together in a sealed vial in an oil bath at 95° C. for 12 h. The reaction mixture was concentrated in vacuo. The residue was partitioned between aqueous sodium bicarbonate and ethyl acetate. The aqueous layer was extracted with ethyl acetate. The combined organic extracts were washed with brine, dried over magnesium sulfate, filtered, and concentrated in vacuo to afford 4-(((1s,4s)-4-(4-fluorophenyl)-4-(methoxy-d₃)cyclohexyl)oxy)-2-hydrazinyl-3-(trifluoromethyl)pyridine (275 mg, quantitative % yield). LC-MS (M+H)⁺ 403.2.

Example 1

3-(Cyclopropylmethyl)-7-((1-phenylcyclohexyl)methoxy)-8-(trifluoromethyl)-[1,2,4]triazolo[4,3-a]pyridine

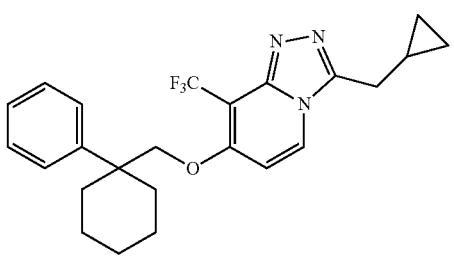 [SMILES: FC(F)(F)c1c(OCC2(c3ccccc3)CCCCC2)ccn2c(CC3CC3)nnc12]

Step 1A

A 1.0 M solution of 2-cyclopropylacetyl chloride in DCM (0.55 mL, 0.55 mmol) was added to a flask charged with a solution of 2-hydrazinyl-4-((1-phenylcyclohexyl)methoxy)-3-(trifluoromethyl)pyridine (from preparation A, 200 mg, 0.547 mmol) and triethylamine (0.114 mL, 0.821 mmol) in DCM (5 mL) at 0° C. After 1 h at 0° C., the reaction was diluted with water. The aqueous mixture was extracted with DCM. The organic extracts were washed with brine, dried (sodium sulfate), filtered, and concentrated in vacuo to afford 2-cyclopropyl-N'-(4-((1-phenylcyclohexyl)methoxy)-3-(trifluoromethyl)pyridin-2-yl)acetohydrazide (245 mg, quantitative yield). The crude product was carried forward without purification. LC-MS (M+H)⁺ 480.0.

Step 1B

A mixture of 2-cyclopropyl-N'-(4-((1-phenylcyclohexyl)methoxy)-3-(trifluoromethyl)pyridin-2-yl)acetohydrazide (from step 1A, 245 mg, 0.547 mmol), Burgess reagent (130 mg, 0.547 mmol), acetonitrile (2 mL), and dioxane (2 mL) was heated at 85° C. in a sealed vial for 18 h. After cooling to rt, the reaction mixture was evaporated in vacuo and the residue was partitioned between water and ethyl acetate. The aqueous layer was extracted with ethyl acetate, and the combined organic layers were washed with brine, dried over magnesium sulfate, filtered and concentrated in vacuo. The crude product was dissolved in a minimum amount of boiling ethyl acetate. The solution was allowed to cool to rt. After 3 h, the crystalline solid was collected by vacuum filtration to afford 3-(cyclopropylmethyl)-7-((1-phenylcyclohexyl)methoxy)-8-(trifluoromethyl)-[1,2,4]triazolo[4,3-a]pyridine (107 mg, 45% yield) as a white solid.

Example 2

7-(2-(4-Chlorophenyl)-2-methylpropoxy)-3-(cyclopropylmethyl)-8-(trifluoromethyl)-[1,2,4]triazolo[4,3-a]pyridine

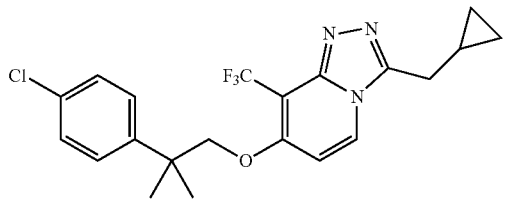 [SMILES: CC(C)(COc1ccn2c(CC3CC3)nnc2c1C(F)(F)F)c1ccc(Cl)cc1]

The titled compound (157 mg, 65% yield over 2 steps) was prepared from 4-(2-(4-chlorophenyl)-2-methylpropoxy)-2-hydrazinyl-3-(trifluoromethyl)pyridine (from preparation B, 200 mg, 0.556 mmol) following procedures analogous to steps 1A and 1B. The final product was purified by silica gel column chromatography (100% EtOAc).

Example 3

3-(Cyclopropylmethyl)-7-(((1S,2S)-2-(4-fluorophenyl)cyclopropyl)methoxy)-[1,2,4]triazolo[4,3-a]pyridine-8-carbonitrile

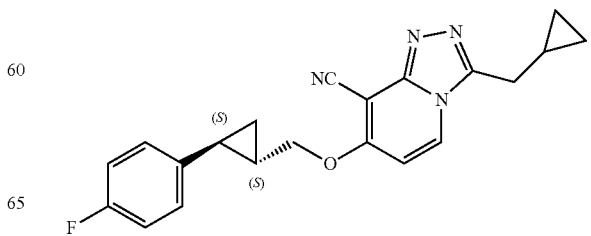

Step 3A

N'-(3-cyano-4-(((1S,2S)-2-(4-fluorophenyl)cyclopropyl)methoxy)pyridin-2-yl)-2-cyclopropylacetohydrazide (111 mg, quantitative yield) was prepared from 4-(((1S,2S)-2-(4-fluorophenyl)cyclopropyl)methoxy)-2-hydrazinylnicotinonitrile (from preparation D, 87 mg, 0.292 mmol) following a procedure analogous to step 1A. The crude product was carried forward without purification. LC-MS (M+Na)+ 381.2.

Step 3B

A mixture of N'-(3-cyano-4-(((1S,2S)-2-(4-fluorophenyl)cyclopropyl)methoxy)pyridin-2-yl)-2-cyclopropylacetohydrazide (from step 3A, 111 mg, 0.292 mmol), Burgess reagent (174 mg, 0.730 mmol), acetonitrile (2 mL), and dioxane (2 mL) was heated in a sealed vial in an oil bath at 110° C. for 4 h. The mixture was cooled to rt. The resulting precipitate was collected using vacuum filtration. The solid was rinsed with fresh dioxane (5 mL). The white solid was dried under vacuum to afford 3-(cyclopropylmethyl)-7-(((1S,2S)-2-(4-fluorophenyl)cyclopropyl)methoxy)-[1,2,4]triazolo[4,3-a]pyridine-8-carbonitrile (48 mg, 45% yield).

Example 4

3-(Cyclopropylmethyl)-7-(2-(4-fluorophenyl)propoxy)-8-(trifluoromethyl)-[1,2,4]triazolo[4,3-a]pyridine, TFA salt

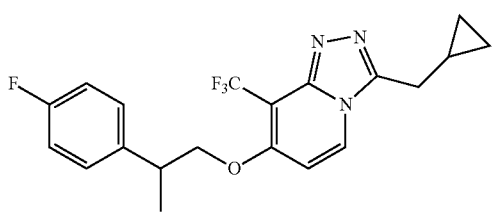 [SMILES: CC(COc1ccn2c(CC3CC3)nnc2c1C(F)(F)F)c1ccc(F)cc1]

A solution of 2-(4-fluorophenyl)propan-1-ol (from preparation E, 69.9 mg, 0.453 mmol) in toluene (0.5 mL) was added to a microwave vial charged with 7-chloro-3-(cyclopropylmethyl)-8-(trifluoromethyl)-[1,2,4]triazolo[4,3-a]pyridine [(from J. Med Chem. 2012, 55, 8770), 25 mg, 0.091 mmol], cesium carbonate (59.1 mg, 0.181 mmol), (S)—(R)-JOSIPHOS (11 mg, 0.018 mmol), and allylpalladium chloride dimer (3.3 mg, 9.1 μmol). The vessel was flushed with nitrogen then sealed with a teflon coated cap. The mixture was heated at 135° C. for 2 h. The reaction was cooled to rt. The crude reaction mixture was purified by silica gel column chromatography (100% EtOAc) and was further purified using reverse phase preparatory HPLC.

Example 5

7-(2-(2-Chloro-6-fluorophenyl)propoxy)-3-(cyclopropylmethyl)-8-(trifluoromethyl)-[1,2,4]triazolo[4,3-a]pyridine

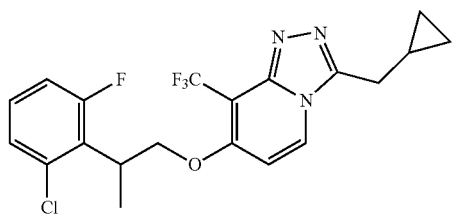 [SMILES: CC(COc1ccn2c(CC3CC3)nnc2c1C(F)(F)F)c1c(F)cccc1Cl]

The titled compound (240 mg, 69% yield over 2 steps) was prepared from 4-(2-(2-chloro-6-fluorophenyl)propoxy)-2-hydrazinyl-3-(trifluoromethyl)pyridine (from preparation G) following procedures analogous to steps 1A and 1B. The final product was purified using silica gel column chromatography (100% EtOAc).

Example 6

3-(Cyclopropylmethyl)-7-(2-(4-fluorophenyl)-2-methylpropoxy)-8-(trifluoromethyl)-[1,2,4]triazolo[4,3-a]pyridine

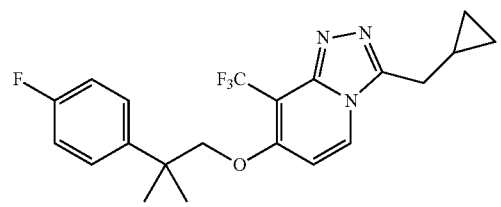 [SMILES: CC(C)(COc1ccn2c(CC3CC3)nnc2c1C(F)(F)F)c1ccc(F)cc1]

The titled compound (13 mg, 13% yield) was prepared from 2-(4-fluorophenyl)-2-methylpropan-1-ol (preparation H) and 7-chloro-3-(cyclopropylmethyl)-8-(trifluoromethyl)-[1,2,4]triazolo[4,3-a]pyridine (from J. Med Chem. 2012, 55, 8770) following procedures analogous to example 4. The final product was purified using preparative LC/MS (column: XBridge C18, 19×mm, 5-μm particles; mobile phase A: 5:95 acetonitrile/water with 10-mM ammonium acetate; mobile phase B: 95:5 acetonitrile/water with 10-mM ammonium acetate; gradient: 30-70% B over 15 minutes, then a 7-minute hold at 100% B; flow: 20 mL/min).

Example 7

7-(2-(4-Chlorophenyl)-2-methylpropoxy)-3-(2,2,2-trifluoroethyl)-8-(trifluoromethyl)-[1,2,4]triazolo[4,3-a]pyridine

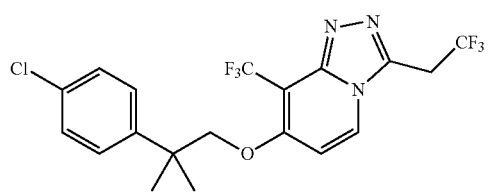 [SMILES: CC(C)(COc1ccn2c(CC(F)(F)F)nnc2c1C(F)(F)F)c1ccc(Cl)cc1]

The titled compound (48 mg, 17% yield) was prepared from 4-(2-(4-chlorophenyl)-2-methylpropoxy)-2-hydrazinyl-3-(trifluoromethyl)pyridine (from preparation B) and 3,3,3-trifluoropropanoyl chloride (commercially available) following procedures analogous to steps 1A and 1B. The final product was purified using silica gel column chromatography (1:1 hexane/ethyl acetate) and was recrystallized from ethyl acetate/hexanes.

Example 8

3-(Cyclopropylmethyl)-7-(2-(4-fluorophenoxy)-2-methylpropoxy)-8-(trifluoromethyl)-[1,2,4]triazolo[4,3-a]pyridine

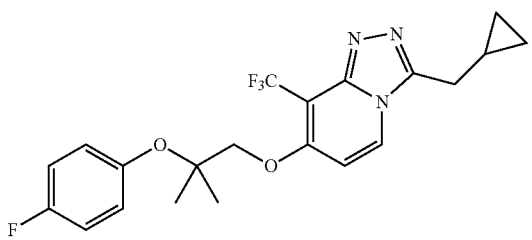 [SMILES: CC(C)(COc1ccn2c(CC3CC3)nnc2c1C(F)(F)F)Oc1ccc(F)cc1]

The titled compound (220 mg, 76% yield over 2 steps) was prepared from 4-(2-(4-fluorophenoxy)-2-methylpropoxy)-2-hydrazinyl-3-(trifluoromethyl)pyridine (from preparation J) following procedures analogous to steps 1A and 1B. The final product was purified using silica gel column chromatography (100% EtOAc).

Examples 9 and 10

(R)-7-(2-(2-chloro-6-fluorophenyl)propoxy)-3-(cyclopropylmethyl)-8-(trifluoromethyl)-[1,2,4]triazolo[4,3-a]pyridine and (S)-7-(2-(2-chloro-6-fluorophenyl)propoxy)-3-(cyclopropylmethyl)-8-(trifluoromethyl)-[1,2,4]triazolo[4,3-a]pyridine

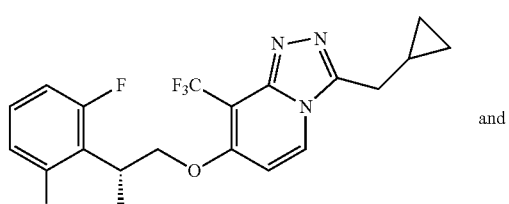

and

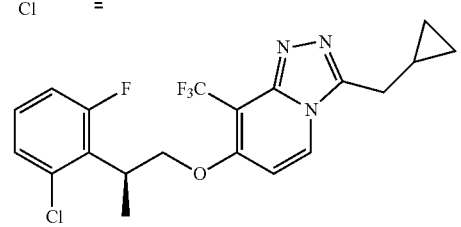

A racemic sample of 7-(2-(2-chloro-6-fluorophenyl)propoxy)-3-(cyclopropylmethyl)-8-(trifluoromethyl)-[1,2,4]triazolo[4,3-a]pyridine (from example 5, 52 mg) was purified using chiral preparatory HPLC to afford 14.4 mg of example 9 (first to elute) and 18.8 mg of example 10 (second to elute). HPLC Method: Chiralcel OD (21×250 mm, 10 uM), 20% ethanol/80% heptane (with 0.1% diethylamine), 15 mL/min, absorbance 220 nm. The absolute stereochemistry of individual enantiomers was not determined.

Example 11

7-(2-(4-Fluorophenoxy)-2-methylpropoxy)-3-(2,2,2-trifluoroethyl)-8-(trifluoromethyl)-[1,2,4]triazolo[4,3-a]pyridine

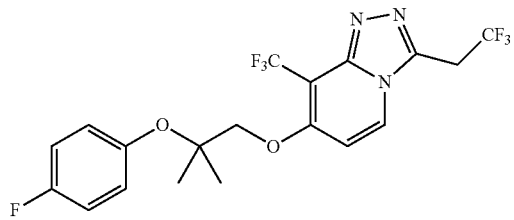 [SMILES: CC(C)(COc1ccn2c(CC(F)(F)F)nnc2c1C(F)(F)F)Oc1ccc(F)cc1]

The titled compound (56 mg, 19% yield over 2 steps) was prepared from 4-(2-(4-fluorophenoxy)-2-methylpropoxy)-2-hydrazinyl-3-(trifluoromethyl)pyridine (from preparation J) and 3,3,3-trifluoropropanoyl chloride (commercially available) following procedures analogous to steps 1A and 1B. The final product was purified using silica gel column chromatography (100% EtOAc) and was recrystallized from ethyl acetate/hexane.

Example 12

3-(3-(Cyclopropylmethyl)-8-(trifluoromethyl)-[1,2,4]triazolo[4,3-a]pyridin-7-yloxy)-2-(4-fluorophenyl)-2-methylpropanenitrile, TFA salt

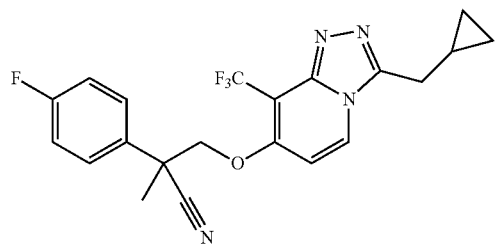 [SMILES: CC(C#N)(COc1ccn2c(CC3CC3)nnc2c1C(F)(F)F)c1ccc(F)cc1]

The titled compound (105 mg, 27% yield over 2 steps) was prepared from 2-(4-fluorophenyl)-3-((2-hydrazinyl-3-(trifluoromethyl)pyridin-4-yl)oxy)-2-methylpropanenitrile (from preparation L) following procedures analogous to steps 1A and 1B. The final product was purified using silica gel column chromatography (100% EtOAc) and reverse phase preparatory HPLC.

Example 13

7-(2-(4-Chlorophenoxy)-2-methylpropoxy)-3-(cyclopropylmethyl)-8-(trifluoromethyl)-[1,2,4]triazolo[4,3-a]pyridine

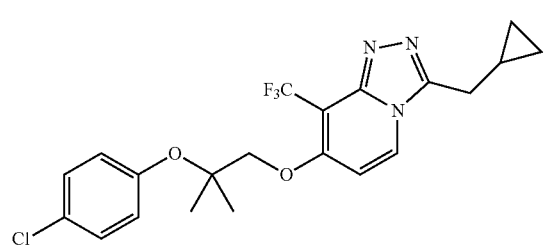 [SMILES: CC(C)(COc1ccn2c(CC3CC3)nnc2c1C(F)(F)F)Oc1ccc(Cl)cc1]

The titled compound (173 mg, 56% yield over 2 steps) was prepared from 4-(2-(4-chlorophenoxy)-2-methylpropoxy)-2-hydrazinyl-3-(trifluoromethyl)pyridine (from preparation N) following procedures analogous to steps 1A and 1B. The product was purified using silica gel column chromatography (100% EtOAc) and was recrystallized from ethyl acetate/hexanes.

Examples 14 and 15

(R)-3-(3-(Cyclopropylmethyl)-8-(trifluoromethyl)-[1,2,4]triazolo[4,3-a]pyridin-7-yloxy)-2-(4-fluorophenyl)-2-methylpropanenitrile and (S)-3-(3-(Cyclopropylmethyl)-8-(trifluoromethyl)-[1,2,4]triazolo[4,3-a]pyridin-7-yloxy)-2-(4-fluorophenyl)-2-methylpropanenitrile

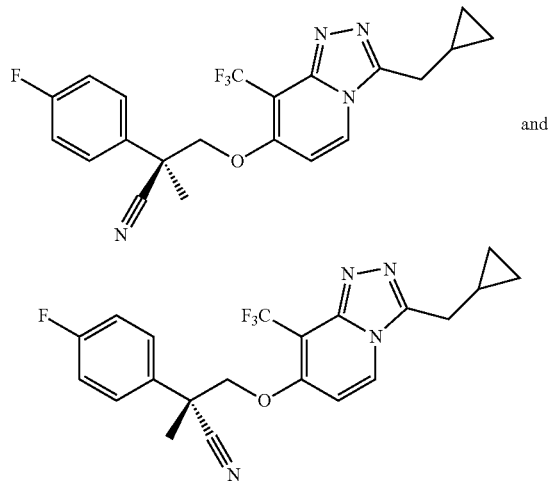

and

A racemic sample of 3-((3-(cyclopropylmethyl)-8-(trifluoromethyl)-[1,2,4]triazolo[4,3-a]pyridin-7-yl)oxy)-2-(4-fluorophenyl)-2-methylpropanenitrile, TFA (105 mg, 27% yield) (from example 12, 53 mg) was purified using chiral preparatory HPLC to afford 18.5 mg of example 14 (first to elute) and 16.7 mg of example 15 (second to elute). HPLC Method: ChiralPak AS-H (21×250 mm, 10 uM), 20% ethanol/80% heptane (with 0.1% diethylamine), 15 mL/min, absorbance 220 nm. The absolute stereochemistry of individual enantiomers was not determined.

Example 16

3-(Cyclopropylmethyl)-7-(2-(2,4-difluorophenoxy)-2-methylpropoxy)-8-(trifluoromethyl)-[1,2,4]triazolo[4,3-a]pyridine

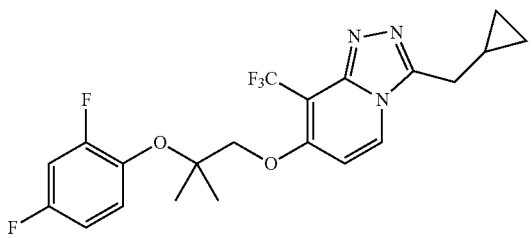 [SMILES: CC(C)(COc1ccn2c(CC3CC3)nnc2c1C(F)(F)F)Oc1ccc(F)cc1F]

The titled compound (173 mg, 54% yield over 2 steps) was prepared from 4-(2-(2,4-difluorophenoxy)-2-methylpropoxy)-2-hydrazinyl-3-(trifluoromethyl)pyridine (from preparation P) following procedures analogous to steps 1A and 1B. The product was purified using silica gel column chromatography (100% EtOAc).

Example 17

(1s,4s)-4-(3-(Cyclopropylmethyl)-8-(trifluoromethyl)-[1,2,4]triazolo[4,3-a]pyridin-7-yloxy)-1-(4-fluorophenyl)cyclohexanecarbonitrile

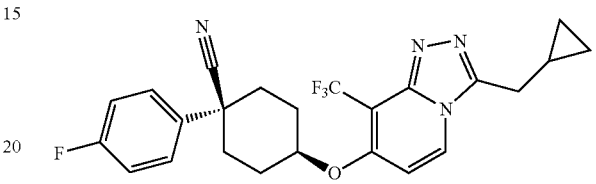

The titled compound (154 mg, 51% yield over 2 steps) was prepared from (1s,4s)-1-(4-fluorophenyl)-4-((2-hydrazinyl-3-(trifluoromethyl)pyridin-4-yl)oxy)cyclohexanecarbonitrile (from preparation R) following procedures analogous to steps 1A and 1B. The product was purified using silica gel column chromatography (ISCO system, 100% EtOAc).

Example 18

7-(2-(4-Chlorophenoxy)-2-methylpropoxy)-3-(ethoxymethyl)-8-(trifluoromethyl)-[1,2,4]triazolo[4,3-a]pyridine

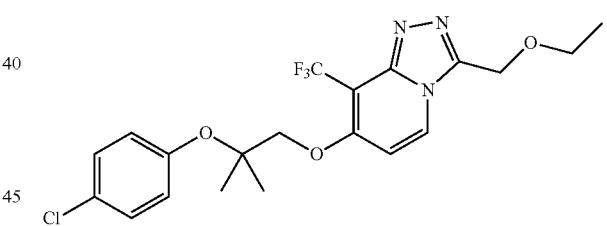

Step 18A

N'-(4-(2-(4-Chlorophenoxy)-2-methylpropoxy)-3-(trifluoromethyl)pyridin-2-yl)-2-ethoxyacetohydrazide (153 mg, 83% yield) was prepared from 4-(2-(4-chlorophenoxy)-2-methylpropoxy)-2-hydrazinyl-3-(trifluoromethyl)pyridine (from preparation N) and 2-ethoxyacetyl chloride (commercially available) following a procedure analogous to step 1A. LC-MS (M+H)$^+$ 462.1.

Step 18B

The titled compound (40 mg, 27% yield over 2 steps) was prepared from N'-(4-(2-(4-chlorophenoxy)-2-methylpropoxy)-3-(trifluoromethyl)pyridin-2-yl)-2-ethoxyacetohydrazide (from step 18A) following a procedure analogous to step 1B. The crude product was purified using silica gel column chromatography (100% EtOAc) and then preparative LC/MS (column: XBridge C18, 19×200 mm, 5-µm particles; mobile phase A: 5:95 acetonitrile:water with 10-mM ammonium acetate; mobile phase B: 95:5 acetonitrile:water with 10-mM ammonium acetate; gradient: 30-80% B over 40 minutes, then a 5-minute hold at 100% B; flow: 20 mL/min).

Example 19

3-(Cyclopropylmethyl)-7-((1s,4s)-4-(4-fluorophenyl)-4-methoxycyclohexyloxy)-8-(trifluoromethyl)-[1,2,4]triazolo[4,3-a]pyridine

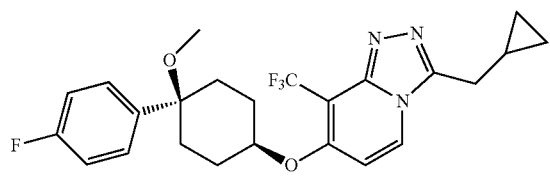 [SMILES: CO[C@]1(c2ccc(F)cc2)CC[C@H](Oc2ccn3c(CC4CC4)nnc3c2C(F)(F)F)CC1]

The titled compound (92 mg, 67% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) following procedures analogous to steps 1A and 1B. The final product was purified using silica gel column chromatography (100% EtOAc).

Example 20

3-(Cyclopropylmethyl)-7-((1r,4r)-4-phenylcyclohexyloxy)-8-(trifluoromethyl)-[1,2,4]triazolo[4,3-a]pyridine

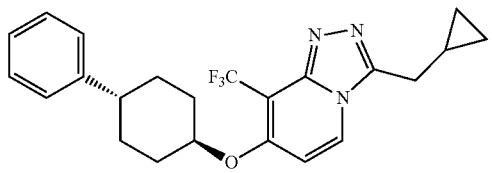 [SMILES: FC(F)(F)c1c(O[C@H]2CC[C@H](c3ccccc3)CC2)ccn2c(CC3CC3)nnc12]

The titled compound (147 mg, 64% yield over 2 steps) was prepared from 2-hydrazinyl-4-(((1s,4s)-4-phenylcyclohexyl)oxy)-3-(trifluoromethyl)pyridine (from preparation T) following procedures analogous to steps 1A and 1B. The product was purified using silica gel column chromatography (100% EtOAc).

Example 21

3-(Cyclopropylmethyl)-7-(2-(4-fluorophenyl)-2-methoxypropoxy)-8-(trifluoromethyl)-[1,2,4]triazolo[4,3-a]pyridine

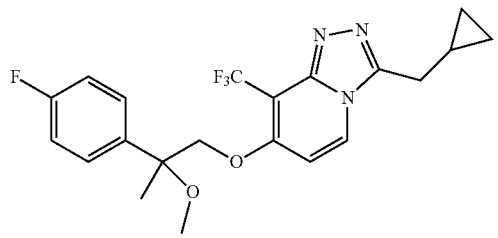 [SMILES: COC(C)(COc1ccn2c(CC3CC3)nnc2c1C(F)(F)F)c1ccc(F)cc1]

The titled compound (131 mg, 56% yield over 2 steps) was prepared from 4-(2-(4-fluorophenyl)-2-methoxypropoxy)-2-hydrazinyl-3-(trifluoromethyl)pyridine (from preparation V) following procedures analogous to steps 1A and 1B. The final product was purified using silica gel column chromatography (100% EtOAc).

Example 22

7-(2-(4-Chlorophenoxy)-2-methylpropoxy)-3-((2,2,2-trifluoroethoxy)methyl)-8-(trifluoromethyl)-[1,2,4]triazolo[4,3-a]pyridine, TFA salt

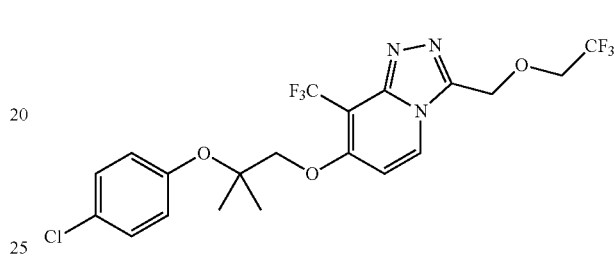

Step 22A

N'-(4-(2-(4-Chlorophenoxy)-2-methylpropoxy)-3-(trifluoromethyl)pyridin-2-yl)-2-(2,2,2-trifluoroethoxy)acetohydrazide (130 mg, 100% yield) was prepared from 4-(2-(4-chlorophenoxy)-2-methylpropoxy)-2-hydrazinyl-3-(trifluoromethyl)pyridine (from preparation N) and 2-(2,2,2-trifluoroethoxy)acetyl chloride (WO 87/07270) following a procedure analogous to step 1A. LC-MS (M+H)$^+$ 516.1.

Step 22B

The titled compound (39 mg, 25% yield over 2 steps) was prepared from N'-(4-(2-(4-chlorophenoxy)-2-methylpropoxy)-3-(trifluoromethyl)pyridin-2-yl)-2-(2,2,2-trifluoroethoxy)acetohydrazide (from step 22A) following a procedure analogous to step 1B. The crude product was purified using silica gel column chromatography (20% EtOAc/hexanes) and then reverse phase preparatory HPLC.

Example 23

7-(2-(4-Chlorophenoxy)-2-methylpropoxy)-3-(methoxymethyl)-8-(trifluoromethyl)-[1,2,4]triazolo[4,3-a]pyridine, TFA salt

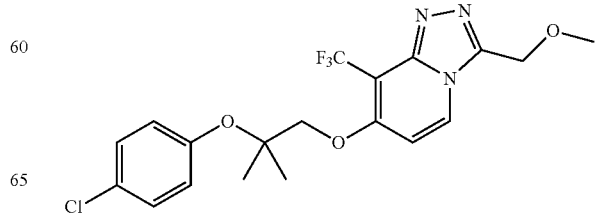

Step 23A

N' N'-(4-(2-(4-Chlorophenoxy)-2-methylpropoxy)-3-(trifluoromethyl)pyridin-2-yl)-2-methoxyacetohydrazide (113 mg, 100% yield) was prepared from 4-(2-(4-chlorophenoxy)-2-methylpropoxy)-2-hydrazinyl-3-(trifluoromethyl)pyridine (from preparation N) and 2-methoxyacetyl chloride (commercially available) following a procedure analogous to step 1A. LC-MS (M+H)$^+$ 448.1.

Step 23B

The titled compound (43 mg, 30% yield over 2 steps) was prepared from N' N'-(4-(2-(4-Chlorophenoxy)-2-methylpropoxy)-3-(trifluoromethyl)pyridin-2-yl)-2-methoxyacetohydrazide (from step 23A) following a procedure analogous to step 1B. The crude product was purified using silica gel column chromatography (100% EtOAc) and then reverse phase preparatory HPLC.

Examples 24 and 25

(R)-3-(Cyclopropylmethyl)-7-(2-(4-fluorophenyl)-2-methoxypropoxy)-8-(trifluoromethyl)-[1,2,4]triazolo[4,3-a]pyridine and (S)-3-(Cyclopropylmethyl)-7-(2-(4-fluorophenyl)-2-methoxypropoxy)-8-(trifluoromethyl)-[1,2,4]triazolo[4,3-a]pyridine

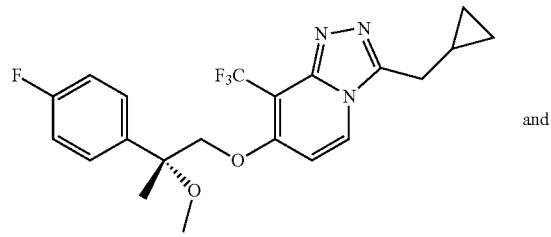

and

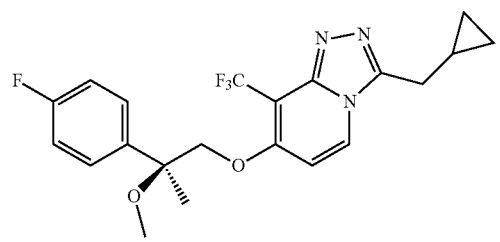

A sample of 3-(cyclopropylmethyl)-7-(2-(4-fluorophenyl)-2-methoxypropoxy)-8-(trifluoromethyl)-[1,2,4]triazolo[4,3-a]pyridine, TFA (example 21, 50 mg) was purified using chiral preparatory HPLC to afford 20 mg of example 24 (first to elute) and 19 mg of example 25 (second to elute). HPLC Method: ChiralCel OD (21×250 mm, 10 uM), 20% ethanol/80% heptane (with 0.1% diethylamine), 15 mL/min, absorbance 220 nm. The absolute stereochemistry of individual enantiomers was not determined.

Example 26

(1s,4s)-4-(3-(Cyclopropylmethyl)-8-(trifluoromethyl)-[1,2,4]triazolo[4,3-a]pyridin-7-yloxy)-1-(3,4-difluorophenyl)cyclohexanol, TFA salt

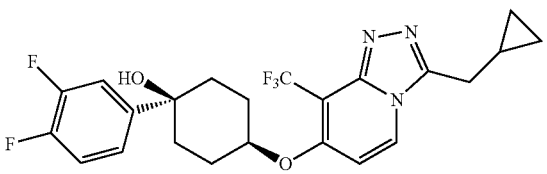 [SMILES: O[C@]1(c2ccc(F)c(F)c2)CC[C@H](Oc2ccn3c(CC4CC4)nnc3c2C(F)(F)F)CC1]

The titled compound (4.8 mg, 16% yield) was prepared from (1s,4s)-1-(3,4-difluorophenyl)-4-((2-hydrazinyl-3-(trifluoromethyl)pyridin-4-yl)oxy)cyclohexanol (from preparation X) following procedures analogous to steps 1A and 1B. The crude product mixture was purified using reverse phase preparatory HPLC.

Example 27

7-((1r,4r)-4-Phenylcyclohexyloxy)-3-((2,2,2-trifluoroethoxy)methyl)-8-(trifluoromethyl)-[1,2,4]triazolo[4,3-a]pyridine

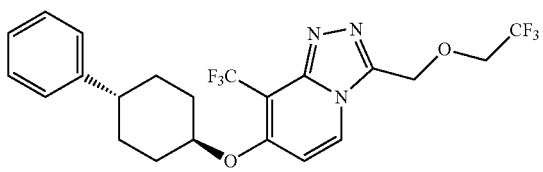 [SMILES: FC(F)(F)COCc1nnc2c(C(F)(F)F)c(O[C@H]3CC[C@H](c4ccccc4)CC3)ccn12]

Step 27A

N'-(4-(((1r,4r)-4-phenylcyclohexyl)oxy)-3-(trifluoromethyl)pyridin-2-yl)-2-(2,2,2-trifluoroethoxy)acetohydrazide (266 mg, 0.541 mmol, quantitative yield) was prepared from 2-hydrazinyl-4-(((1s,4s)-4-phenylcyclohexyl)oxy)-3-(trifluoromethyl)pyridine (from preparation T) and 2-(2,2,2-trifluoroethoxy)acetyl chloride (WO 87/07270) following a procedure analogous to step 1A. LC-MS (M+H)$^+$ 492.2.

Step 27B

The titled compound (141 mg, 54% yield over two steps) was prepared from N'-(4-(((1r,4r)-4-phenylcyclohexyl)oxy)-3-(trifluoromethyl)pyridin-2-yl)-2-(2,2,2-trifluoroethoxy)acetohydrazide (from step 27A) following a procedure analogous to step 1B. The crude product was purified using silica gel column chromatography (100% EtOAc).

Example 28

3-(Cyclopropylmethyl)-7-((1s,4s)-4-(3,4-difluorophenyl)-4-methoxycyclohexyloxy)-8-(trifluoromethyl)-[1,2,4]triazolo[4,3-a]pyridine

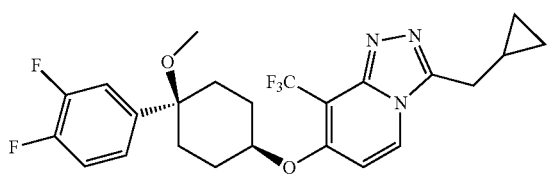 [SMILES: CO[C@]1(c2ccc(F)c(F)c2)CC[C@H](Oc2ccn3c(CC4CC4)nnc3c2C(F)(F)F)CC1]

The titled compound (49 mg, 22% yield over 2 steps) was prepared from 4-(((1s,4s)-4-(3,4-difluorophenyl)-4-methoxycyclohexyl)oxy)-2-hydrazinyl-3-(trifluoromethyl)pyridine (from preparation Y) following procedures analogous to steps 1A and 1B. The final product was purified using silica gel column chromatography (100% EtOAc).

Example 29

7-((1-(4-Chlorophenyl)cyclopropyl)methoxy)-3-(cyclopropylmethyl)-8-(trifluoromethyl)-[1,2,4]triazolo[4,3-a]pyridine

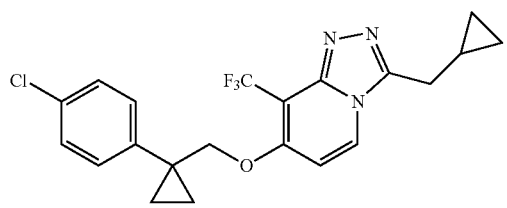 [SMILES: FC(F)(F)c1c(OCC2(c3ccc(Cl)cc3)CC2)ccn2c(CC3CC3)nnc12]

The titled compound (131 mg, 20% yield over 2 steps) was prepared from 4-((1-(4-chlorophenyl)cyclopropyl)methoxy)-2-hydrazinyl-3-(trifluoromethyl)pyridine (from preparation Z) following procedures analogous to steps 1A and 1B. The final product was purified by silica-gel column chromatography (100% ethyl acetate).

Example 30

3-(Cyclopropylmethyl)-7-((1-(4-fluorophenyl)cyclopropyl)methoxy)-8-(trifluoromethyl)-[1,2,4]triazolo[4,3-a]pyridine

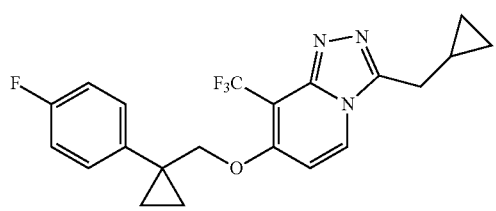 [SMILES: Fc1ccc(C2(COc3ccn4c(CC5CC5)nnc4c3C(F)(F)F)CC2)cc1]

The titled compound (64 mg, 9% yield over 2 steps) was prepared from 4-((1-(4-fluorophenyl)cyclopropyl)methoxy)-2-hydrazinyl-3-(trifluoromethyl)pyridine (from preparation AA) following the procedures detailed in steps 1A and 1B. The final product was purified by silica-gel column chromatography (0-100% ethyl acetate/hexanes).

Example 31

(±)-7-(((1S,2S)-2-(4-chlorophenyl)cyclopropyl)methoxy)-3-(cyclopropylmethyl)-8-(trifluoromethyl)-[1,2,4]triazolo[4,3-a]pyridine

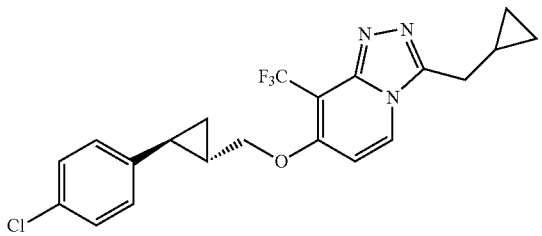 [SMILES: FC(F)(F)c1c(OC[C@H]2C[C@@H]2c2ccc(Cl)cc2)ccn2c(CC3CC3)nnc12]

The titled compound (145 mg, 26% yield over 2 steps) was prepared from 4-((2-(4-chlorophenyl)cyclopropyl)methoxy)-2-hydrazinyl-3-(trifluoromethyl)pyridine (from preparation AC) following procedures analogous to steps 1A and 1B. The final product was purified by silica-gel column chromatography (0-100% ethyl acetate/hexanes).

Example 32

(±)-3-(Cyclopropylmethyl)-7-(((1S,2S)-2-(2-fluoro-6-methoxyphenyl)cyclopropyl)methoxy)-8-(trifluoromethyl)-[1,2,4]triazolo[4,3-a]pyridine

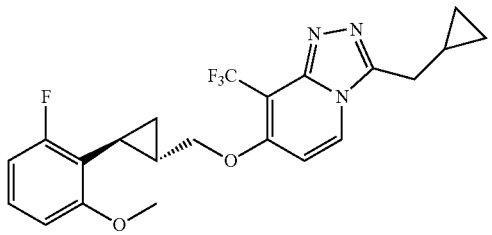 [SMILES: COc1cccc(F)c1[C@H]1C[C@@H]1COc1ccn2c(CC3CC3)nnc2c1C(F)(F)F]

The titled compound (43 mg, 11% yield over 2 steps) was prepared from 4-((2-(2-fluoro-6-methoxyphenyl)cyclopropyl)methoxy)-2-hydrazinyl-3-(trifluoromethyl)pyridine (from preparation AE) following procedures analogous to steps 1A and 1B. The final product was purified by silica-gel column chromatography (100% ethyl acetate).

Example 33

7-(((1R,2R)-2-(4-Chlorophenyl)cyclopropyl)methoxy)-3-(cyclopropylmethyl)-8-(trifluoromethyl)-[1,2,4]triazolo[4,3-a]pyridine

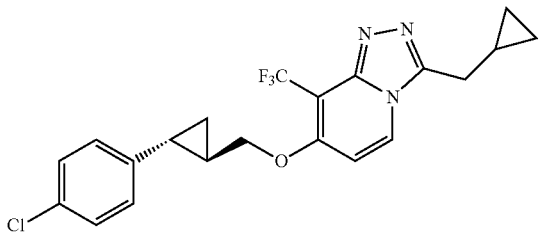 [SMILES: FC(F)(F)c1c(OC[C@@H]2C[C@H]2c2ccc(Cl)cc2)ccn2c(CC3CC3)nnc12]

and

Example 34

7-(((1S,2S)-2-(4-Chlorophenyl)cyclopropyl)methoxy)-3-(cyclopropylmethyl)-8-(trifluoromethyl)-[1,2,4]triazolo[4,3-a]pyridine

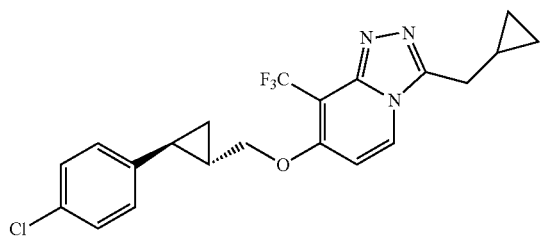 [SMILES: FC(F)(F)c1c(OC[C@H]2C[C@@H]2c2ccc(Cl)cc2)ccn2c(CC3CC3)nnc12]

A sample of (±)-7-(((1S,2S)-2-(4-chlorophenyl)cyclopropyl)methoxy)-3-(cyclopropylmethyl)-8-(trifluoromethyl)-[1,2,4]triazolo[4,3-a]pyridine (from example 31, 233 mg) was purified using chiral preparatory HPLC to afford 61 mg of example 33 (first enantiomer to elute) and 60 mg of example 34 (second enantiomer to elute). HPLC Method: ChiralCel OD (21×250 mm, 10 uM), 10% ethanol/90% heptane (with 0.1% diethylamine), 15 mL/min, absorbance 254 nm. The absolute stereochemistry of example 34 was confirmed as (1S,2S) through an independent asymmetric synthesis. The stereochemistry of example 33 was assigned as (1R,2R) by default.

Examples 35 and 36

3-(Cyclopropylmethyl)-7-(((1S,2S)-2-(2-fluoro-6-methoxyphenyl)cyclopropyl)methoxy)-8-(trifluoromethyl)-[1,2,4]triazolo[4,3-a]pyridine and 3-(Cyclopropylmethyl)-7-(((1R,2R)-2-(2-fluoro-6-methoxyphenyl)cyclopropyl)methoxy)-8-(trifluoromethyl)-[1,2,4]triazolo[4,3-a]pyridine

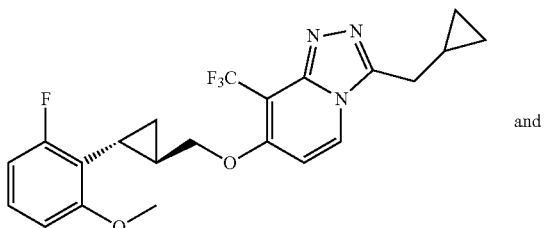

and

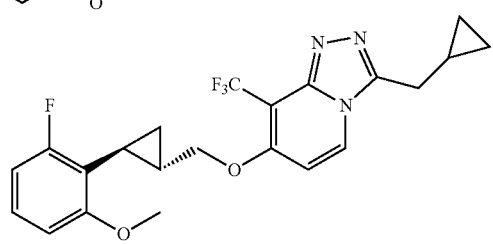

A sample of (±)-3-(cyclopropylmethyl)-7-(((1S,2S)-2-(2-fluoro-6-methoxyphenyl)cyclopropyl)methoxy)-8-(trifluoromethyl)-[1,2,4]triazolo[4,3-a]pyridine (example 32, 39 mg) was purified using chiral preparatory HPLC to afford 11 mg of example 35 (first to elute) and 10 mg of example 36 (second to elute). HPLC Method: Chiralcel OD (21×250 mm, 10 uM), 20% ethanol/80% heptane (with 0.1% diethylamine), 15 mL/min, absorbance 220 nm. The absolute stereochemistry of the individual enantiomers was not determined.

Example 37

(±)-3-(Cyclopropylmethyl)-7-(((1S,2S)-2-(2-methoxyphenyl)cyclopropyl)methoxy)-8-(trifluoromethyl)-[1,2,4]triazolo[4,3-a]pyridine

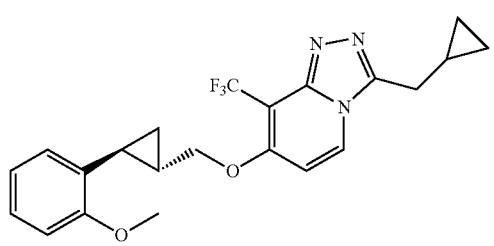 [SMILES: COc1ccccc1[C@H]1C[C@@H]1COc1ccn2c(CC3CC3)nnc2c1C(F)(F)F]

The titled compound (61 mg, 40% yield over 2 steps) was prepared from (±)-2-hydrazinyl-4-(((1S,2S)-2-(2-methoxyphenyl)cyclopropyl)methoxy)-3-(trifluoromethyl)pyridine (from preparation AG) following procedures analogous to steps 1A and 1B. The final product was purified by silica-gel column chromatography (100% ethyl acetate).

Example 38

(±)-3-(Cyclopropylmethyl)-7-(((1S,2S)-2-(2-(trifluoromethoxy)phenyl)cyclopropyl)methoxy)-8-(trifluoromethyl)-[1,2,4]triazolo[4,3-a]pyridine

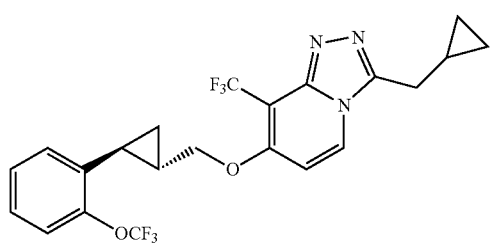 [SMILES: FC(F)(F)Oc1ccccc1[C@H]1C[C@@H]1COc1ccn2c(CC3CC3)nnc2c1C(F)(F)F]

The titled compound (71 mg, 43% yield over 2 steps) was prepared from (±)-2-hydrazinyl-4-(((1S,2S)-2-(2-(trifluoromethoxy)phenyl)cyclopropyl)methoxy)-3-(trifluoromethyl)pyridine (from preparation AI) following procedures analogous to steps 1A and 1B. The final product was purified by silica-gel column chromatography (0-100% ethyl acetate).

Examples 39 and 40

3-(Cyclopropylmethyl)-7-(((1S,2S)-2-(2-methoxyphenyl)cyclopropyl)methoxy)-8-(trifluoromethyl)-[1,2,4]triazolo[4,3-a]pyridine and 3-(Cyclopropylmethyl)-7-(((1R,2R)-2-(2-methoxyphenyl)cyclopropyl)methoxy)-8-(trifluoromethyl)-[1,2,4]triazolo[4,3-a]pyridine

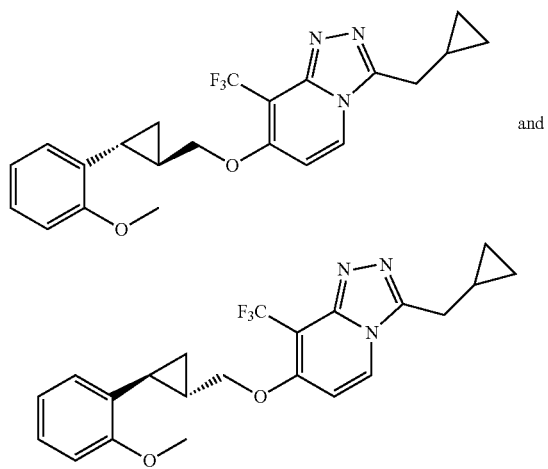

A sample of (±)-3-(cyclopropylmethyl)-7-(((1S,2S)-2-(2-methoxyphenyl)cyclopropyl)methoxy)-8-(trifluoromethyl)-[1,2,4]triazolo[4,3-a]pyridine (example 37, 50 mg) was purified using chiral preparatory HPLC to afford 11 mg of example 39 (first to elute) and 11 mg of example 40 (second to elute). HPLC Method: Chiralcel OD-H (21×250 mm, 10 uM), 20% ethanol/80% heptane (with 0.1% diethylamine), 15 mL/min, absorbance 220 nm. The absolute stereochemistry of individual enantiomers was not determined.

Examples 41 and 42

3-(Cyclopropylmethyl)-7-(((1S,2S)-2-(2-(trifluoromethoxy)phenyl)cyclopropyl)methoxy)-8-(trifluoromethyl)-[1,2,4]triazolo[4,3-a]pyridine and 3-(Cyclopropylmethyl)-7-(((1R,2R)-2-(2-(trifluoromethoxy)phenyl)cyclopropyl)methoxy)-8-(trifluoromethyl)-[1,2,4]triazolo[4,3-a]pyridine

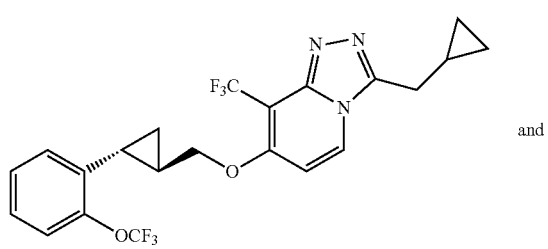

and

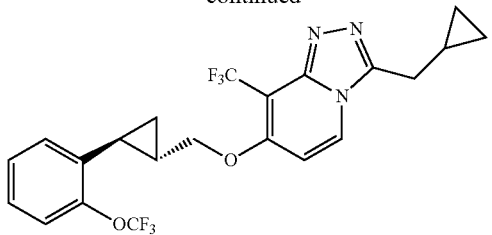

A sample of (±)-3-(cyclopropylmethyl)-7-(((1S,2S)-2-(2-(trifluoromethoxy)phenyl)cyclopropyl)methoxy)-8-(trifluoromethyl)-[1,2,4]triazolo[4,3-a]pyridine (example 38, 61 mg) was purified using chiral supercritical fluid chromatography (SFC) to afford 20 mg of example 41 (first to elute) and 22 mg of example 42 (second to elute). SFC Method: Chiralcel OD-H (30×250 mm, 5 uM), 15% methanol (0.1% DEA)/90% $CO_2$, 150 bar, 70 mL/min, absorbance 220 nm. The absolute stereochemistry of individual enantiomers was not determined.

Example 43

(±)-3-(Cyclopropylmethyl)-7-(((1S,2S)-2-(2-fluorophenyl)cyclopropyl)methoxy)-8-(trifluoromethyl)-[1,2,4]triazolo[4,3-a]pyridine

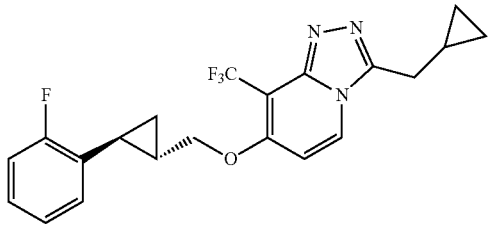 [SMILES: Fc1ccccc1[C@H]1C[C@@H]1COc1ccn2c(CC3CC3)nnc2c1C(F)(F)F]

The titled compound (1.4 mg, 2% yield) was prepared from (±)-((1S,2S)-2-(2-fluorophenyl)cyclopropyl)methanol (from preparation AJ) and 7-chloro-3-(cyclopropylmethyl)-8-(trifluoromethyl)-[1,2,4]triazolo[4,3-a]pyridine (from J. Med Chem. 2012, 55, 8770) following the same procedures and purification methods as described for example 4.

Example 44

(±)-3-(Cyclopropylmethyl)-7-(((1S,2S)-2-(2,5-difluorophenyl)cyclopropyl)methoxy)-8-(trifluoromethyl)-[1,2,4]triazolo[4,3-a]pyridine

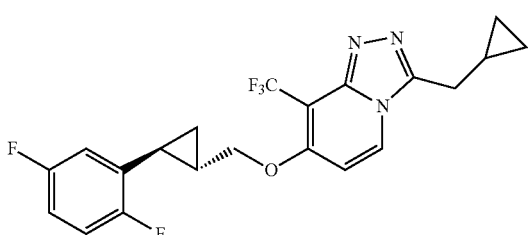

The titled compound (6.4 mg, 8% yield) was prepared from (±)-((1S,2S)-2-(2,5-difluorophenyl)cyclopropyl)methanol (from preparation AK) and 7-chloro-3-(cyclopropylmethyl)-8-(trifluoromethyl)-[1,2,4]triazolo[4,3-a]pyridine (from J. Med Chem. 2012, 55, 8770) following the same procedure and purification method as described for example 4.

Example 45

(±)-3-(Cyclopropylmethyl)-7-(((1S,2S)-2-(4-methoxyphenyl)cyclopropyl)methoxy)-8-(trifluoromethyl)-[1,2,4]triazolo[4,3-a]pyridine

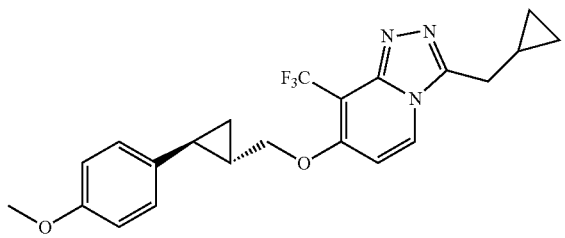 [SMILES: COc1ccc([C@H]2C[C@@H]2COc2ccn3c(CC4CC4)nnc3c2C(F)(F)F)cc1]

The titled compound (4.5 mg, 6% yield) was prepared from (±)-((1S,2S)-2-(4-methoxyphenyl)cyclopropyl)methanol (from preparation AL) and 7-chloro-3-(cyclopropylmethyl)-8-(trifluoromethyl)-[1,2,4]triazolo[4,3-a]pyridine (from *J. Med Chem.* 2012, 55, 8770) following the same procedures and purification methods as described for example 4.

Example 46

(1s,3s)-3-(3-(Cyclopropylmethyl)-8-(trifluoromethyl)-[1,2,4]triazolo[4,3-a]pyridin-7-yloxy)-1-(3-fluorophenyl)cyclobutanecarbonitrile

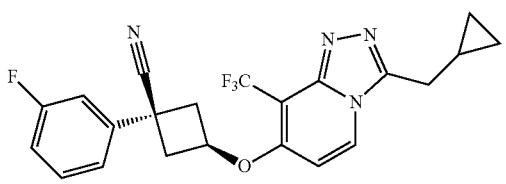 [SMILES: N#C[C@]1(c2cccc(F)c2)C[C@H](Oc2ccn3c(CC4CC4)nnc3c2C(F)(F)F)C1]

The titled compound (345 mg, 21% yield over 2 steps) was prepared from (1s,3s)-1-(3-fluorophenyl)-3-(2-hydrazinyl-3-(trifluoromethyl)pyridin-4-yloxy)cyclobutanecarbonitrile (from preparation AM) following procedures analogous to steps 1A and 1B. The final product was purified by silica-gel column chromatography (0-100% ethyl acetate).

Example 47

(±)-3-(Cyclopropylmethyl)-7-(((1S,2S)-2-(3,6-difluoro-2-methoxyphenyl)cyclopropyl)methoxy)-8-(trifluoromethyl)-[1,2,4]triazolo[4,3-a]pyridine

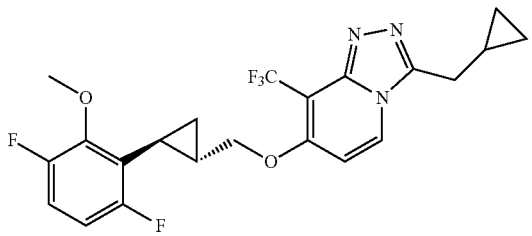 [SMILES: COc1c(F)ccc(F)c1[C@H]1C[C@@H]1COc1ccn2c(CC3CC3)nnc2c1C(F)(F)F]

The titled compound (9.1 mg, 11% yield) was prepared from (±)-((1S,2S)-2-(3,6-difluoro-2-methoxyphenyl)cyclopropyl)methanol (from preparation AN) and 7-chloro-3-(cyclopropylmethyl)-8-(trifluoromethyl)-[1,2,4]triazolo[4,3-a]pyridine (from *J. Med Chem.* 2012, 55, 8770) following the same procedures and purification method as described for example 4.

Example 48

(±)-7-(((1S,2S)-2-(2-chloro-6-fluorophenyl)cyclopropyl)methoxy)-3-(cyclopropylmethyl)-8-(trifluoromethyl)-[1,2,4]triazolo[4,3-a]pyridine

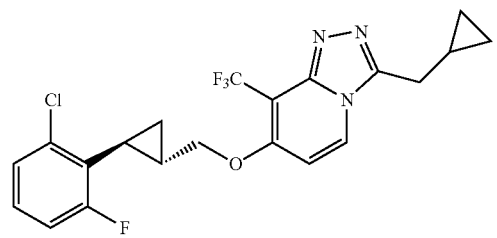 [SMILES: Fc1cccc(Cl)c1[C@H]1C[C@@H]1COc1ccn2c(CC3CC3)nnc2c1C(F)(F)F]

The titled compound (4.5 mg, 5% yield) was prepared from (±)-((1S,2S)-2-(2-chloro-6-fluorophenyl)cyclopropyl)methanol (from preparation AO) and 7-chloro-3-(cyclopropylmethyl)-8-(trifluoromethyl)-[1,2,4]triazolo[4,3-a]pyridine (from *J. Med Chem.* 2012, 55, 8770) following the same procedures and purification methods as described for example 4.

Example 49

(±)-3-(Cyclopropylmethyl)-7-(((1S,2S)-2-(4-fluoro-2-methoxyphenyl)cyclopropyl)methoxy)-8-(trifluoromethyl)-[1,2,4]triazolo[4,3-a]pyridine

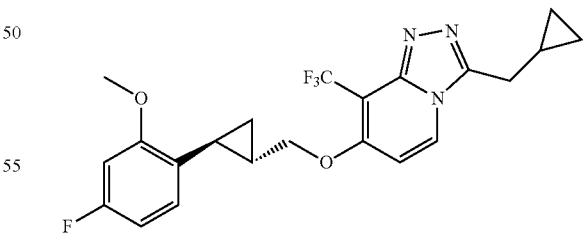

The titled compound (2.3 mg, 3% yield) was prepared from (±)-((1S,2S)-2-(4-fluoro-2-methoxyphenyl)cyclopropyl)methanol (from preparation A2) and 7-chloro-3-(cyclopropylmethyl)-8-(trifluoromethyl)-[1,2,4]triazolo[4,3-a]pyridine (from *J. Med Chem.* 2012, 55, 8770) following the same procedures and purification methods as described for example 4.

Example 50

(1s,3s)-3-(3-(Cyclopropylmethyl)-8-(trifluoromethyl)-[1,2,4]triazolo[4,3-a]pyridin-7-yloxy)-1-(4-fluorophenyl)cyclobutanecarbonitrile

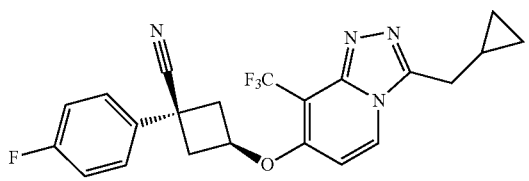 [SMILES: N#C[C@]1(c2ccc(F)cc2)C[C@H](Oc2ccn3c(CC4CC4)nnc3c2C(F)(F)F)C1]

The titled compound (235 mg, 42% yield over 2 steps) was prepared from (1s,3s)-1-(4-fluorophenyl)-3-(2-hydrazinyl-3-(trifluoromethyl)pyridin-4-yloxy)cyclobutanecarbonitrile (from preparation AQ) following procedures analogous to steps 1A and 1B. The final product was purified by silica-gel column chromatography (0-100% ethyl acetate).

Example 51

3-(Cyclopropylmethyl)-7-((1-(2,4-difluorophenyl)cyclopropyl)methoxy)-8-(trifluoromethyl)-[1,2,4]triazolo[4,3-a]pyridine

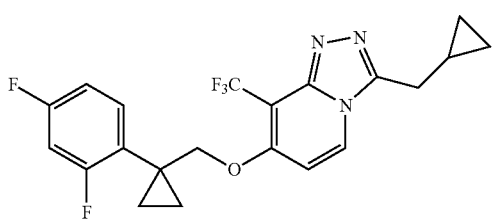 [SMILES: Fc1ccc(C2(COc3ccn4c(CC5CC5)nnc4c3C(F)(F)F)CC2)c(F)c1]

The titled compound (2.4 mg, 2% yield) was prepared from (1-(2,4-difluorophenyl)cyclopropyl)methanol (from preparation AR) and 7-chloro-3-(cyclopropylmethyl)-8-(trifluoromethyl)-[1,2,4]triazolo[4,3-a]pyridine (from *J. Med Chem.* 2012, 55, 8770) following the same procedures and purification methods as described for example 4.

Example 52

7-(((1S,2S)-2-(4-Fluorophenyl)cyclopropyl)methoxy)-3-(2,2,2-trifluoroethyl)-8-(trifluoromethyl)-[1,2,4]triazolo[4,3-a]pyridine

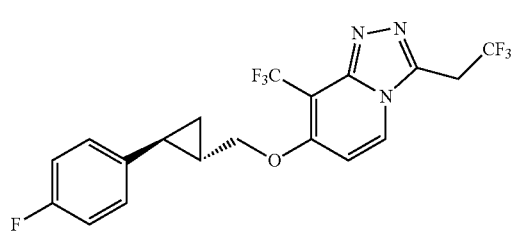 [SMILES: Fc1ccc([C@H]2C[C@@H]2COc2ccn3c(CC(F)(F)F)nnc3c2C(F)(F)F)cc1]

The titled compound (232 mg, 18% yield over 2 steps) was prepared from 4-(2-(4-fluorophenoxy)-2-methylpropoxy)-2-hydrazinyl-3-(trifluoromethyl)pyridine (from preparation AS) following procedures analogous to steps 7A and 1B. The final product was purified using silica gel column chromatography (0-100% EtOAc).

Example 53

(1s,3s)-3-(3-(Cyclopropylmethyl)-8-(trifluoromethyl)-[1,2,4]triazolo[4,3-a]pyridin-7-yloxy)-1-(2-methoxyphenyl)cyclobutanecarbonitrile

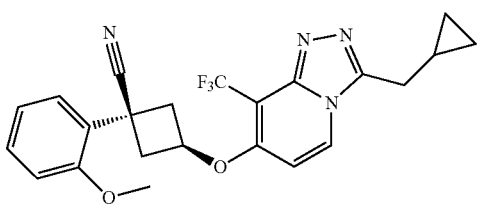 [SMILES: COc1ccccc1[C@]1(C#N)C[C@@H](Oc2ccn3c(CC4CC4)nnc3c2C(F)(F)F)C1]

The titled compound (435 mg, 36% yield over 2 steps) was prepared from (1s,3s)-3-(2-hydrazinyl-3-(trifluoromethyl)pyridin-4-yloxy)-1-(2-methoxyphenyl)cyclobutanecarbonitrile (from preparation AU) following procedures analogous to steps 1A and 1B. The final product was purified by silica-gel column chromatography (0-100% ethyl acetate).

Example 54

(1s,3s)-3-(3-(Cyclopropylmethyl)-8-(trifluoromethyl)-[1,2,4]triazolo[4,3-a]pyridin-7-yloxy)-1-(3,5-difluorophenyl)cyclobutanecarbonitrile

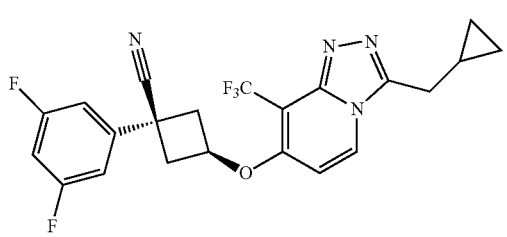 [SMILES: N#C[C@]1(c2cc(F)cc(F)c2)C[C@H](Oc2ccn3c(CC4CC4)nnc3c2C(F)(F)F)C1]

The titled compound (20 mg, 4% yield over 2 steps) was prepared from (1s,3s)-1-(3,5-difluorophenyl)-3-(2-hydrazinyl-3-(trifluoromethyl)pyridin-4-yloxy)cyclobutanecarbonitrile (from preparation AW) following procedures analogous to steps 1A and 1B. The final product was purified by preparative LC-MS.

Example 55

3-(Cyclopropylmethyl)-7-((1-(3,5-difluorophenyl)cyclopropyl)methoxy)-8-(trifluoromethyl)-[1,2,4]triazolo[4,3-a]pyridine

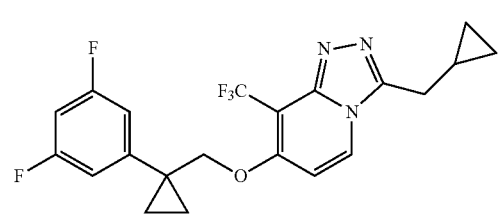 [SMILES: Fc1cc(F)cc(C2(COc3ccn4c(CC5CC5)nnc4c3C(F)(F)F)CC2)c1]

The titled compound (266 mg, 41% yield over 2 steps) was prepared from 4-((1-(3,5-difluorophenyl)cyclopropyl)methoxy)-2-hydrazinyl-3-(trifluoromethyl)pyridine (from preparation AY) following procedures analogous to steps 1A and 1B. The final product was purified by preparative LC-MS.

Example 56

3-(Cyclopropylmethyl)-7-((1-(3,5-dichlorophenyl)cyclopropyl)methoxy)-8-(trifluoromethyl)-[1,2,4]triazolo[4,3-a]pyridine

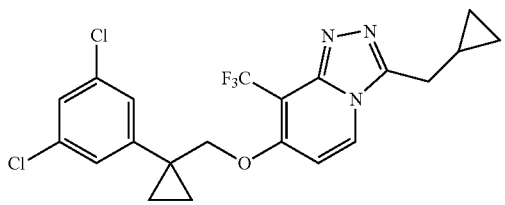 [SMILES: FC(F)(F)c1c(OCC2(c3cc(Cl)cc(Cl)c3)CC2)ccn2c(CC3CC3)nnc12]

The titled compound (101 mg, 15% yield over 2 steps) was prepared from 4-((1-(3,5-dichlorophenyl)cyclopropyl)methoxy)-2-hydrazinyl-3-(trifluoromethyl)pyridine (from preparation AAA) following procedures analogous to steps 1A and 1B. The final product was purified by preparative LC-MS.

Example 57

3-(Cyclopropylmethyl)-7-((1r,3r)-3-phenylcyclobutoxy)-8-(trifluoromethyl)-[1,2,4]triazolo[4,3-a]pyridine

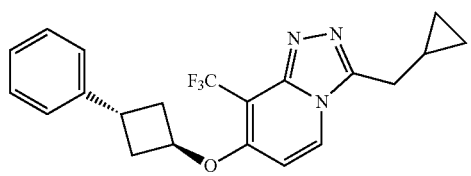 [SMILES: FC(F)(F)c1c(O[C@H]2C[C@H](c3ccccc3)C2)ccn2c(CC3CC3)nnc12]

The titled compound (40 mg, 34% yield over 2 steps) was prepared from 2-hydrazinyl-4-((1r,3r)-3-phenylcyclobutoxy)-3-(trifluoromethyl)pyridine (from preparation AAC) following procedures analogous to steps 1A and 1B. The final product was purified by preparative LC-MS.

Example 58

8-Chloro-7-(4-chlorobenzyloxy)-3-(cyclopropylmethyl)-[1,2,4]triazolo[4,3-a]pyridine, TFA salt

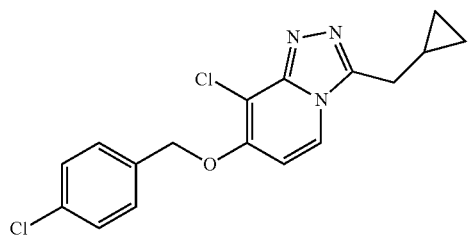 [SMILES: Clc1ccc(COc2ccn3c(CC4CC4)nnc3c2Cl)cc1]

A mixture of 1,10-phenanthroline (22.4 mg, 0.124 mmol), (4-chlorophenyl)methanol (commercially available, 108 mg, 0.757 mmol), 8-chloro-3-(cyclopropylmethyl)-7-iodo-[1,2,4]triazolo[4,3-a]pyridine ((from *J. Med. Chem.* 2012, 55, 8770), 35 mg, 0.105 mmol), copper(I) iodide (38 mg, 0.200 mmol), cesium carbonate (52 mg, 0.160 mmol), and toluene (1 mL) was heated in a sealed vial in an oil bath at 100° C. for 24 h. The reaction mixture was allowed to cool to rt and was filtered through celite. The solid was washed with acetonitrile. The filtrate was concentrated in vacuo. The residue was purified using reverse phase preparatory HPLC.

Example 59

8-Chloro-3-(cyclopropylmethyl)-7-(1-(4-fluorophenyl)ethoxy)-[1,2,4]triazolo[4,3-a]pyridine

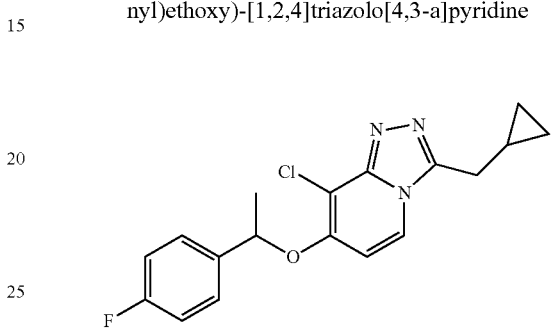

The titled compound (1.0 mg, 2% yield) was prepared from (4-chlorophenyl)methanol (commercially available) and 8-chloro-3-(cyclopropylmethyl)-7-iodo-[1,2,4]triazolo[4,3-a]pyridine (from *J. Med. Chem.* 2012, 55, 8770) following a procedure analogous to example 58. The product was purified using reverse phase preparatory HPLC.

Examples 60-75

Examples 60-76 were prepared in parallel fashion according to the following method. A stock solution of 8-chloro-3-(cyclopropylmethyl)-7-iodo-[1,2,4]triazolo[4,3-a]pyridine [(from *J. Med. Chem.* 2012, 55, 8770), 0.9 M in toluene, 1 mL, 0.090 mmol] was added to a 2.0-5.0 mL microwave vial charged with the corresponding commercially available alcohol (0.648 mmol), cesium carbonate (50.0 mg, 0.153 mmol), 1,10-phenanthroline (20.0 mg, 0.111 mmol), and 20.0 mg of copper(I) iodide (20.0 mg, 0.105 mmol). The vials were sealed and heated to 100° C. for 17 hours. The reaction mixtures were cooled to rt, diluted with 0.5 mL of acetonitrile, and then filtered. The filtrates were concentrated in vacuo at 34° C. for 1 hour. Each sample was diluted with 0.5 mL of DMF (0.5 mL) and purified using reverse phase preparative LC-MS.

Example 60

8-Chloro-7-(3-chlorobenzyloxy)-3-(cyclopropylmethyl)-[1,2,4]triazolo[4,3-a]pyridine

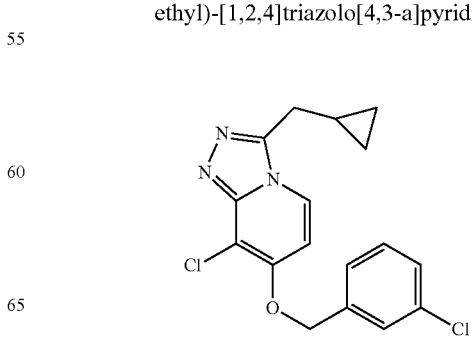

Example 61

8-Chloro-3-(cyclopropylmethyl)-7-(3-methoxybenzyloxy)-[1,2,4]triazolo[4,3-a]pyridine

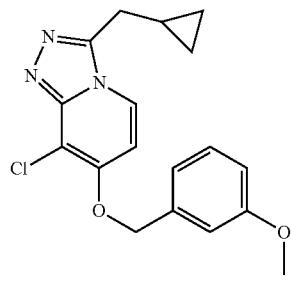 [SMILES: COc1cccc(COc2ccn3c(CC4CC4)nnc3c2Cl)c1]

Example 62

8-Chloro-3-(cyclopropylmethyl)-7-(3-(pyridin-3-yl)propoxy)-[1,2,4]triazolo[4,3-a]pyridine

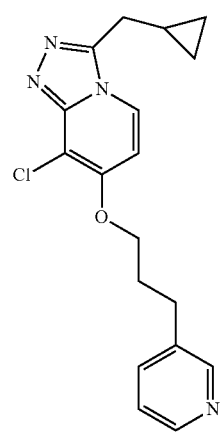 [SMILES: Clc1c(OCCCc2cccnc2)ccn2c(CC3CC3)nnc12]

Example 63

8-Chloro-3-(cyclopropylmethyl)-7-(2-phenoxyethoxy)-[1,2,4]triazolo[4,3-a]pyridine

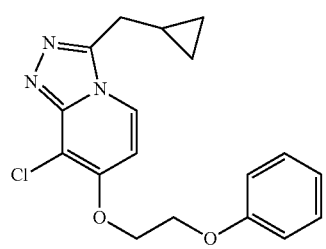 [SMILES: Clc1c(OCCOc2ccccc2)ccn2c(CC3CC3)nnc12]

Example 64

8-Chloro-3-(cyclopropylmethyl)-7-phenethoxy-[1,2,4]triazolo[4,3-a]pyridine

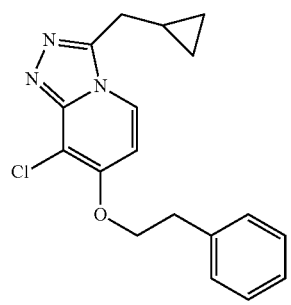 [SMILES: Clc1c(OCCc2ccccc2)ccn2c(CC3CC3)nnc12]

Example 65

8-Chloro-3-(cyclopropylmethyl)-7-(4-fluoro-3-methoxybenzyloxy)-[1,2,4]triazolo[4,3-a]pyridine

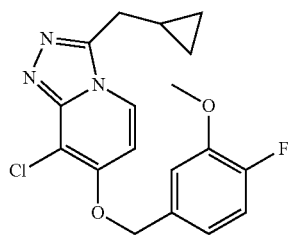 [SMILES: COc1cc(COc2ccn3c(CC4CC4)nnc3c2Cl)ccc1F]

Example 66

8-Chloro-7-(2-chlorobenzyloxy)-3-(cyclopropylmethyl)-[1,2,4]triazolo[4,3-a]pyridine

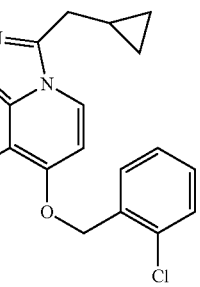

Example 67

8-Chloro-3-(cyclopropylmethyl)-7-(3-methylbenzyloxy)-[1,2,4]triazolo[4,3-a]pyridine

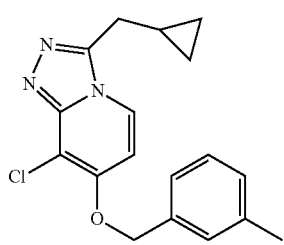 [SMILES: Cc1cccc(COc2ccn3c(CC4CC4)nnc3c2Cl)c1]

Example 68

8-Chloro-3-(cyclopropylmethyl)-7-(2-fluorobenzyloxy)-[1,2,4]triazolo[4,3-a]pyridine

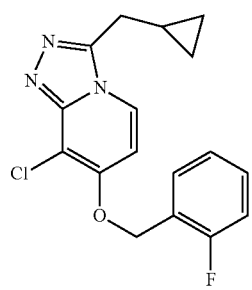 [SMILES: Fc1ccccc1COc1ccn2c(CC3CC3)nnc2c1Cl]

Example 69

8-Chloro-3-(cyclopropylmethyl)-7-(3,4-dichlorobenzyloxy)-[1,2,4]triazolo[4,3-a]pyridine

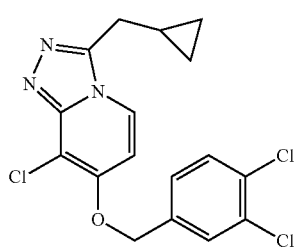 [SMILES: Clc1ccc(COc2ccn3c(CC4CC4)nnc3c2Cl)cc1Cl]

Example 70

8-Chloro-3-(cyclopropylmethyl)-7-(4-methoxybenzyloxy)-[1,2,4]triazolo[4,3-a]pyridine

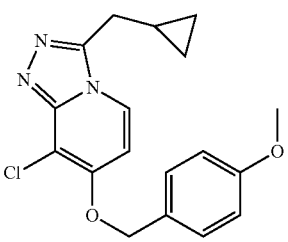 [SMILES: COc1ccc(COc2ccn3c(CC4CC4)nnc3c2Cl)cc1]

Example 71

8-Chloro-3-(cyclopropylmethyl)-7-(2,6-difluorobenzyloxy)-[1,2,4]triazolo[4,3-a]pyridine

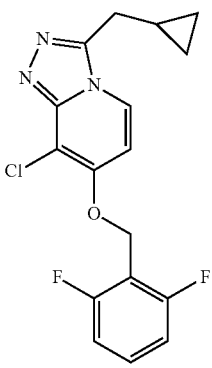 [SMILES: Fc1cccc(F)c1COc1ccn2c(CC3CC3)nnc2c1Cl]

Example 72

8-Chloro-3-(cyclopropylmethyl)-7-(2-fluoro-6-methoxybenzyloxy)-[1,2,4]triazolo[4,3-a]pyridine

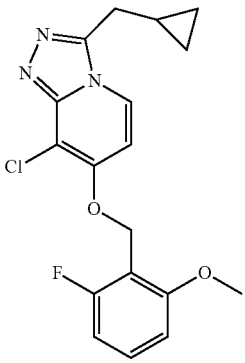 [SMILES: COc1cccc(F)c1COc1ccn2c(CC3CC3)nnc2c1Cl]

Example 73

8-Chloro-7-(5-chloro-2-(trifluoromethoxy)benzyloxy)-3-(cyclopropylmethyl)-[1,2,4]triazolo[4,3-a]pyridine

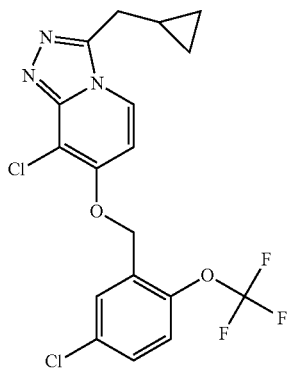 [SMILES: FC(F)(F)Oc1ccc(Cl)cc1COc1ccn2c(CC3CC3)nnc2c1Cl]

Example 74

8-Chloro-3-(cyclopropylmethyl)-7-(5-fluoro-2-methoxybenzyloxy)-[1,2,4]triazolo[4,3-a]pyridine

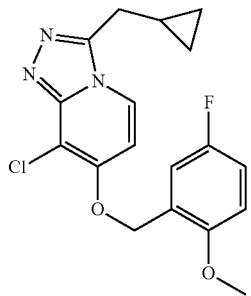 [SMILES: COc1ccc(F)cc1COc1ccn2c(CC3CC3)nnc2c1Cl]

Example 75

8-Chloro-7-(3-cyclopropoxybenzyloxy)-3-(cyclopropylmethyl)-[1,2,4]triazolo[4,3-a]pyridine

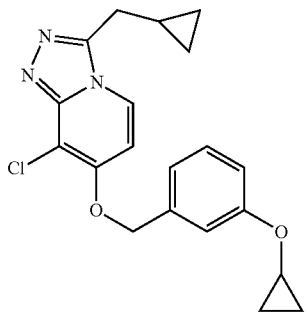 [SMILES: Clc1c(OCc2cccc(OC3CC3)c2)ccn2c(CC3CC3)nnc12]

Example 76

8-Chloro-3-(cyclopropylmethyl)-7-(3,5-difluorobenzyloxy)-[1,2,4]triazolo[4,3-a]pyridine

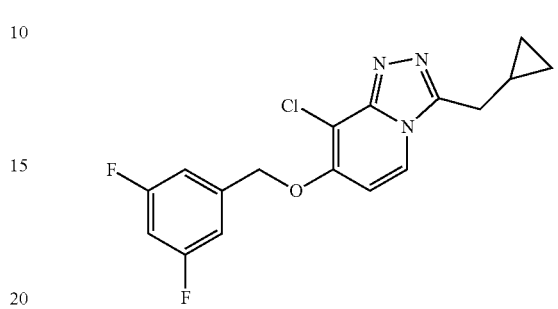

To a stirred mixture of 3-(cyclopropylmethyl)-8-(trifluoromethyl)-[1,2,4]triazolo[4,3-a]pyridin-7-ol (from preparation AAD, 32 mg, 0.12 mmol), 2-(bromomethyl)-1,3-difluorobenzene (31 mg, 0.15 mmol), and tetrahydrofuran (4 mL) was added potassium tert-butoxide (31 mg, 0.28 mmol) followed by DMF (1.5 mL) and the reaction mixture was stirred at rt overnight. The reaction mixture was concentrated in vacuo. The residue was purified using reverse phase preparative HPLC to afford the titled compound (16 mg, 34% yield) as a white solid.

Example 77

(±)-3-(Cyclopropylmethyl)-7-(((1S,2S)-2-(4-fluorophenyl)cyclopropyl)methoxy)-8-(trifluoromethyl)-[1,2,4]triazolo[4,3-a]pyridine

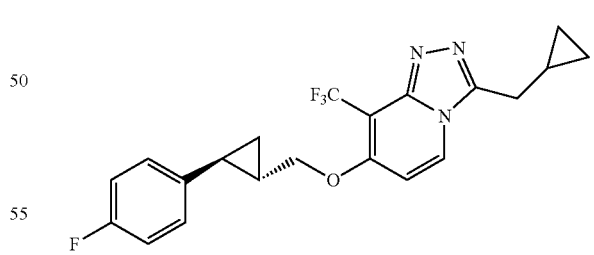

The titled compound (80 mg, 20% yield over 2 steps) was prepared from (±)-4-(((1S,2S)-2-(4-fluorophenyl)cyclopropyl)methoxy)-2-hydrazinyl-3-(trifluoromethyl)pyridine (from preparation AAF) following procedures analogous to steps 1A and 1B. The final product was purified by silica-gel column chromatography (0-100% ethyl acetate) and reverse phase preparatory HPLC.

Examples 78 and 79

3-(Cyclopropylmethyl)-7-(((1S,2S)-2-(2-fluorophenyl)cyclopropyl)methoxy)-8-(trifluoromethyl)-[1,2,4]triazolo[4,3-a]pyridine and 3-(Cyclopropylmethyl)-7-(((1R,2R)-2-(4-fluorophenyl)cyclopropyl)methoxy)-8-(trifluoromethyl)-[1,2,4]triazolo[4,3-a]pyridine

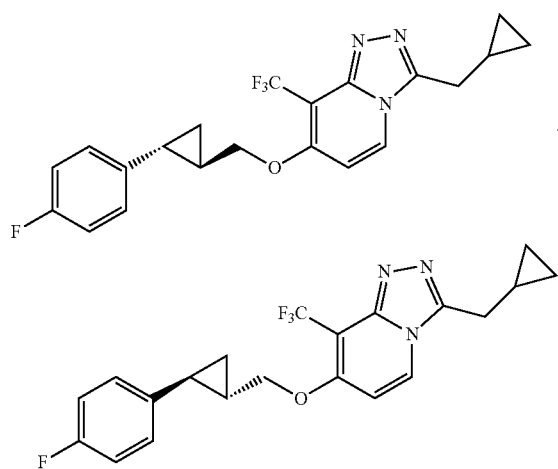

and

A sample of (±)-3-(cyclopropylmethyl)-7-(((1S,2S)-2-(4-fluorophenyl)cyclopropyl)methoxy)-8-(trifluoromethyl)-[1,2,4]triazolo[4,3-a]pyridine (example 78, 60 mg) was purified using chiral preparatory HPLC to afford 22 mg of example 79 (first enantiomer to elute) and 22 mg of example 80 (second enantiomer to elute). HPLC Method: Chiralcel OD-H (21×250 mm, 10 uM), 20% ethanol/80% heptane (with 0.1% diethylamine), 15 mL/min, absorbance 220 nm. The absolute stereochemistry of individual enantiomers was not determined.

Example 80

7-(2-Chloro-6-fluorophenethoxy)-3-(cyclopropylmethyl)-8-(trifluoromethyl)-[1,2,4]triazolo[4,3-a]pyridine

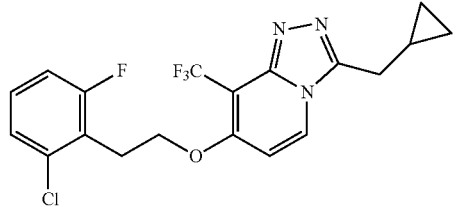 [SMILES: Fc1cccc(Cl)c1CCOc1ccn2c(CC3CC3)nnc2c1C(F)(F)F]

The titled compound (43 mg, 8% yield over 2 steps) was prepared from 4-(2-chloro-6-fluorophenethoxy)-2-hydrazinyl-3-(trifluoromethyl)pyridine (from preparation AAG) following procedures analogous to steps 1A and 1B. The final product was purified by silica-gel column chromatography (0-100% ethyl acetate) and reverse phase preparatory HPLC.

Example 81

3-(Cyclopropylmethyl)-7-(2,6-difluorophenethoxy)-8-(trifluoromethyl)-[1,2,4]triazolo[4,3-a]pyridine

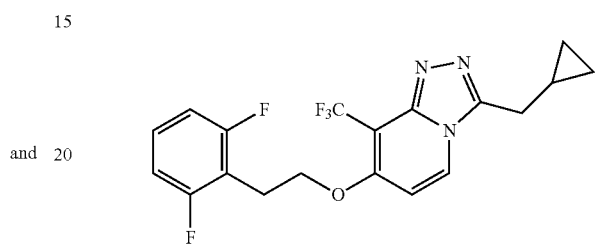

The titled compound (67 mg, 16% yield over 2 steps) was prepared from 4-(2,6-difluorophenethoxy)-2-hydrazinyl-3-(trifluoromethyl)pyridine (from preparation AAI) following procedures analogous to steps 1A and 1B. The final product was purified by reverse phase preparatory HPLC. The resulting TFA salt was dissolved in a minimum of methanol and partioned between ethyl acetate and aqueous sodium carbonate. The organic layer was washed with brine, dried over magnesium sulfate, filtered, and concentrated in vacuo to afford the titled compound.

Example 82

8-Chloro-3-(cyclopropylmethyl)-7-((2,6-dichloropyrimidin-4-yl)methoxy)-[1,2,4]triazolo[4,3-a]pyridine

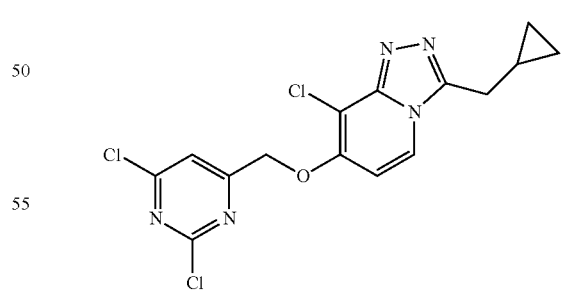

The titled compound (6.6 mg, 5% yield) was prepared from 3-(cyclopropylmethyl)-8-(trifluoromethyl)-[1,2,4]triazolo[4,3-a]pyridin-7-ol (from preparation AAD) and 2,4-dichloro-6-(chloromethyl)pyrimidine (commercially available) following a procedure analogous to that described in example 76.

Example 83

3-(Cyclopropylmethyl)-7-(2,2-difluoro-2-phenylethoxy)-8-(trifluoromethyl)-[1,2,4]triazolo[4,3-a]pyridine

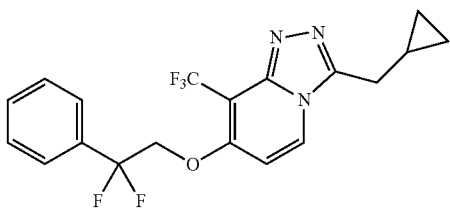 [SMILES: FC(F)(F)c1c(OCC(F)(F)c2ccccc2)ccn2c(CC3CC3)nnc12]

The titled compound (59 mg, 17% yield over 2 steps) was prepared from 4-(2,2-difluoro-2-phenylethoxy)-2-hydrazinyl-3-(trifluoromethyl)pyridine (from preparation AAK) following procedures analogous to steps 1A and 1B. The final product was purified by silica gel column chromatography (100% ethyl acetate) and reverse phase preparatory HPLC.

Example 84

3-(Cyclopropylmethyl)-7-(2-fluoro-2-phenylethoxy)-8-(trifluoromethyl)-[1,2,4]triazolo[4,3-a]pyridine

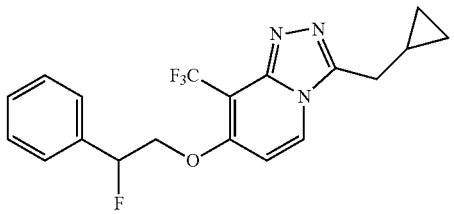 [SMILES: FC(COc1ccn2c(CC3CC3)nnc2c1C(F)(F)F)c1ccccc1]

The titled compound (69 mg, 18% yield over 2 steps) was prepared from 4-(2-fluoro-2-phenylethoxy)-2-hydrazinyl-3-(trifluoromethyl)pyridine (from preparation AAM) following procedures analogous to steps 1A and 1B. The final product was purified by silica gel column chromatography (100% ethyl acetate) and reverse phase preparatory HPLC.

Example 85

7-(Benzyloxy)-3-(cyclopropylmethyl)-8-(trifluoromethyl)-[1,2,4]triazolo[4,3-a]pyridine

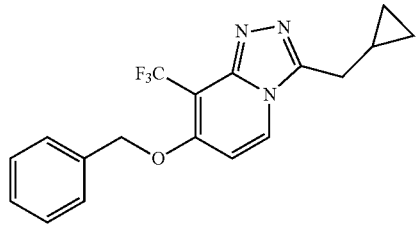 [SMILES: FC(F)(F)c1c(OCc2ccccc2)ccn2c(CC3CC3)nnc12]

The titled compound (60 mg, 28% yield over 2 steps) was prepared from 4-(2-fluoro-2-phenylethoxy)-2-hydrazinyl-3-(trifluoromethyl)pyridine (from J. Med. Chem. 2012, 55, 8770) following procedures analogous to steps 1A and 1B. The final product was purified by silica gel column chromatography (100% ethyl acetate).

Example 86

(±)-3-(2,2-Difluorocyclopropyl)-7-((1s,4s)-4-(4-fluorophenyl)-4-methoxycyclohexyloxy)-8-(trifluoromethyl)-[1,2,4]triazolo[4,3-a]pyridine

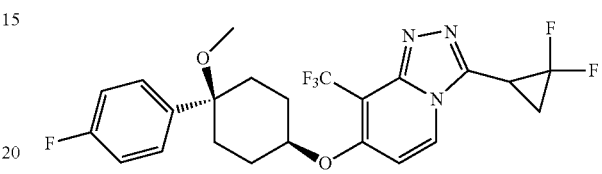

Step 86A

A solution of N-ethyldiisopropylamine (0.424 mL, 2.429 mmol) in DMF (5 mL) was added to vessel charged with 4-(((1s,4s)-4-(4-fluorophenyl)-4-methoxycyclohexyl)oxy)-2-hydrazinyl-3-(trifluoromethyl)pyridine (194 mg, 0.486 mmol, from preparation S), 2,2-difluorocyclopropanecarboxylic acid (59.3 mg, 0.486 mmol, commercially available), and 1-ethyl-3-(3-dimethylaminopropyl)carbodiimide hydrochloride (233 mg, 1.214 mmol). The flask containing the resulting mixture was stoppered and left to stir at room temperature for 18 hours. The crude reaction mixture was poured into water and extracted with EtOAc. Hexane (~5% total volume) was added to the combined organics. The organic layer was washed with brine, dried over sodium sulfate, filtered, and concentrated in vacuo. The crude product was purified using silica gel column chromatography (100% EtOAc) to afford 2,2-difluoro-N'-(4-(((1s,4s)-4-(4-fluorophenyl)-4-methoxycyclohexyl)oxy)-3-(trifluoromethyl)pyridin-2-yl)cyclopropanecarbohydrazide (129 mg, 0.256 mmol, 53% yield) off-white foam solid. LC-MS $(M+H)^+$ 504.2.

Step 86B

A mixture of 2,2-difluoro-N'-(4-(((1s,4s)-4-(4-fluorophenyl)-4-methoxycyclohexyl)oxy)-3-(trifluoromethyl)pyridin-2-yl)cyclopropanecarbohydrazide (129 mg, 0.256 mmol), Burgess reagent (130 mg, 0.547 mmol), acetonitrile (2 mL), and dioxane (2 mL) was heated at 85° C. in a sealed vial for 18 h. After cooling to rt, the reaction mixture was evaporated in vacuo and the residue was partitioned between water and ethyl acetate. The aqueous layer was extracted with ethyl acetate, and the combined organic layers were washed with brine, dried over magnesium sulfate, filtered and concentrated in vacuo. The crude product was purified using silica gel column chromatography (100% EtOAc) to afford 3-(2,2-difluorocyclopropyl)-7-((1s,4s)-4-(4-fluorophenyl)-4-methoxycyclohexyloxy)-8-(trifluoromethyl)-[1,2,4]triazolo[4,3-a]pyridine (108 mg, 85% yield) as a white solid.

Examples 87 and 88

3-((R)-2,2-Difluorocyclopropyl)-7-((1s,4s)-4-(4-fluorophenyl)-4-methoxycyclohexyloxy)-8-(trifluoromethyl)-[1,2,4]triazolo[4,3-a]pyridine, TFA salt and 3-((S)-2,2-Difluorocyclopropyl)-7-((1s,4s)-4-(4-fluorophenyl)-4-methoxycyclohexyloxy)-8-(trifluoromethyl)-[1,2,4]triazolo[4,3-a]pyridine, TFA salt

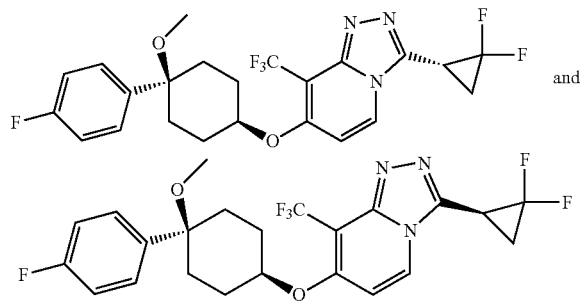

A sample of (±)-3-(2,2-difluorocyclopropyl)-7-((1s,4s)-4-(4-fluorophenyl)-4-methoxycyclohexyloxy)-8-(trifluoromethyl)-[1,2,4]triazolo[4,3-a]pyridine (example 86, 61 mg) was purified using chiral HPLC to afford the separated enantiomers. Each enantiomer was separately repurified using reverse phase preparatory HPLC to afford 21 mg of example 87 (TFA salt, first to elute from chiral column) and 16 mg of example 87 (TFA salt, second to elute from chiral column). Chiral HPLC Method: ChiralPak OD (21×250 mm, 10 uM), 10% ethanol/90% heptane (with 0.1% diethylamine), 15 mL/min, absorbance 220 nm. The absolute stereochemistry of the individual enantiomers was not determined.

Example 89

(±)-rel-3-((1S,2R)-2-Fluorocyclopropyl)-7-((1s,4s)-4-(4-fluorophenyl)-4-methoxycyclohexyloxy)-8-(trifluoromethyl)-[1,2,4]triazolo[4,3-a]pyridine

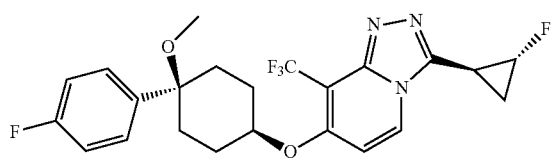 [SMILES: CO[C@]1(c2ccc(F)cc2)CC[C@H](Oc2ccn3c([C@@H]4C[C@H]4F)nnc3c2C(F)(F)F)CC1]

The titled compound (136 mg, 46% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) and commercially available trans-2-fluorocyclopropanecarboxylic acid following procedures analogous to steps 86A and 86B. The final product was purified using silica gel column chromatography (100% EtOAc).

Examples 90 and 91

3-((1R,2S)-2-Fluorocyclopropyl)-7-((1s,4s)-4-(4-fluorophenyl)-4-methoxycyclohexyloxy)-8-(trifluoromethyl)-[1,2,4]triazolo[4,3-a]pyridine and 3-((1S,2R)-2-Fluorocyclopropyl)-7-((1s,4s)-4-(4-fluorophenyl)-4-methoxycyclohexyloxy)-8-(trifluoromethyl)-[1,2,4]triazolo[4,3-a]pyridine

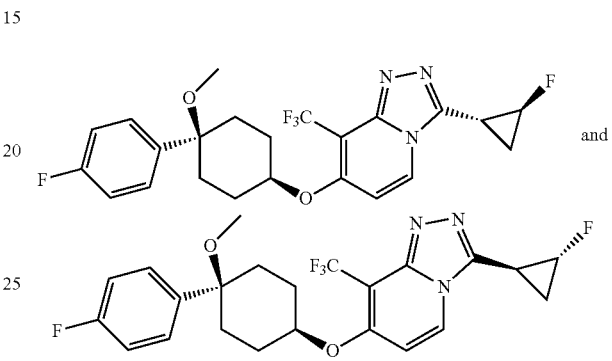

A sample of (±)-rel-3-((1S,2R)-2-fluorocyclopropyl)-7-((1s,4s)-4-(4-fluorophenyl)-4-methoxycyclohexyloxy)-8-(trifluoromethyl)-[1,2,4]triazolo[4,3-a]pyridine (example 89, 60 mg) was purified using chiral HPLC to afford 14 mg of example 90 (first to elute) and 17 mg of example 91 (second to elute from chiral column). Chiral HPLC Method: ChiralPak AS (21×250 mm, 10 uM), 10% ethanol/90% heptane (with 0.1% diethylamine), 15 mL/min, absorbance 220 nm. The absolute stereochemistry of individual enantiomers was not determined. The absolute stereochemistry of the individual enantiomers was not determined.

Example 92

3-Cyclopropyl-7-((1s,4s)-4-(4-fluorophenyl)-4-methoxycyclohexyloxy)-8-(trifluoromethyl)-[1,2,4]triazolo[4,3-a]pyridine

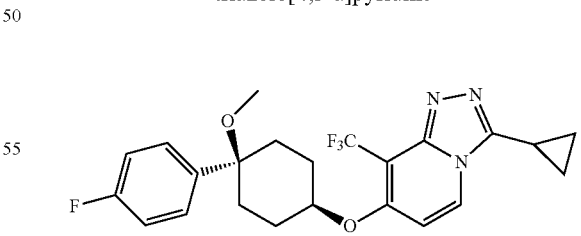

The titled compound (37 mg, 33% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) and commercially available cyclopropanecarboxylic acid following procedures analogous to steps 86A and 86B. The final product was purified using preparative LC-MS under the standard conditions.

Example 93

3-(3,3-Difluorocyclobutyl)-7-((1s,4s)-4-(4-fluorophenyl)-4-methoxycyclohexyloxy)-8-(trifluoromethyl)-[1,2,4]triazolo[4,3-a]pyridine

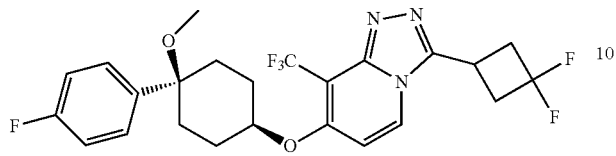

The titled compound (57 mg, 44% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) and commercially available 3,3-difluorocyclobutanecarboxylic acid following procedures analogous to steps 86A and 86B. The final product was purified using preparative LC-MS under the standard conditions.

Example 94

3-(2,2-Dimethylcyclopropyl)-7-((1s,4s)-4-(4-fluorophenyl)-4-methoxycyclohexyloxy)-8-(trifluoromethyl)-[1,2,4]triazolo[4,3-a]pyridine

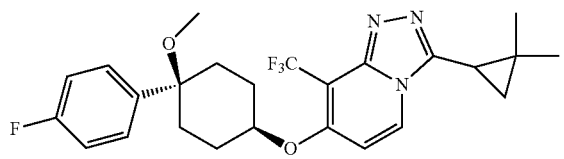 [SMILES: CO[C@]1(c2ccc(F)cc2)CC[C@H](Oc2ccn3c(C4CC4(C)C)nnc3c2C(F)(F)F)CC1]

The titled compound (16 mg, 18% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) and commercially available 2,2-dimethylcyclopropanecarboxylic acid following procedures analogous to steps 86A and 86B. The final product was purified using preparative LC-MS under the standard conditions.

Example 95

(1s,4s)-4-(3-(Cyclopropylmethyl)-8-(trifluoromethyl)-[1,2,4]triazolo[4,3-a]pyridin-7-yloxy)-1-(4-fluorophenyl)cyclohexanol, TFA salt

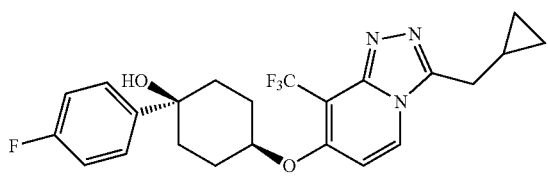 [SMILES: O[C@]1(c2ccc(F)cc2)CC[C@H](Oc2ccn3c(CC4CC4)nnc3c2C(F)(F)F)CC1]

The titled compound (16 mg, 4% yield over 2 steps) was prepared from (1s,4s)-1-(4-fluorophenyl)-4-(2-hydrazinyl-3-(trifluoromethyl)pyridin-4-yloxy)cyclohexanol (from preparation AAO) following procedures analogous to steps 1A and 1B. The final product was purified using silica gel column chromatography (100% EtOAc) and further purified using reverse phase preparatory HPLC under the standard conditions.

Example 96

3-(Cyclopropylmethyl)-7-((1r,3r)-3-(4-fluorophenyl)cyclobutoxy)-8-(trifluoromethyl)-[1,2,4]triazolo[4,3-a]pyridine

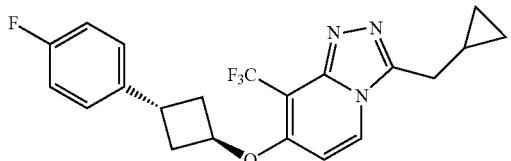

The titled compound (103 mg, 38% yield over 2 steps) was prepared from 4-((1r,3r)-3-(4-fluorophenyl)cyclobutoxy)-2-hydrazinyl-3-(trifluoromethyl)pyridine (from preparation AAQ) following procedures analogous to steps 1A and 1B. The final product was purified using silica gel column chromatography (100% EtOAc).

Example 97

7-((1s,4s)-4-(4-Fluorophenyl)-4-methoxycyclohexyloxy)-3-(2,2,2-trifluoroethyl)-8-(trifluoromethyl)-[1,2,4]triazolo[4,3-a]pyridine

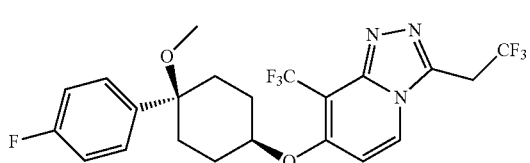

The titled compound (28 mg, 22% yield over 2 steps) was prepared from 4-(((1s,4s)-4-(4-fluorophenyl)-4-methoxycyclohexyl)oxy)-2-hydrazinyl-3-(trifluoromethyl)pyridine (from preparation S) and 3,3,3-trifluoropropanoyl chloride (commercially available) following procedures analogous to steps 1A and 1B. The final product was purified using silica gel column chromatography (100% EtOAc).

Example 98

(±)-3-(2,2-Difluorocyclopropyl)-7-((1r,3r)-3-(4-fluorophenyl)cyclobutoxy)-8-(trifluoromethyl)-[1,2,4]triazolo[4,3-a]pyridine

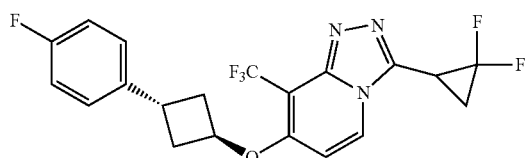

The titled compound (24 mg, 34% yield over 2 steps) was prepared from 4-((1r,3r)-3-(4-fluorophenyl)cyclobutoxy)-2-hydrazinyl-3-(trifluoromethyl)pyridine (from preparation AAQ) and commercially available 2,2-difluorocyclopropanecarboxylic acid following procedures analogous to steps 86A and 86B. The final product was purified using silica gel column chromatography (100% EtOAc).

Example 99

3-(Cyclopropylmethyl)-7-((1s,4s)-4-(4-fluorophenyl)-4-(methoxy-d₃)cyclohexyloxy)-8-(trifluoromethyl)-[1,2,4]triazolo[4,3-a]pyridine

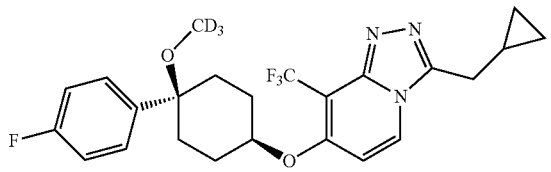 [SMILES: [2H]C([2H])([2H])O[C@]1(c2ccc(F)cc2)CC[C@H](Oc2ccn3c(CC4CC4)nnc3c2C(F)(F)F)CC1]

The titled compound (59 mg, 18% yield over 2 steps) was prepared from 4-((1s,4s)-4-(4-fluorophenyl)-4-(methoxy-d₃)cyclohexyloxy)-2-hydrazinyl-3-(trifluoromethyl)pyridine (from preparation AAR) following procedures analogous to steps 1A and 1B. The final product was purified using silica gel column chromatography (100% EtOAc) and further purified using reverse phase preparatory HPLC under the standard conditions. The resulting TFA salt was free based by dissolving the purified product in aqueous sodium bicarbonate solution, extracting with ethyl acetate, and reconcentrating the organic extract.

Example 100

(1s,3s)-3-(3-(Cyclopropylmethyl)-8-(trifluoromethyl)-[1,2,4]triazolo[4,3-a]pyridin-7-yloxy)-1-(3,5-(di-³H)-2-methoxyphenyl)cyclobutanecarbonitrile

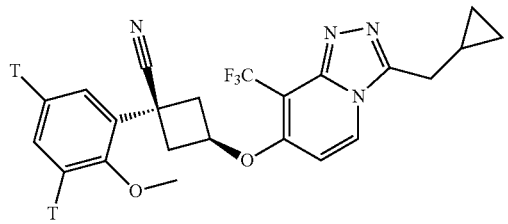

Step 100A

To a solution of (1s,3s)-3-((3-(cyclopropylmethyl)-8-(trifluoromethyl)-[1,2,4]triazolo[4,3-a]pyridin-7-yl)oxy)-1-(2-methoxyphenyl)cyclobutanecarbonitrile (10 mg, 0.023 mmol, example 53) in acetonitrile (1.0 mL) was added neat bromine (0.058 mL, 1.13 mmol). The mixture was stirred at 45° C. for 12 h. The resulting mixture was concentrated in vacuo and purified using preparatory LC-MS under the standard conditions to afford (1s,3s)-3-(3-(cyclopropylmethyl)-8-(trifluoromethyl)-[1,2,4]triazolo[4,3-a]pyridin-7-yloxy)-1-(3,5-dibromo-2-methoxyphenyl)cyclobutanecarbonitrile (7.5 mg, 51% yield). LC-MS (M+H)⁺ 601.1. ¹H NMR (500 MHz, DMSO-d₆) δ 8.66 (d, J=7.6 Hz, 1H), 8.01-7.94 (m, 1H), 7.71 (s, 1H), 6.95 (d, J=7.9 Hz, 1H), 5.20-5.03 (m, 1H), 3.95 (s, 3H), 3.08-2.97 (m, 4H), 1.23-1.11 (m, 1H), 0.56-0.45 (m, 2H), 0.27 (d, J=4.6 Hz, 2H).

Step 100B

A solution of (1s,3s)-3-(3-(cyclopropylmethyl)-8-(trifluoromethyl)-[1,2,4]triazolo[4,3-a]pyridin-7-yloxy)-1-(3,5-dibromo-2-methoxyphenyl)cyclobutanecarbonitrile (1.4 mg, 2.57 μmol, from step 100A) and triethylamine (0.040 ml) in 0.5 ml ethanol was added to 10% palladium on carbon (4.0 mg). The mixture was exposed to 1 Ci of tritium gas and vigorously stirred at ambient temperature for 4.2 h. The catalyst was removed by filtration and the crude product was twice concentrated by rotary evaporation with added ethanol (3×2 ml). The residue was dissolved in 5 ml of ethanol. The solution of the crude product was assayed by scintillation counting and was found to contain 58 mCi radioactivity. The crude product was purified using preparatory HPLC (column: LUNA 5μ, C18(2) (10×250 mm); solvent A: CH₃CN/H₂O=40/60(0.1% TFA); solvent B: CH₃CN; lambda=224 nm; method: 0-5 min 0% B@1 ml/min; 5-6 min 0% B@1-4.5 ml/min; 6-30 min 0% B 4.5 ml/min; 30-35 min 0-100% B at 4.5 ml/min) to afford a sample of the titled compound having 93.7% radiochemical purity. The sample was repurified by preparatory HPLC (column: LUNA 5u C18(2)(10× 250 mm); solvent A: CH₃CN/H₂O=30/70 (0.1% TFA); solvent B: CH₃CN; lambda=224 nm; 0-5 min 0% B@1 ml/min; 5-6 min 0% B@1-4.5 ml/min; 6-66 min 0% B@4.5 ml/min; 66-70 min 0-100% B at 4.5 ml/min) to afford a sample of the titled compound having 99.5% radiochemical purity. S.A.=38.0 Ci/mmol. MS m/z (441.00-451.92) average=446.08.

TABLE 2

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 1 | (cyclopropylmethyl) | —CF₃ | (1-phenylcyclohexylmethyl) | achiral/ free base | 430.2 |

¹H NMR (500 MHz, DMSO-d₆) δ 8.62 (d, J = 7.8 Hz, 1H), 7.48 (d, J = 7.5 Hz, 2H), 7.35 (t, J = 7.8 Hz, 2H), 7.26-7.16 (m, 1H), 7.09 (d, J = 7.8 Hz, 1H), 4.22 (s, 2H), 3.01 (d, J = 6.9 Hz, 2H), 2.23 (d, J = 13.9 Hz, 2H), 1.89-1.74 (m, 2H), 1.66-1.44 (m, 3H), 1.43-1.24 (m, 3H), 1.22-1.04 (m, 1H), 0.56-0.42 (m, 2H), 0.31-0.17 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 2 | cyclopropylmethyl | —CF₃ | 4-Cl-phenyl-C(CH₃)₂-CH₂- | achiral/ free base | 424.2 |

¹H NMR (500 MHz, chloroform-d) δ 8.06 (d, J = 7.6 Hz, 1H), 7.46-7.36 (m, 2H), 7.36-7.29 (m, 2H), 6.72 (d, J = 7.8 Hz, 1H), 4.10 (s, 2H), 3.06 (d, J = 6.7 Hz, 2H), 1.53 (s, 6H), 1.21-1.08 (m, 1H), 0.70-0.55 (m, 2H), 0.32 (q, J = 5.0 Hz, 2H).

| 3 | cyclopropylmethyl | —CN | (1S,2S)-2-(4-F-phenyl)cyclopropylmethyl | (1S,2S)/ free base | 363.1 |

¹H NMR (500 MHz, methanol-d₄) δ 8.59 (d, J = 7.8 Hz, 1H), 7.22-7.14 (m, 3H), 6.98 (t, J = 8.8 Hz, 2H), 4.51 (dd, J = 10.4, 6.7 Hz, 1H), 4.39 (dd, J = 10.3, 7.4 Hz, 1H), 3.06 (d, J = 7.0 Hz, 2H), 2.16-2.07 (m, 1H), 1.61 (td, J = 6.8, 4.7 Hz, 1H), 1.28-1.19 (m, 1H), 1.18-1.09 (m, 2H), 0.68-0.58 (m, 2H), 0.38-0.30 (m, 2H).

| 4 | cyclopropylmethyl | —CF₃ | 4-F-phenyl-CH(CH₃)-CH₂- | racemate/ TFA salt | 394.1 |

¹H NMR (500 MHz, methanol-d₄) δ 8.52 (d, J = 7.8 Hz, 1H), 7.44-7.28 (m, 2H), 7.14 (d, J = 7.9 Hz, 1H), 7.10-6.98 (m, 2H), 4.49-4.29 (m, 2H), 3.40-3.20 (m, 1H), 3.05 (d, J = 6.9 Hz, 2H), 1.44 (d, J = 7.0 Hz, 3H), 1.27-1.14 (m, 1H), 0.67-0.53 (m, 2H), 0.40-0.26 (m, 2H).

| 5 | cyclopropylmethyl | —CF₃ | 2-F-6-Cl-phenyl-CH(CH₃)-CH₂- | racemate/ free base | 428.1 |

¹H NMR (500 MHz, chloroform-d) δ 8.14 (d, J = 7.6 Hz, 1H), 7.25-7.14 (m, 2H), 6.98 (ddd, J = 11.1, 8.1, 1.3 Hz, 1H), 6.86 (d, J = 7.8 Hz, 1H), 4.55-4.44 (m, 2H), 4.05 (sxt, J = 7.1 Hz, 1H), 3.08 (d, J = 6.7 Hz, 2H), 1.49 (dd, J = 7.1, 1.1 Hz, 3H), 1.21-1.11 (m, 1H), 0.67-0.59 (m, 2H), 0.33 (q, J = 4.9 Hz, 2H).

| 6 | cyclopropylmethyl | —CF₃ | 4-F-phenyl-C(CH₃)₂-CH₂- | achiral/ free base | 408.2 |

¹H NMR (500 MHz, DMSO-d₆) δ 8.66 (d, J = 7.6 Hz, 1H), 7.50 (dd, J = 8.5, 5.5 Hz, 2H), 7.23-7.07 (m, 3H), 4.33 (s, 2H), 3.02 (d, J = 7.0 Hz, 2H), 1.40 (s, 6H), 1.15 (br. s., 1H), 0.49 (d, J = 6.4 Hz, 2H), 0.25 (d, J = 4.0 Hz, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 7 | —CH₂CF₃ | —CF₃ | 4-Cl-C₆H₄-C(CH₃)₂-CH₂— | achiral/ free base | 452.1 |

¹H NMR (500 MHz, chloroform-d) δ 8.08 (d, J = 7.8 Hz, 1H), 7.42-7.30 (m, 4H), 6.81 (d, J = 7.8 Hz, 1H), 4.11 (s, 2H), 4.05 (q, J = 9.8 Hz, 2H), 1.52 (s, 6H).

| 8 | cyclopropylmethyl | —CF₃ | 4-F-C₆H₄-O-C(CH₃)₂-CH₂— | achiral/ free base | 424.1 |

¹H NMR (500 MHz, chloroform-d) δ 8.15 (d, J = 7.6 Hz, 1H), 7.02-6.93 (m, 4H), 6.92 (d, J = 7.6 Hz, 1H), 4.19 (s, 2H), 3.09 (d, J = 6.7 Hz, 2H), 1.43 (s, 6H), 1.24-1.09 (m, 1H), 0.69-0.59 (m, 2H), 0.39-0.29 (m, 2H).

| 9 | cyclopropylmethyl | —CF₃ | 2-F-6-Cl-C₆H₃-CH(CH₃)-CH₂— | enantiomer A/ free base | 428.2 |

¹H NMR (500 MHz, DMSO-d₆) δ 8.68 (d, J = 7.3 Hz, 1H), 7.37-7.28 (m, 2H), 7.26 (d, J = 7.6 Hz, 1H), 7.23-7.13 (m, J = 4.3 Hz, 1H), 4.68-4.52 (m, 2H), 3.98-3.84 (m, 1H), 3.03 (d, J = 6.7 Hz, 2H), 1.37 (d, J = 7.0 Hz, 3H), 1.20-1.11 (m, 1H), 0.53-0.46 (m, J = 6.7 Hz, 2H), 0.30-0.21 (m, J = 4.3 Hz, 2H).

| 10 | cyclopropylmethyl | —CF₃ | 2-F-6-Cl-C₆H₃-CH(CH₃)-CH₂— | enantiomer B/ free base | 428.2 |

¹H NMR data identical to example 9.

| 11 | —CH₂CF₃ | —CF₃ | 4-F-C₆H₄-O-C(CH₃)₂-CH₂— | achiral/ free base | 452.1 |

¹H NMR (500 MHz, chloroform-d) δ 8.16 (d, J = 7.8 Hz, 1H), 7.03-6.88 (m, 5H), 4.22 (s, 2H), 4.08 (q, J = 9.8 Hz, 2H), 1.43 (s, 6H).

TABLE 2-continued

Analytical data for examples 1-99.

| Ex. No. | R¹ | R² | R³ | stereochem./ salt form | [M + H]⁺ observed |
|---|---|---|---|---|---|
| 12 | -CH₂-cyclopropyl | —CF₃ | 4-F-C₆H₄-C(CH₃)(CN)-CH₂- | racemic/ TFA salt | 419.2 |

¹H NMR (500 MHz, chloroform-d) δ 8.50 (d, J = 6.6 Hz, 1H), 7.55 (dd, J = 8.7, 4.9 Hz, 2H), 7.20 (d, J = 6.0 Hz, 1H), 7.15 (t, J = 8.5 Hz, 2H), 4.60-4.39 (m, 2H), 3.11 (d, J = 6.7 Hz, 2H), 1.94 (s, 3H), 1.23-1.10 (m, 1H), 0.71-0.60 (m, 2H), 0.35 (q, J = 5.0 Hz, 2H).

| 13 | -CH₂-cyclopropyl | —CF₃ | 4-Cl-C₆H₄-O-C(CH₃)₂-CH₂- | achiral/ free base | 440.1 |

¹H NMR (500 MHz, chloroform-d) δ 8.14 (br. s., 1H), 7.26-7.22 (m, 2H), 6.99-6.92 (m, 2H), 6.90 (d, J = 7.5 Hz, 1H), 4.19 (s, 2H), 3.09 (d, J = 6.7 Hz, 2H), 1.44 (s, 6H), 1.23-1.09 (m, 1H), 0.69-0.58 (m, 2H), 0.34 (q, J = 5.0 Hz, 2H).

| 14 | -CH₂-cyclopropyl | —CF₃ | 4-F-C₆H₄-C(CH₃)(CN)-CH₂- | enantiomer A/ free base | 419.2 |

¹H NMR (500 MHz, DMSO-d₆) δ 8.74 (d, J = 7.6 Hz, 1H), 7.73-7.62 (m, 2H), 7.32 (t, J = 8.7 Hz, 2H), 7.19 (d, J = 7.6 Hz, 1H), 4.83-4.64 (m, 2H), 3.05 (d, J = 6.7 Hz, 2H), 1.83 (s, 3H), 1.22-1.12 (m, 1H), 0.55-0.43 (m, J = 7.6 Hz, 2H), 0.33-0.20 (m, J = 4.3 Hz, 2H).

| 15 | -CH₂-cyclopropyl | —CF₃ | 4-F-C₆H₄-C(CH₃)(CN)-CH₂- | enantiomer B/ free base | 419.2 |

¹H NMR data identical to example 14.

| 16 | -CH₂-cyclopropyl | —CF₃ | 2,4-diF-C₆H₃-O-C(CH₃)₂-CH₂- | achiral/ free base | 442.1 |

¹H NMR (500 MHz, chloroform-d) δ 8.13 (d, J = 7.5 Hz, 1H), 7.05 (td, J = 9.1, 5.6 Hz, 1H), 6.93 (d, J = 7.6 Hz, 1H), 6.86 (ddd, J = 10.8, 8.2, 3.1 Hz, 1H), 6.80 (dddd, J = 9.1, 7.7, 3.0, 1.6 Hz, 1H), 4.25 (s, 2H), 3.09 (d, J = 6.7 Hz, 2H), 1.45 (s, 6H), 1.23-1.10 (m, 1H), 0.70-0.57 (m, 2H), 0.34 (q, J = 4.9 Hz, 2H).

TABLE 2-continued

Analytical data for examples 1-99.

| Ex. No. | R¹ | R² | R³ | stereochem./ salt form | [M + H]⁺ observed |
|---|---|---|---|---|---|
| | ¹H NMR data | | | | |
| 17 | cyclopropylmethyl | —CF₃ | 1-(4-fluorophenyl)-4-cyano-cyclohexyl | achiral/ free base | 459.2 |

¹H NMR (500 MHz, chloroform-d) δ 8.21 (d, J = 7.6 Hz, 1H), 7.54-7.45 (m, 2H), 7.17-7.08 (m, 2H), 6.99 (d, J = 7.2 Hz, 1H), 4.61-4.49 (m, 1H), 3.09 (d, J = 6.7 Hz, 2H), 2.41-2.17 (m, 6H), 2.08-1.95 (m, 2H), 1.23-1.13 (m, 1H), 0.70-0.61 (m, 2H), 0.39-0.30 (m, 2H).

| 18 | ethoxyethyl | —CF₃ | 2-(4-chlorophenoxy)-2-methylpropyl | achiral (1s,4s)/ free base | 444.2 |

¹H NMR (500 MHz, DMSO-d₆) δ 8.67 (d, J = 7.6 Hz, 1H), 7.40-7.27 (m, 3H), 7.01 (d, J = 8.5 Hz, 2H), 4.98 (s, 2H), 4.34 (s, 2H), 3.52 (q, J = 7.0 Hz, 2H), 1.37 (s, 6H), 1.11 (t, J = 7.0 Hz, 3H).

| 19 | cyclopropylmethyl | —CF₃ | 1-(4-fluorophenyl)-4-methoxy-cyclohexyl | achiral (1s,4s)/ free base | 464.2 |

¹H NMR (500 MHz, chloroform-d) δ 8.06 (d, J = 7.8 Hz, 1H), 7.38 (dd, J = 8.8, 5.4 Hz, 2H), 7.06 (t, J = 8.6 Hz, 2H), 6.81 (d, J = 7.8 Hz, 1H), 4.51-4.38 (m, 1H), 3.07 (d, J = 6.7 Hz, 2H), 2.99 (s, 3H), 2.22 (d, J = 12.4 Hz, 2H), 2.17-2.07 (m, 2H), 2.05-1.95 (m, 2H), 1.78 (td, J = 13.4, 3.4 Hz, 2H), 1.22-1.11 (m, 1H), 0.70-0.57 (m, 2H), 0.34 (q, J = 5.0 Hz, 2H).

| 20 | cyclopropylmethyl | —CF₃ | 4-phenylcyclohexyl | achiral (1r,4r)/ free base | 416.2 |

¹H NMR (500 MHz, chloroform-d) δ 8.07 (d, J = 7.6 Hz, 1H), 7.39-7.29 (m, 2H), 7.26-7.17 (m, 3H), 6.84 (d, J = 7.8 Hz, 1H), 4.54-4.42 (m, 1H), 3.07 (d, J = 6.7 Hz, 2H), 2.64 (tt, J = 12.0, 3.5 Hz, 1H), 2.32-2.22 (m, 2H), 2.14-2.03 (m, 2H), 1.86-1.74 (m, 2H), 1.71-1.56 (m, 2H), 1.22-1.12 (m, 1H), 0.70-0.56 (m, 2H), 0.40-0.27 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 21 | cyclopropylmethyl | —CF₃ | 4-F-phenyl-C(CH₃)(OCH₃)-CH₂- | racemate/ free base | 424.1 |

¹H NMR (500 MHz, chloroform-d) δ 8.02 (d, J = 7.8 Hz, 1H), 7.51-7.40 (m, 2H), 7.14-7.02 (m, 2H), 6.75 (d, J = 7.6 Hz, 1H), 4.21 (d, J = 9.3 Hz, 1H), 4.07 (d, J = 9.3 Hz, 1H), 3.18 (s, 3H), 3.05 (d, J = 6.7 Hz, 2H), 1.79 (s, 3H), 1.19-1.06 (m, 1H), 0.66-0.57 (m, 2H), 0.31 (q, J = 4.9 Hz, 2H).

| 22 | -CH₂-O-CH₂CF₃ | —CF₃ | 4-Cl-phenyl-O-C(CH₃)₂-CH₂- | achiral/ TFA salt | 498.2 |

¹H NMR (500 MHz, methanol-d₄) δ 8.69 (d, J = 7.8 Hz, 1H), 7.43 (d, J = 7.8 Hz, 1H), 7.30-7.22 (m, 2H), 7.04-6.97 (m, 2H), 5.25 (s, 2H), 4.40 (s, 2H), 4.10 (q, J = 8.8 Hz, 2H), 1.45 (s, 6H).

| 23 | -CH₂-O-CH₃ | —CF₃ | 4-Cl-phenyl-O-C(CH₃)₂-CH₂- | achiral/ TFA salt | 430.1 |

¹H NMR (500 MHz, methanol-d₄) δ 8.81 (d, J = 7.8 Hz, 1H), 7.53 (d, J = 7.9 Hz, 1H), 7.32-7.21 (m, 2H), 7.06-6.95 (m, 2H), 5.02 (s, 2H), 4.46 (s, 2H), 3.45 (s, 3H), 1.45 (s, 6H).

| 24 | cyclopropylmethyl | —CF₃ | 4-F-phenyl-C(CH₃)(OCH₃)-CH₂- | enantiomer A/ free base | 424.3 |

¹H NMR (500 MHz, DMSO-d₆) δ 8.66 (d, J = 7.6 Hz, 1H), 7.51 (d, J = 5.8 Hz, 2H), 7.26-7.15 (m, 3H), 4.49-4.32 (m, 2H), 3.06 (s, 3H), 3.02 (d, J = 6.7 Hz, 2H), 1.65 (s, 3H), 1.15 (br. s., 1H), 0.49 (d, J = 7.3 Hz, 2H), 0.30-0.20 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| 25 | cyclopropylmethyl | —CF₃ | 4-fluorophenyl, methoxy, methyl substituted | enantiomer B/ free base | 424.3 |

¹H NMR data identical to example 24.

| 26 | cyclopropylmethyl | —CF₃ | 3,4-difluorophenyl, hydroxy-cyclohexyl | achiral (1s,4s)/ TFA salt | 468.2 |

¹H NMR (500 MHz, methanol-$d_4$) δ 8.89 (d, J = 7.9 Hz, 1H), 7.71 (d, J = 7.8 Hz, 1H), 7.44 (ddd, J = 12.4, 7.8, 2.3 Hz, 1H), 7.38-7.29 (m, 1H), 7.23 (dt, J = 10.4, 8.5 Hz, 1H), 5.08-4.98 (m, 1H), 3.13 (d, J = 6.9 Hz, 2H), 2.25-2.13 (m, 2H), 2.13-2.02 (m, 4H), 1.90 (d, J = 12.2 Hz, 2H), 1.36-1.27 (m, 1H), 0.74-0.66 (m, 2H), 0.46-0.35 (m, 2H).

| 27 | —CH₂OCH₂CF | —CF₃ | phenyl-cyclohexyl | achiral (1r,4r)/ free base | 474.3 |

¹H NMR (500 MHz, methanol-$d_4$) δ 8.59 (d, J = 7.8 Hz, 1H), 7.38 (d, J = 7.8 Hz, 1H), 7.34-7.25 (m, 4H), 7.22-7.15 (m, 1H), 5.25 (s, 2H), 4.83-4.76 (m, 1H), 4.10 (q, J = 8.9 Hz, 2H), 2.74-2.59 (m, 1H), 2.37-2.24 (m, 2H), 2.09-1.96 (m, 2H), 1.85-1.68 (m, 4H).

| 28 | cyclopropylmethyl | —CF₃ | 3,4-difluorophenyl, methoxy-cyclohexyl | achiral (1s,4s)/ free base | 482.3 |

¹H NMR (500 MHz, methanol-$d_4$) δ 8.53 (d, J = 7.8 Hz, 1H), 7.39-7.31 (m, 1H), 7.30-7.19 (m, 3H), 4.76 (tt, J = 9.8, 5.0 Hz, 1H), 3.07 (d, J = 6.9 Hz, 2H), 3.02 (s, 3H), 2.18 (dd, J = 14.5, 2.7 Hz, 2H), 2.08-1.96 (m, 4H), 1.96-1.84 (m, 2H), 1.28-1.19 (m, 1H), 0.67-0.58 (m, 2H), 0.38-0.31 (m, 2H).

| 29 | cyclopropylmethyl | —CF₃ | 4-chlorophenyl-cyclopropyl | achiral/ free base | 422.0 |

¹H NMR (500 MHz, chloroform-d) δ 8.23 (d, J = 7.6 Hz, 1H), 7.46-7.40 (m, 2H), 7.04-6.97 (m, 2H), 6.77 (d, J = 7.8 Hz, 1H), 4.25 (s, 2H), 3.09 (d, J = 6.7 Hz, 2H), 1.19-1.12 (m, 1H), 1.10-1.02 (m, 4H), 0.65-0.59 (m, 2H), 0.35-0.30 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 30 | cyclopropylmethyl | —CF₃ | 1-(4-fluorophenyl)cyclopropylmethyl | achiral/ free base | 405.8 |
| | ¹H NMR (500 MHz, chloroform-d) δ 8.38 (d, J = 7.6 Hz, 1H), 7.46-7.40 (m, 2H), 7.04-6.98 (m, 2H), 6.87 (d, J = 7.8 Hz, 1H), 4.27 (s, 2H), 3.11 (d, J = 6.7 Hz, 2H), 1.16 (br. s., 1H), 1.10-1.02 (m, 4H), 0.64-0.59 (m, 2H), 0.36-0.31 (m, 2H). | | | | | |
| 31 | cyclopropylmethyl | —CF₃ | 2-(4-chlorophenyl)cyclopropylmethyl | trans, racemate/ free base | 421.8 |
| | ¹H NMR (500 MHz, DMSO-d₆) δ 8.70 (d, J = 7.8 Hz, 1H), 7.33-7.27 (m, 2H), 7.21 (d, J = 7.8 Hz, 1H), 7.16-7.11 (m, 2H), 4.46-4.40 (m, 1H), 4.33 (dd, J = 10.6, 7.2 Hz, 1H), 3.04 (d, J = 6.9 Hz, 2H), 2.08-2.01 (m, 1H), 1.60-1.51 (m, 1H), 1.22-1.14 (m, 1H), 1.13-1.07 (m, 2H), 0.54-0.48 (m, 2H), 0.30-0.25 (m, 2H). | | | | | |
| 32 | cyclopropylmethyl | —CF₃ | 2-(2-fluoro-6-methoxyphenyl)cyclopropylmethyl | trans, racemate/ free base | 436.1 |
| | ¹H NMR (400 MHz, chloroform-d) δ 8.15 (d, J = 7.8 Hz, 1H), 7.12 (td, J = 8.3, 6.5 Hz, 1H), 6.93-6.88 (m, 1H), 6.67-6.60 (m, 2H), 4.42 (dd, J = 10.3, 6.0 Hz, 1H), 4.22 (dd, J = 10.3, 6.8 Hz, 1H), 3.82 (s, 3H), 3.08 (d, J = 6.8 Hz, 2H), 1.95 (dt, J = 9.2, 5.5 Hz, 1H), 1.86 (dd, J = 8.3, 5.8 Hz, 1H), 1.35 (dt, J = 8.3, 5.5 Hz, 1H), 1.18 (tt, J = 6.5, 1.5 Hz, 1H), 1.09-1.02 (m, 1H), 0.66-0.60 (m, 2H), 0.37-0.32 (m, 2H). | | | | | |
| 33 | cyclopropylmethyl | —CF₃ | (1R,2R)-2-(4-chlorophenyl)cyclopropylmethyl | (1R,2R)/ free base | 422.2 |
| | ¹H NMR (500 MHz, DMSO-d₆) δ 8.69 (d, J = 7.6 Hz, 1H), 7.35-7.25 (m, J = 8.5 Hz, 2H), 7.20 (d, J = 7.6 Hz, 1H), 7.17-7.07 (m, J = 8.5 Hz, 2H), 4.42 (dd, J = 10.7, 6.7 Hz, 1H), 4.32 (dd, J = 10.7, 7.3 Hz, 1H), 3.03 (d, J = 7.0 Hz, 2H), 2.11-1.97 (m, 1H), 1.60-1.47 (m, 1H), 1.27-1.13 (m, 1H), 1.09 (t, J = 7.0 Hz, 2H), 0.58-0.44 (m, 2H), 0.27 (q, J = 4.7 Hz, 2H). | | | | | |
| 34 | cyclopropylmethyl | —CF₃ | (1S,2S)-2-(4-chlorophenyl)cyclopropylmethyl | (1S,2S)/ free base | 422.2 |
| | ¹H NMR data identical to example 33. | | | | | |

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 35 | cyclopropylmethyl | —CF₃ | 2-F-6-OMe-phenyl-cyclopropyl-CH₂ | trans, enantiomer A/ free base | 436.3 |

¹H NMR (500 MHz, DMSO-d₆) δ 8.68 (d, J = 7.9 Hz, 1H), 7.22 (d, J = 7.9 Hz, 1H), 7.20-7.11 (m, 1H), 6.78 (d, J = 8.2 Hz, 1H), 6.74-6.65 (m, 1H), 4.46-4.34 (m, 2H), 3.03 (d, J = 7.0 Hz, 2H), 1.99-1.90 (m, 1H), 1.83-1.72 (m, 1H), 1.25-1.10 (m, 2H), 1.00 (dt, J = 9.3, 4.8 Hz, 1H), 0.57-0.46 (m, 2H), 0.26 (q, J = 4.8 Hz, 2H)

| 36 | cyclopropylmethyl | —CF₃ | 2-F-6-OMe-phenyl-cyclopropyl-CH₂ | trans, enantiomer B/ free base | 436.3 |

¹H NMR data identical to example 35.

| 37 | cyclopropylmethyl | —CF₃ | 2-OMe-phenyl-cyclopropyl-CH₂ | trans, racemate/ free base | 418.2 |

¹H NMR (500 MHz, DMSO-d₆) δ 8.70 (d, J = 7.6 Hz, 1H), 7.24 (d, J = 7.6 Hz, 1H), 7.17-7.11 (m, 1H), 6.93 (d, J = 8.2 Hz, 1H), 6.90-6.81 (m, 2H), 4.50-4.42 (m, 1H), 4.41-4.34 (m, 1H), 3.75 (s, 3H), 3.05 (d, J = 7.0 Hz, 2H), 2.26-2.19 (m, 1H), 1.57-1.48 (m, 1H), 1.22-1.14 (m, 1H), 1.06-0.96 (m, 2H), 0.55-0.48 (m, 2H), 0.28 (q, J = 4.8 Hz, 2H).

| 38 | cyclopropylmethyl | —CF₃ | 2-OCF₃-phenyl-cyclopropyl-CH₂ | trans, racemate/ free base | 472.1 |

¹H NMR (500 MHz, chloroform-d) δ 8.11 (d, J = 7.8 Hz, 1H), 7.27-7.24 (m, 3H), 7.06-7.03 (m, 1H), 6.83 (d, J = 7.6 Hz, 1H), 4.45 (dd, J = 10.1, 5.6 Hz, 1H), 4.19 (dd, J = 10.1, 6.9 Hz, 1H), 3.09 (d, J = 6.7 Hz, 2H), 2.28-2.23 (m, 1H), 1.64-1.57 (m, 2H), 1.22-1.17 (m, 2H), 0.67-0.63 (m, 2H), 0.37-0.33 (m, 2H).

| 39 | cyclopropylmethyl | —CF₃ | 2-OMe-phenyl-cyclopropyl-CH₂ | trans, enantiomer A/ free base | 418.3 |

¹H NMR (500 MHz, DMSO-d₆) δ 8.70 (d, J = 7.6 Hz, 1H), 7.24 (d, J = 7.6 Hz, 1H), 7.17-7.11 (m, 1H), 6.93 (d, J = 8.2 Hz, 1H), 6.90-6.81 (m, 2H), 4.50-4.42 (m, 1H), 4.41-4.34 (m, 1H), 3.75 (s, 3H), 3.05 (d, J = 7.0 Hz, 2H), 2.26-2.19 (m, 1H), 1.57-1.48 (m, 1H), 1.22-1.14 (m, 1H), 1.06-0.96 (m, 2H), 0.55-0.48 (m, 2H), 0.28 (q, J = 4.8 Hz, 2H).

TABLE 2-continued

Analytical data for examples 1-99.

| Ex. No. | R¹ | R² | R³ <br> ¹H NMR data | stereochem./ salt form | [M + H]⁺ observed |
|---|---|---|---|---|---|
| 40 | cyclopropylmethyl | —CF₃ | 2-methoxyphenyl-cyclopropyl | trans, enantiomer B/ free base | 418.3 |

¹H NMR data identical to example 39.

| 41 | cyclopropylmethyl | —CF₃ | 2-(trifluoromethoxy)phenyl-cyclopropyl | trans, enantiomer A/ free base | 472.3 |

¹H NMR (500 MHz, DMSO-d₆) δ 8.71 (d, J = 7.6 Hz, 1H), 7.30 (s, 3H), 7.23 (d, J = 7.9 Hz, 1H), 7.15-7.05 (m, 1H), 4.52-4.36 (m, 2H), 3.05 (d, J = 6.7 Hz, 2H), 2.31-2.19 (m, 1H), 1.67 (br. s., 1H), 1.24-1.14 (m, 2H), 1.14-1.06 (m, 1H), 0.58-0.44 (m, 2H), 0.28 (d, J = 4.3 Hz, 2H).

| 42 | cyclopropylmethyl | —CF₃ | 2-(trifluoromethoxy)phenyl-cyclopropyl | trans, enantiomer B/ free base | 472.3 |

¹H NMR data identical to example 41.

| 43 | cyclopropylmethyl | —CF₃ | 2-fluorophenyl-cyclopropyl | trans, racemate/ free base | 406.3 |

¹H NMR (500 MHz, DMSO-d₆) δ 8.70 (d, J = 7.6 Hz, 1H), 7.26-7.18 (m, 2H), 7.15-7.04 (m, 3H), 4.43 (dd, J = 18.2, 6.9 Hz, 2H), 3.05 (d, J = 6.7 Hz, 2H), 2.18 (br. s., 1H), 1.62 (br. s., 1H), 1.18 (br. s., 1H), 1.13 (t, J = 6.9 Hz, 2H), 0.51 (d, J = 7.3 Hz, 2H), 0.28 (d, J = 4.0 Hz, 2H).

| 44 | cyclopropylmethyl | —CF₃ | 2,5-difluorophenyl-cyclopropyl | trans, racemate/ free base | 424.1 |

¹H NMR (500 MHz, DMSO-d₆) δ 8.70 (d, J = 7.6 Hz, 1H), 7.26-7.13 (m, 2H), 7.02 (t, J = 8.2 Hz, 1H), 6.92 (d, J = 6.4 Hz, 1H), 4.50-4.33 (m, 2H), 3.05 (d, J = 6.7 Hz, 2H), 2.18 (d, J = 3.7 Hz, 1H), 1.67 (br. s., 1H), 1.24-1.09 (m, 3H), 0.51 (d, J = 7.9 Hz, 2H), 0.28 (d, J = 4.3 Hz, 2H).

| 45 | cyclopropylmethyl | —CF₃ | 4-methoxyphenyl-cyclopropyl | trans, racemate/ free base | 418.1 |

¹H NMR (500 MHz, DMSO-d₆) δ 8.70 (d, J = 7.6 Hz, 1H), 7.22 (d, J = 7.9 Hz, 1H), 7.04 (d, J = 8.5 Hz, 2H), 6.82 (d, J = 8.5 Hz, 2H), 4.45-4.39 (m, 1H), 4.35-4.28 (m, 1H), 3.71 (s, 3H), 3.04 (d, J = 6.7 Hz, 2H), 2.03-1.93 (m, 1H), 1.49-1.39 (m, 1H), 1.18 (d, J = 4.9 Hz, 1H), 1.01 (t, J = 7.0 Hz, 2H), 0.56-0.46 (m, 2H), 0.30-0.23 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 46 | cyclopropylmethyl | —CF₃ | 1-(3-fluorophenyl)-3-substituted cyclobutyl with NC | trans, achiral/ free base | 431.2 |

¹H NMR (500 MHz, methanol-d₄) δ 8.56 (d, J = 7.8 Hz, 1H), 7.54 (td, J = 8.0, 6.0 Hz, 1H), 7.47-7.38 (m, 2H), 7.17 (tdd, J = 8.4, 2.5, 0.8 Hz, 1H), 7.00 (d, J = 7.8 Hz, 1H), 5.32-5.25 (m, 1H), 3.41-3.37 (m, 2H), 3.23-3.18 (m, 2H), 3.09 (d, J = 6.9 Hz, 2H), 1.30-1.21 (m, 1H), 0.67-0.61 (m, 2H), 0.38-0.33 (m, 2H).

| 47 | cyclopropylmethyl | —CF₃ | 2,5-difluoro-3-methoxyphenyl cyclopropyl | trans, racemate/ free base | 545.1 |

¹H NMR (500 MHz, DMSO-d₆) δ 8.71 (d, J = 7.9 Hz, 1H), 7.24 (d, J = 7.9 Hz, 1H), 7.14 (td, J = 10.0, 5.0 Hz, 1H), 6.90 (td, J = 9.8, 4.0 Hz, 1H), 4.44 (d, J = 6.7 Hz, 2H), 3.85 (s, 3H), 3.05 (d, J = 6.7 Hz, 2H), 2.10-2.02 (m, 1H), 1.90-1.83 (m, 1H), 1.29-1.23 (m, 1H), 1.18 (d, J = 6.4 Hz, 1H), 1.13-1.04 (m, 1H), 0.51 (d, J = 7.9 Hz, 2H), 0.28 (d, J = 4.6 Hz, 2H).

| 48 | cyclopropylmethyl | —CF₃ | 2-chloro-6-fluorophenyl cyclopropyl | trans, racemate/ free base | 440.1 |

¹H NMR (500 MHz, methanol-d₄) δ 8.88 (d, J = 7.8 Hz, 1H), 7.61 (d, J = 7.8 Hz, 1H), 7.26-7.22 (m, 2H), 7.07-7.01 (m, 1H), 4.71 (dd, J = 10.5, 6.4 Hz, 1H), 4.59 (dd, J = 10.5, 6.7 Hz, 1H), 3.14 (d, J = 6.9 Hz, 2H), 2.09-2.04 (m, 1H), 1.88-1.83 (m, 1H), 0.94-0.91 (m, 2H), 0.72-0.68 (m, 2H), 0.43-0.40 (m, 2H), 0.14-0.08 (m, 1H).

| 49 | cyclopropylmethyl | —CF₃ | 4-fluoro-2-methoxyphenyl cyclopropyl | trans, racemate/ TFA salt | 436.1 |

¹H NMR (500 MHz, DMSO-d₆) δ 8.69 (d, J = 7.6 Hz, 1H), 7.23 (d, J = 7.9 Hz, 1H), 6.91 (t, J = 7.6 Hz, 1H), 6.83 (dd, J = 11.3, 2.1 Hz, 1H), 6.65 (td, J = 8.5, 2.3 Hz, 1H), 4.48-4.31 (m, 2H), 3.75 (s, 3H), 3.04 (d, J = 7.0 Hz, 2H), 2.17-2.09 (m, 1H), 1.49 (d, J = 7.0 Hz, 1H), 1.18 (br. s., 1H), 1.04-0.94 (m, 2H), 0.55-0.47 (m, 2H), 0.28 (d, J = 4.6 Hz, 2H).

| 50 | cyclopropylmethyl | —CF₃ | 1-(4-fluorophenyl)-3-substituted cyclobutyl with NC | achiral (1s,3s)/ free base | 431.2 |

¹H NMR (500 MHz, chloroform-d) δ 8.09 (d, J = 7.6 Hz, 1H), 7.55-7.45 (m, 2H), 7.22-7.14 (m, 2H), 6.53 (d, J = 7.6 Hz, 1H), 4.98 (t, J = 6.8 Hz, 1H), 3.37-3.18 (m, 4H), 3.08 (d, J = 6.7 Hz, 2H), 1.16 (s, 1H), 0.72-0.60 (m, 2H), 0.39-0.27 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| 51 | cyclopropylmethyl | —CF₃ | 1-(2,4-difluorophenyl)cyclopropylmethyl | achiral/ free base | 424.1 |

¹H NMR (500 MHz, DMSO-d₆) δ 8.40 (d, J = 7.9 Hz, 1H), 7.20 (q, J = 8.0 Hz, 1H), 6.93 (t, J = 9.9 Hz, 1H), 6.87-6.75 (m, 2H), 4.11 (s, 2H), 2.78 (d, J = 6.7 Hz, 2H), 0.91 (br. s., 1H), 0.83 (s, 2H), 0.70 (s, 2H), 0.25 (d, J = 7.6 Hz, 2H), 0.01 (d, J = 4.9 Hz, 2H).

| 52 | CH₂CF₃ | —CF₃ | trans-2-(4-fluorophenyl)cyclopropyl | (S,S)/ free base | 434.1 |

¹H NMR (500 MHz, methanol-d₄) δ 8.68 (d, J = 7.9 Hz, 1H), 7.31 (d, J = 7.8 Hz, 1H), 7.20-7.12 (m, 2H), 7.03-6.93 (m, 2H), 4.50 (dd, J = 10.2, 6.4 Hz, 1H), 4.38-4.26 (m, 3H), 2.09 (td, J = 7.1, 4.5 Hz, 1H), 1.64-1.53 (m, 1H), 1.17-1.07 (m, 2H).

| 53 | cyclopropylmethyl | —CF₃ | 1-cyano-3-(2-methoxyphenyl)cyclobutyl | achiral (1s,3s)/ free base | 443.2 |

¹H NMR (500 MHz, methanol-d₄) δ 8.54 (d, J = 7.8 Hz, 1H), 7.49-7.40 (m, 2H), 7.13 (d, J = 7.5 Hz, 1H), 7.07 (td, J = 7.6, 0.9 Hz, 1H), 6.95 (d, J = 7.8 Hz, 1H), 5.12-5.04 (m, 1H), 3.96 (s, 3H), 3.43-3.36 (m, 2H), 3.14-3.07 (m, 4H), 1.29-1.21 (m, 1H), 0.67-0.61 (m, 2H), 0.38-0.33 (m, 2H)

| 54 | cyclopropylmethyl | —CF₃ | 1-cyano-3-(3,5-difluorophenyl)cyclobutyl | achiral (1s,3s)/ free base | 449.3 |

¹H NMR (500 MHz, DMSO-d₆) δ 8.69 (d, J = 7.9 Hz, 1H), 7.42 (d, J = 6.7 Hz, 2H), 7.35 (t, J = 9.2 Hz, 1H), 7.04 (d, J = 7.6 Hz, 1H), 5.29 (t, J = 6.0 Hz, 1H), 3.38 (d, J = 7.0 Hz, 2H), 3.09-3.02 (m, 4H), 1.18 (d, J = 5.2 Hz, 1H), 0.53 (d, J = 7.6 Hz, 2H), 0.29 (d, J = 4.6 Hz, 2H).

| 55 | cyclopropylmethyl | —CF₃ | 1-(3,5-difluorophenyl)cyclopropylmethyl | achiral/ free base | 424.3 |

¹H NMR (600 MHz, DMSO-d₆) δ 8.68 (d, J = 5.5 Hz, 1H), 7.12 (d, J = 7.7 Hz, 1H), 7.08-6.99 (m, 3H), 4.48 (s, 2H), 3.02 (d, J = 6.6 Hz, 2H), 1.19-1.12 (m, 1H), 1.12-1.04 (m, 4H), 0.55-0.42 (m, 2H), 0.32-0.19 (m, 2H).

TABLE 2-continued

Analytical data for examples 1-99.

| Ex. No. | R¹ | R² | R³ <br> ¹H NMR data | stereochem./ salt form | [M + H]⁺ observed |
|---|---|---|---|---|---|
| 56 | cyclopropylmethyl | —CF₃ | 1-(3,5-dichlorophenyl)cyclopropyl-ethyl | achiral/ free base | 456.2 |

¹H NMR (600 MHz, DMSO-d₆) δ 8.68 (d, J = 7.3 Hz, 1H), 7.44 (s, 1H), 7.42-7.36 (m, 2H), 7.10 (d, J = 7.7 Hz, 1H), 4.46 (s, 2H), 3.03 (d, J = 6.6 Hz, 2H), 1.21-1.12 (m, 1H), 1.12-1.01 (m, 4H), 0.56-0.45 (m, 2H), 0.26 (q, J = 4.8 Hz, 2H).

| 57 | cyclopropylmethyl | —CF₃ | trans-3-phenylcyclobutyl-methyl | achiral (1r,4r)/ free base | 388.4 |

¹H NMR (500 MHz, DMSO-d₆) δ 8.68 (d, J = 7.6 Hz, 1H), 7.38-7.14 (m, 5H), 7.08 (d, J = 7.6 Hz, 1H), 5.13 (t, J = 7.0 Hz, 1H), 3.25-3.13 (m, 1H), 3.12-2.88 (m, 4H), 2.17 (d, J = 8.9 Hz, 2H), 1.28-1.05 (m, 1H), 0.61-0.41 (m, 2H), 0.37-0.18 (m, 2H).

| 58 | cyclopropylmethyl | —Cl | 4-chlorobenzyl | achiral/ TFA salt | 348.4 |

¹H NMR (500 MHz, methanol-d₄) δ 8.67 (d, J = 7.6 Hz, 1H), 7.56 (d, J = 7.6 Hz, 1H), 7.54-7.49 (m, 2H), 7.48-7.41 (m, 2H), 5.53 (s, 2H), 3.11 (d, J = 6.9 Hz, 2H), 1.36-1.25 (m, 1H), 0.73-0.66 (m, 2H), 0.42-0.36 (m, 2H).

| 59 | cyclopropylmethyl | —Cl | 1-(4-fluorophenyl)ethyl | achiral/ free base | 346.4 |

¹H NMR (500 MHz, methanol-d₄) δ 8.35 (d, J = 7.6 Hz, 1H), 7.51 (dd, J = 8.7, 5.3 Hz, 2H), 7.17 (d, J = 7.8 Hz, 1H), 7.12 (t, J = 8.9 Hz, 2H), 5.86 (q, J = 5.9 Hz, 1H), 3.03 (d, J = 6.9 Hz, 2H), 1.75 (d, J = 6.4 Hz, 3H), 1.28-1.19 (m, 1H), 0.66-0.59 (m, 2H), 0.34 (q, J = 4.8 Hz, 2H).

| 60 | cyclopropylmethyl | —Cl | 3-chlorobenzyl | achiral/ free base | |

¹H NMR (500 MHz, DMSO-d₆) δ 8.51 (d, J = 7.6 Hz, 1H), 7.58 (s, 1H), 7.52-7.39 (m, 3H), 7.23 (d, J = 7.6 Hz, 1H), 5.46 (s, 2H), 3.04 (d, J = 7.0 Hz, 2H), 1.19 (s, 1H), 0.62-0.45 (m, 2H), 0.28 (d, J = 5.2 Hz, 2H).

TABLE 2-continued

Analytical data for examples 1-99.

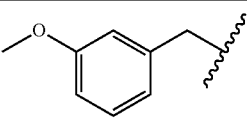

| Ex. No. | R¹ | R² | R³ | stereochem./ salt form | [M + H]⁺ observed |
|---|---|---|---|---|---|
| | | | ¹H NMR data | | |
| 61 | 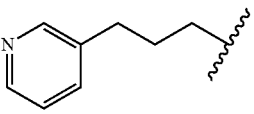 [SMILES: *CCCc1cccnc1] | —Cl | | achiral/ free base | 344.1 |

¹H NMR (500 MHz, DMSO-d₆) δ 8.48 (d, J = 7.6 Hz, 1H), 7.34 (t, J = 7.9 Hz, 1H), 7.23 (d, J = 7.6 Hz, 1H), 7.11-7.02 (m, 2H), 6.93 (dd, J = 8.2, 2.1 Hz, 1H), 5.42 (s, 2H), 3.82-3.73 (m, 3H), 3.03 (d, J = 6.7 Hz, 2H), 1.26-1.10 (m, 1H), 0.57-0.45 (m, 2H), 0.30-0.23 (m, 2H).

| 62 | | —Cl | 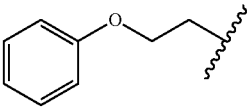 [SMILES: *CCOc1ccccc1] | achiral/ free base | 343.2 |

¹H NMR (500 MHz, DMSO-d₆) δ 8.50-8.47 (m, 2H), 8.43 (dd, J = 4.6, 1.5 Hz, 1H), 7.70 (d, J = 7.6 Hz, 1H), 7.33 (dd, J = 7.9, 4.9 Hz, 1H), 7.16 (d, J = 7.6 Hz, 1H), 4.28 (t, J = 6.3 Hz, 2H), 3.05 (d, J = 6.7 Hz, 2H), 2.86-2.78 (m, 2H), 2.14-2.05 (m, 2H), 1.24-1.14 (m, 1H), 0.55-0.49 (m, 2H), 0.31-0.25 (m, 2H).

| 63 | | —Cl | | achiral/ free base | 344.2 |

¹H NMR (500 MHz, DMSO-d₆) δ 8.52 (d, J = 7.6 Hz, 1H), 7.32 (dd, J = 8.7, 7.5 Hz, 2H), 7.26-7.23 (m, 1H), 7.01-6.95 (m, 3H), 4.65 (dd, J = 5.3, 3.5 Hz, 2H), 4.36 (dd, J = 5.3, 3.5 Hz, 2H), 3.07-3.05 (m, 2H), 1.20 (dd, J = 7.8, 4.7 Hz, 1H), 0.54-0.52 (m, 2H), 0.30-0.28 (m, 2H).

| 64 | | —Cl | 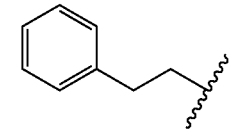 [SMILES: *CCc1ccccc1] | achiral/ free base | 328.2 |

¹H NMR (500 MHz, DMSO-d₆) δ 8.47 (d, J = 7.6 Hz, 1H), 7.41-7.31 (m, 4H), 7.28-7.22 (m, 1H), 7.19 (d, J = 7.6 Hz, 1H), 4.49 (t, J = 6.9 Hz, 2H), 3.10 (t, J = 6.9 Hz, 2H), 3.04 (d, J = 7.0 Hz, 2H), 1.23-1.12 (m, 1H), 0.54-0.48 (m, 2H), 0.30-0.24 (m, 2H).

| 65 | | —Cl | 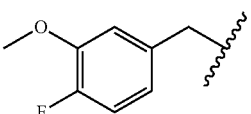 | achiral/ free base | 362.2 |

¹H NMR (500 MHz, DMSO-d₆) δ 8.49 (d, J = 7.6 Hz, 1H), 7.32 (dd, J = 8.5, 1.8 Hz, 1H), 7.27-7.22 (m, 2H), 7.06 (ddd, J = 8.2, 4.3, 2.1 Hz, 1H), 5.40 (s, 2H), 3.89-3.85 (m, 3H), 3.04 (d, J = 6.7 Hz, 2H), 1.23-1.12 (m, 1H), 0.55-0.48 (m, 2H), 0.30-0.24 (m, 2H).

TABLE 2-continued

Analytical data for examples 1-99.

| Ex. No. | R[1] | R[2] | R[3] | stereochem./ salt form | [M + H]+ observed |
|---|---|---|---|---|---|
| | | | $^1$H NMR data | | |
| 66 | cyclopropylmethyl | —Cl | 2-chlorobenzyl | achiral/ free base | 348.2 |

$^1$H NMR (500 MHz, DMSO-d6) δ 8.53 (d, J = 7.6 Hz, 1H), 7.71-7.64 (m, 1H), 7.60-7.53 (m, 1H), 7.48-7.40 (m, 2H), 7.29 (d, J = 7.6 Hz, 1H), 5.48 (s, 2H), 3.05 (d, J = 7.0 Hz, 2H), 1.26-1.13 (m, 1H), 0.56-0.48 (m, 2H), 0.32-0.25 (m, 2H).

| 67 | cyclopropylmethyl | —Cl | 3-methylbenzyl | achiral/ free base | 328.2 |

$^1$H NMR (500 MHz, DMSO-d6) δ 8.49 (d, J = 7.6 Hz, 1H), 7.37-7.13 (m, 5H), 5.40 (s, 2H), 3.03 (d, J = 7.0 Hz, 2H), 2.37-2.30 (m, 3H), 1.26-1.10 (m, 1H), 0.58-0.46 (m, 2H), 0.35-0.22 (m, 2H).

| 68 | cyclopropylmethyl | —Cl | 2-fluorobenzyl | achiral/ free base | 332.2 |

$^1$H NMR (500 MHz, DMSO-d6) δ 8.53 (d, J = 7.6 Hz, 1H), 7.62 (t, J = 7.5 Hz, 1H), 7.52-7.41 (m, 1H), 7.34-7.22 (m, 3H), 5.47 (s, 2H), 3.08-3.01 (m, 2H), 1.27-1.12 (m, 1H), 0.56-0.46 (m, 2H), 0.32-0.20 (m, 2H).

| 69 | cyclopropylmethyl | —Cl | 3,4-dichlorobenzyl | achiral/ free base | 382.1 |

$^1$H NMR (500 MHz, DMSO-d6) δ 8.51 (d, J = 7.6 Hz, 1H), 7.78 (d, J = 1.8 Hz, 1H), 7.73-7.70 (m, 1H), 7.53-7.47 (m, 1H), 7.22 (d, J = 7.6 Hz, 1H), 5.45 (s, 2H), 3.04 (d, J = 7.0 Hz, 2H), 1.22-1.14 (m, 1H), 0.55-0.48 (m, 2H), 0.30-0.25 (m, 2H).

| 70 | cyclopropylmethyl | —Cl | 4-methoxybenzyl | achiral/ free base | 344.2 |

$^1$H NMR (500 MHz, DMSO-d6) δ 8.48 (d, J = 7.6 Hz, 1H), 7.43 (d, J = 8.5 Hz, 2H), 7.26 (d, J = 7.6 Hz, 1H), 7.06-6.90 (m, 2H), 5.35 (s, 2H), 3.83-3.70 (m, 3H), 3.09-2.97 (m, 2H), 1.30-1.10 (m, 1H), 0.58-0.45 (m, 2H), 0.37-0.19 (m, 2H).

| 71 | cyclopropylmethyl | —Cl | 2,6-difluorobenzyl | achiral/ free base | 350.3 |

$^1$H NMR (500 MHz, DMSO-d6) δ 8.54 (d, J = 7.3 Hz, 1H), 7.56 (t, J = 7.0 Hz, 1H), 7.32 (d, J = 7.6 Hz, 1H), 7.20 (t, J = 7.9 Hz, 2H), 5.43 (s, 2H), 3.04 (d, J = 7.0 Hz, 2H), 1.18 (br. s., 1H), 0.51 (d, J = 6.7 Hz, 2H), 0.27 (d, J = 4.0 Hz, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 72 | cyclopropylmethyl | —Cl | 3-fluoro-2-methoxybenzyl | achiral/ free base | 362.3 |

¹H NMR (500 MHz, DMSO-d₆) δ 8.51 (d, J = 7.3 Hz, 1H), 7.51-7.41 (m, 1H), 7.32 (d, J = 7.3 Hz, 1H), 7.03-6.81 (m, 2H), 5.34 (br. s., 2H), 3.85 (s, 3H), 3.04 (d, J = 6.4 Hz, 2H), 1.19 (m, 1H), 0.51 (m, 2H), 0.27 (m, 2H).

| 73 | cyclopropylmethyl | —Cl | 5-chloro-2-(trifluoromethoxy)benzyl | achiral/ free base | 432.2 |

¹H NMR (500 MHz, DMSO-d₆) δ 8.52 (d, J = 5.8 Hz, 1H), 7.82 (br. s., 1H), 7.63 (d, J = 8.9 Hz, 1H), 7.51 (d, J = 8.5 Hz, 1H), 7.30 (d, J = 7.6 Hz, 1H), 5.43 (s, 2H), 3.04 (d, J = 4.9 Hz, 2H), 1.18 (br. s., 1H), 0.51 (d, J = 7.3 Hz, 2H), 0.27 (d, J = 2.1 Hz, 2H).

| 74 | cyclopropylmethyl | —Cl | 5-fluoro-2-methoxybenzyl | achiral/ free base | 362.3 |

¹H NMR (500 MHz, DMSO-d₆) δ 8.47 (d, J = 7.6 Hz, 1H), 7.29 (d, J = 8.9 Hz, 1H), 7.25-7.16 (m, 2H), 7.09 (dd, J = 8.9, 4.3 Hz, 1H), 5.35 (s, 2H), 3.83 (s, 3H), 3.03 (d, J = 6.7 Hz, 2H), 1.18 (br. s., 1H), 0.51 (d, J = 6.4 Hz, 2H), 0.27 (d, J = 3.7 Hz, 2H).

| 75 | cyclopropylmethyl | —Cl | 3-cyclopropoxybenzyl | achiral/ free base | 370.3 |

¹H NMR (500 MHz, DMSO-d₆) δ 8.44 (d, J = 7.3 Hz, 1H), 7.33 (t, J = 7.8 Hz, 1H), 7.26-7.20 (m, 1H), 7.17-7.13 (m, 1H), 7.08-7.01 (m, 2H), 5.41 (s, 2H), 3.81 (m, 1H), 3.01 (d, J = 6.7 Hz, 2H), 1.16 (br. s., 1H), 0.77 (d, J = 5.5 Hz, 2H), 0.63 (br. s., 2H), 0.50 (d, J = 7.0 Hz, 2H), 0.26 (d, J = 4.0 Hz, 2H).

| 76 | cyclopropylmethyl | —CF₃ | 2,6-difluorobenzyl | achiral/ free base | 384.1 |

¹H NMR (500 MHz, methanol-d₄) δ 8.97 (d, J = 7.9 Hz, 1H), 7.78 (d, J = 7.9 Hz, 1H), 7.54 (tt, J = 8.5, 6.6 Hz, 1H), 7.21-6.98 (m, 2H), 5.67 (s, 2H), 3.14 (d, J = 7.0 Hz, 2H), 1.36-1.24 (m, 1H), 0.74-0.64 (m, 2H), 0.48-0.30 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 77 | cyclopropylmethyl | —CF₃ | (4-fluorophenyl)cyclopropylmethyl | trans, racemic/ free base | 406.1 |

¹H NMR (500 MHz, methanol-d₄) δ 8.56 (d, J = 7.8 Hz, 1H), 7.21 (d, J = 7.5 Hz, 1H), 7.17-7.11 (m, 2H), 7.01-6.93 (m, 2H), 4.47 (dd, J = 10.3, 6.3 Hz, 1H), 4.29 (dd, J = 10.2, 7.3 Hz, 1H), 3.07 (d, J = 6.9 Hz, 2H), 2.10-2.04 (m, 1H), 1.62-1.50 (m, 1H), 1.30-1.18 (m, 1H), 1.16-1.07 (m, 2H), 0.66-0.59 (m, 2H), 0.39-0.32 (m, 2H).

| 78 | cyclopropylmethyl | —CF₃ | (4-fluorophenyl)cyclopropylmethyl | trans, enantiomer A/ free base | 406.1 |

¹H NMR (500 MHz, methanol-d₄) δ 8.56 (d, J = 7.8 Hz, 1H), 7.21 (d, J = 7.6 Hz, 1H), 7.18-7.11 (m, 2H), 7.01-6.94 (m, 2H), 4.47 (dd, J = 10.3, 6.3 Hz, 1H), 4.30 (dd, J = 10.2, 7.3 Hz, 1H), 3.08 (d, J = 6.9 Hz, 2H), 2.10-2.05 (m, 1H), 1.61-1.53 (m, 1H), 1.28-1.21 (m, 1H), 1.16-1.09 (m, 2H), 0.66-0.61 (m, 2H), 0.39-0.32 (m, 2H).

| 79 | cyclopropylmethyl | —CF₃ | (4-fluorophenyl)cyclopropylmethyl | trans, enantiomer B/ free base | 406.1 |

¹H NMR data was identical to example 79.

| 80 | cyclopropylmethyl | —CF₃ | 2,6-dichlorophenethyl | achiral/ free base | 414.1 |

¹H NMR (400 MHz, methanol-d₄) δ 8.54 (d, J = 7.8 Hz, 1H), 7.31-7.24 (m, 2H), 7.19 (d, J = 7.8 Hz, 1H), 7.14-7.00 (m, 1H), 4.57 (t, J = 6.7 Hz, 2H), 3.38 (td, J = 6.8, 1.8 Hz, 2H), 3.06 (d, J = 7.0 Hz, 2H), 1.23 (s, 1H), 0.68-0.54 (m, 2H), 0.41-0.28 (m, 2H).

| 81 | cyclopropylmethyl | —CF₃ | 2,6-difluorophenethyl | achiral/ free base | 398.2 |

¹H NMR (500 MHz, methanol-d₄) δ 8.55 (d, J = 7.8 Hz, 1H), 7.37-7.27 (m, 1H), 7.19 (d, J = 7.8 Hz, 1H), 6.97 (t, J = 8.0 Hz, 2H), 4.56 (t, J = 6.6 Hz, 2H), 3.26 (t, J = 6.5 Hz, 2H), 3.07 (d, J = 6.9 Hz, 2H), 1.24 (s, 1H), 0.68-0.56 (m, 2H), 0.41-0.29 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 82 | cyclopropylmethyl | —CF₃ | 2,6-dichloropyrimidin-4-ylmethyl | achiral/ free base | 418.0 |

¹H NMR (500 MHz, methanol-d₄) δ 8.77-8.69 (m, 1H), 7.49 (s, 1H), 7.17-7.11 (m, 1H), 4.73 (s, 2H), 3.16 (d, J = 6.9 Hz, 2H), 1.38-1.27 (m, 1H), 0.73-0.63 (m, 2H), 0.48-0.36 (m, 2H).

| 83 | cyclopropylmethyl | —CF₃ | 2,2-difluoro-2-phenylethyl | achiral/ free base | 398.2 |

¹H NMR (500 MHz, methanol-d₄) δ 8.56 (d, J = 7.8 Hz, 1H), 7.65 (dd, J = 7.6, 1.8 Hz, 2H), 7.56-7.47 (m, 3H), 7.19 (d, J = 7.8 Hz, 1H), 3.08 (d, J = 6.9 Hz, 2H), 1.29-1.17 (m, 1H), 0.63 (dd, J = 8.1, 1.4 Hz, 2H), 0.42-0.31 (m, 2H).

| 84 | cyclopropylmethyl | —CF₃ | 2-fluoro-2-phenylethyl | racemate/ free base | 380.0 |

¹H NMR (500 MHz, methanol-d₄) δ 8.57-8.53 (m, 1H), 7.53-7.37 (m, 5H), 7.20 (d, J = 7.8 Hz, 1H), 5.96-5.82 (m, 1H), 4.77-4.56 (m, 2H), 3.07 (d, J = 7.0 Hz, 2H), 1.28-1.19 (m, 1H), 0.66-0.59 (m, 2H), 0.38-0.31 (m, 2H).

| 85 | cyclopropylmethyl | —CF₃ | phenethyl | racemate/ free base | 348.2 |

¹H NMR (500 MHz, chloroform-d) δ 8.04 (d, J = 7.6 Hz, 1H), 7.53-7.31 (m, 5H), 6.82 (d, J = 7.8 Hz, 1H), 5.35 (s, 2H), 3.04 (d, J = 6.6 Hz, 2H), 1.20-1.08 (m, 1H), 0.70-0.54 (m, 2H), 0.32 (q, J = 4.9 Hz, 2H).

| 86 | (2,2-difluorocyclopropyl)methyl | —CF₃ | trans-4-(4-fluorophenyl)-4-methoxycyclohexylmethyl | racemate/ free base | 486.2 |

¹H NMR (500 MHz, methanol-d₄) δ 8.58 (d, J = 7.8 Hz, 1H), 7.52-7.43 (m, 2H), 7.33 (d, J = 7.8 Hz, 1H), 7.15-7.04 (m, 2H), 4.78 (dt, J = 14.7, 7.4 Hz, 1H), 3.40-3.32 (m, 1H), 3.00 (s, 3H), 2.39 (dtd, J = 12.8, 7.8, 5.2 Hz, 1H), 2.28 (tdd, J = 11.7, 8.0, 5.7 Hz, 1H), 2.23-2.16 (m, 2H), 2.03 (td, J = 9.3, 3.3 Hz, 4H), 1.99-1.89 (m, 2H).

TABLE 2-continued

Analytical data for examples 1-99.

| Ex. No. | R¹ | R² | R³ | stereochem./ salt form | [M + H]⁺ observed |
|---|---|---|---|---|---|
| 87 | (difluorocyclopropyl) | —CF₃ | (4-fluorophenyl-methoxy-cyclohexyl, MeO) | enantiomer A/ TFA salt | 486.2 |

¹H NMR (500 MHz, methanol-d₄) δ 8.82 (d, J = 7.8 Hz, 1H), 7.57 (d, J = 7.8 Hz, 1H), 7.54-7.44 (m, 2H), 7.16-7.05 (m, 2H), 4.91 (dt, J = 14.8, 7.4 Hz, 1H), 3.46 (ddd, J = 11.4, 9.6, 7.8 Hz, 1H), 3.02 (s, 3H), 2.47-2.31 (m, 2H), 2.24 (d, J = 13.4 Hz, 2H), 2.11-2.02 (m, 4H), 2.02-1.91 (m, 2H)

| 88 | (difluorocyclopropyl) | —CF₃ | (4-fluorophenyl-methoxy-cyclohexyl, MeO) | enantiomer B/ free base | 486.2 |

¹H NMR data was identical to example 87.

| 89 | (monofluorocyclopropyl) | —CF₃ | (4-fluorophenyl-methoxy-cyclohexyl, MeO) | racemate/ free base | 468.3 |

¹H NMR (500 MHz, chloroform-d) δ 8.18 (d, J = 7.6 Hz, 1H), 7.45-7.32 (m, 2H), 7.06 (t, J = 8.6 Hz, 2H), 6.88 (d, J = 7.6 Hz, 1H), 4.97 (ddt, J = 63.2, 5.3, 2.8 Hz, 1H), 4.53-4.41 (m, 1H), 2.99 (s, 3H), 2.57-2.44 (m, 1H), 2.28-2.18 (m, 2H), 2.18-2.06 (m, 2H), 2.06-1.96 (m, 2H), 1.88-1.69 (m, 4H).

| 90 | (monofluorocyclopropyl) | —CF₃ | (4-fluorophenyl-methoxy-cyclohexyl, MeO) | enantiomer A/ TFA salt | 468.3 |

¹H NMR (500 MHz, chloroform-d) δ 8.19 (d, J = 7.5 Hz, 1H), 7.39 (dd, J = 8.1, 5.5 Hz, 2H), 7.06 (t, J = 8.5 Hz, 2H), 6.89 (d, J = 7.6 Hz, 1H), 4.97 (d, J = 63.3 Hz, 1H), 4.54-4.40 (m, 1H), 2.99 (s, 3H), 2.60-2.45 (m, 1H), 2.23 (d, J = 12.7 Hz, 2H), 2.18-2.06 (m, 2H), 2.06-1.97 (m, 2H), 1.84-1.68 (m, 4H).

| 91 | (monofluorocyclopropyl) | —CF₃ | (4-fluorophenyl-methoxy-cyclohexyl, MeO) | enantiomer B/ free base | 468.3 |

¹H NMR (500 MHz, chloroform-d) δ 8.19 (d, J = 6.9 Hz, 1H), 7.39 (br. s., 2H), 7.13-7.00 (m, 2H), 6.89 (d, J = 7.0 Hz, 1H), 4.97 (d, J = 63.8 Hz, 1H), 4.48 (br. s., 1H), 2.99 (br. s., 3H), 2.51 (br. s., 1H), 2.22 (d, J = 12.8 Hz, 2H), 2.12 (d, J = 11.1 Hz, 2H), 2.02 (br. s., 2H), 1.90-1.66 (m, 4H).

TABLE 2-continued

Analytical data for examples 1-99.

| Ex. No. | R¹ | R² | R³ | stereochem./ salt form | [M + H]⁺ observed |
|---|---|---|---|---|---|
| | | | ¹H NMR data | | |
| 92 | cyclopropyl | —CF₃ | 1-(4-fluorophenyl)-4-methoxycyclohexyl | achiral/ free base | 450.2 |

¹H NMR (600 MHz, DMSO-d₆) δ 8.74 (d, J = 5.1 Hz, 1H), 7.43 (dd, J = 8.1, 5.5 Hz, 2H), 7.29 (d, J = 7.7 Hz, 1H), 7.20 (t, J = 8.6 Hz, 2H), 4.83 (br. s., 1H), 2.89 (s, 3H), 2.40-2.32 (m, 1H), 2.07 (d, J = 12.5 Hz, 2H), 1.97-1.77 (m, 6H), 1.15-1.05 (m, 2H), 1.00 (br. s., 2H)

| 93 | 3,3-difluorocyclobutyl | —CF₃ | 1-(4-fluorophenyl)-4-methoxycyclohexyl | achiral/ free base | 500.3 |

¹H NMR (500 MHz, DMSO-d₆) δ 8.59 (d, J = 8.1 Hz, 1H), 7.43 (dd, J = 8.6, 5.7 Hz, 2H), 7.29 (d, J = 8.1 Hz, 1H), 7.20 (t, J = 8.8 Hz, 2H), 4.92-4.77 (m, 1H), 4.01-3.85 (m, 1H), 3.27-3.14 (m, 2H), 3.14-2.99 (m, 2H), 2.89 (s, 3H), 2.07 (d, J = 11.7 Hz, 2H), 1.96-1.75 (m, 6H)

| 94 | 2,2-dimethylcyclopropyl | —CF₃ | 1-(4-fluorophenyl)-4-methoxycyclohexyl | racemate/ free base | 478.3 |

¹H NMR (500 MHz, DMSO-d₆) δ 8.61 (d, J = 8.1 Hz, 1H), 7.44 (dd, J = 8.1, 5.9 Hz, 2H), 7.26 (d, J = 8.1 Hz, 1H), 7.20 (t, J = 8.6 Hz, 2H), 4.83 (br. s., 1H), 2.89 (s, 3H), 2.20 (dd, J = 8.8, 5.5 Hz, 1H), 2.07 (br. s., 2H), 1.93 (d, J = 6.2 Hz, 2H), 1.90-1.75 (m, 4H), 1.31 (s, 3H), 1.28 (t, J = 4.8 Hz, 1H), 1.11 (dd, J = 8.6, 4.2 Hz, 1H), 0.79 (s, 3H)

| 95 | cyclopropylmethyl | —CF₃ | 1-(4-fluorophenyl)-4-hydroxycyclohexyl | achiral (1s,4s)/ free base | 450.2 |

¹H NMR (500 MHz, methanol-d₄) δ 8.90 (d, J = 7.8 Hz, 1H), 7.72 (d, J = 7.9 Hz, 1H), 7.60-7.51 (m, 2H), 7.11-7.01 (m, 2H), 5.10-4.97 (m, 1H), 3.13 (d, J = 6.9 Hz, 2H), 2.27-2.03 (m, 6H), 1.93 (d, J = 14.2 Hz, 2H), 1.38-1.26 (m, 1H), 0.75-0.65 (m, 2H), 0.46-0.37 (m, 2H)

TABLE 2-continued

Analytical data for examples 1-99.

| Ex. No. | R¹ | R² | R³ | stereochem./ salt form | [M + H]⁺ observed |
|---|---|---|---|---|---|
| 96 | cyclopropylmethyl | —CF₃ | 3-(4-fluorophenyl)cyclobutyl | achiral (1r,3r)/ free base | 406.3 |

¹H NMR (500 MHz, chloroform-d) δ 8.09 (d, J = 7.6 Hz, 1H), 7.26-7.20 (m, 2H), 7.08-7.00 (m, 2H), 6.72 (d, J = 7.8 Hz, 1H), 4.87 (quin, J = 7.2 Hz, 1H), 3.27-3.17 (m, 1H), 3.09 (d, J = 6.7 Hz, 2H), 3.04-2.94 (m, 2H), 2.48-2.37 (m, 2H), 1.23-1.12 (m, 1H), 0.68-0.61 (m, 2H), 0.37-0.32 (m, 2H)

| 97 | 2,2,2-trifluoroethyl | —CF₃ | 4-(4-fluorophenyl)-4-methoxycyclohexyl | achiral/ free base | 492.3 |

¹H NMR (500 MHz, chloroform-d) δ 8.12 (d, J = 7.3 Hz, 1H), 7.40 (dd, J = 8.2, 5.4 Hz, 2H), 7.08 (t, J = 8.5 Hz, 2H), 6.93 (d, J = 7.3 Hz, 1H), 4.50 (t, J = 10.0 Hz, 1H), 4.07 (q, J = 9.6 Hz, 2H), 3.01 (s, 3H), 2.24 (d, J = 12.7 Hz, 2H), 2.21-2.08 (m, 2H), 2.08-1.97 (m, 2H), 1.89-1.73 (m, 2H)

| 98 | (2,2-difluorocyclopropyl)methyl | —CF₃ | 3-(4-fluorophenyl)cyclobutyl | racemate (1r,3r)/free base | 428.2 |

¹H NMR (500 MHz, chloroform-d) δ 8.17 (d, J = 7.6 Hz, 1H), 7.26-7.20 (m, 2H), 7.08-7.01 (m, 2H), 6.82 (d, J = 7.8 Hz, 1H), 4.90 (quin, J = 7.1 Hz, 1H), 3.28-3.18 (m, 1H), 3.05-2.96 (m, 2H), 2.94-2.85 (m, 1H), 2.59-2.50 (m, 1H), 2.42 (tdd, J = 9.9, 7.5, 2.8 Hz, 2H), 2.22 (tdd, J = 11.6, 8.2, 5.3 Hz, 1H)

| 99 | cyclopropylmethyl | —CF₃ | 4-(4-fluorophenyl)-4-(trideuteromethoxy)cyclohexyl | achiral (1s,4s)/ free base | 467.3 |

¹H NMR (500 MHz, menthanol-d₄) δ 8.57 (d, J = 7.8 Hz, 1H), 7.55-7.43 (m, 2H), 7.30 (d, J = 7.8 Hz, 1H), 7.16-7.06 (m, 2H), 4.79 (quin, J = 7.3 Hz, 1H), 3.09 (d, J = 6.9 Hz, 2H), 2.28-2.15 (m, 2H), 2.09-1.98 (m, 4H), 1.98-1.88 (m, 2H), 1.29-1.21 (m, 1H), 0.69-0.59 (m, 2H), 0.39-0.33 (m, 2H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

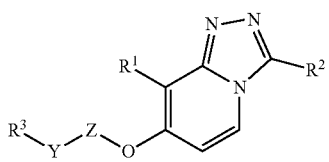

where $R^1$ is haloalkyl; $R^1$ is halocycloalkyl or (cycloalkyl)alkyl; $R^3$ is $Ar^1$ or $OAr^1$; $Ar^1$ is phenyl, pyridinyl, or pyrimidinyl, and is substituted with 0-3 substituents selected from cyano, halo, alkyl, haloalkyl, cycloalkyl, alkoxy, cycloalkoxy, and haloalkoxy; Y is a bond or $C_{3-6}$ cycloalkyl substituted with 0-3 substituents selected from cyano, halo, alkyl, haloalkyl, hydroxy, alkoxy, and haloalkoxy; and Z is a bond or $C_{1-3}$ alkyl substituted with 0-3 substituents selected from cyano, halo, alkyl, haloalkyl, hydroxy, alkoxy, and haloalkoxy; or a pharmaceutically acceptable salt thereof.

2. A compound of claim 1 where —Y—Z— is 1,4-cyclohexanediyl, 1,3-cyclobutanediyl, or (cyclopropyl)methyl, and is substituted with 1 substituents selected from cyano, halo, alkyl, haloalkyl, hydroxy, alkoxy, and haloalkoxy.

3. A compound of claim 2 where $R^3$ is $Ar^1$.

4. A compound of claim 1 where $Ar^1$ is phenyl substituted with 0-3 substituents selected from cyano, halo, alkyl, haloalkyl, cycloalkyl, alkoxy, cycloalkoxy, and haloalkoxy.

5. A compound of claim 1 where Y is $C_{3-6}$ cycloalkyl substituted with 0-3 substituents selected from cyano, halo, alkyl, haloalkyl, hydroxy, alkoxy, and haloalkoxy.

6. A compound of claim 1 where Y is a bond and Z is $C_{1-3}$ alkyl substituted with 0-3 substituents selected from cyano, halo, alkyl, haloalkyl, hydroxy, alkoxy, and haloalkoxy.

7. A compound of claim 1 where —Y—Z— is 1,4-cyclohexanediyl, 1,3-cyclobutanediyl, or (cyclopropyl)methyl, and is substituted with 1 substituents selected from cyano, halo, alkyl, haloalkyl, hydroxy, alkoxy, and haloalkoxy.

8. A compound of claim 1 selected from the group consisting of 3-(cyclopropylmethyl)-7-(((1S,2S)-2-(2-fluoro-6-methoxyphenyl)cyclopropyl)methoxy)-8-(trifluoromethyl)[1,2,4]triazolo[4,3-a]pyridine;

3-(cyclopropylmethyl)-7-(((1R,2R)-2-(2-fluoro-6-methoxyphenyl)cyclopropyl)methoxy)-8-(trifluoromethyl)-[1,2,4]triazolo[4,3-a]pyridine;

3-(cyclopropylmethyl)-7-((1s,4s)-4-(4-fluorophenyl)-4-methoxycyclohexyloxy)-8-(trifluoromethyl)-[1,2,4]triazolo[4,3-a]pyridine;

(1s,3s)-3-(3-(cyclopropylmethyl)-8-(trifluoromethyl)-[1,2,4]triazolo[4,3-a]pyridin-7-yloxy)-1-(2-methoxyphenyl)cyclobutanecarbonitrile;

(±)-3-(cyclopropylmethyl)-7-(((1S,2S)-2-(4-fluoro-2-methoxyphenyl)cyclopropyl)methoxy)-8-(trifluoromethyl)-[1,2,4]triazolo[4,3-a]pyridine;

3-(cyclopropylmethyl)-7-(2,6-difluorophenethoxy)-8-(trifluoromethyl)-[1,2,4]triazolo[4,3-a]pyridine;

3-(cyclopropylmethyl)-7-((1r,4r)-4-phenylcyclohexyloxy)-8-(trifluoromethyl)-[1,2,4]triazolo[4,3-a]pyridine;

3-(cyclopropylmethyl)-7-((1r,3r)-3-phenylcyclobutoxy)-8-(trifluoromethyl)-[1,2,4]triazolo[4,3-a]pyridine;

(±)-7-(((1S,2S)-2-(2-chloro-6-fluorophenyl)cyclopropyl)methoxy)-3-(cyclopropylmethyl)-8-(trifluoromethyl)-[1,2,4]triazolo[4,3-a]pyridine;

(1s,3s)-3-(3-(cyclopropylmethyl)-8-(trifluoromethyl)-[1,2,4]triazolo[4,3-a]pyridin-7-yloxy)-1-(3-fluorophenyl)cyclobutanecarbonitrile;

3-(cyclopropylmethyl)-7-(((1S,2S)-2-(2-methoxyphenyl)cyclopropyl)methoxy)-8-(trifluoromethyl)-[1,2,4]triazolo[4,3-a]pyridine;

3-(cyclopropylmethyl)-7-((1s,4s)-4-(3,4-difluorophenyl)-4-methoxycyclohexyloxy)-8-(trifluoromethyl)-[1,2,4]triazolo[4,3-a]pyridine;

(±)-3-(cyclopropylmethyl)-7-(((1S,2S)-2-(3,6-difluoro-2-methoxyphenyl)cyclopropyl)methoxy)-8-(trifluoromethyl)-[1,2,4]triazolo[4,3-a]pyridine;

(R)-7-(2-(2-chloro-6-fluorophenyl)propoxy)-3-(cyclopropylmethyl)-8-(trifluoromethyl)-[1,2,4]triazolo[4,3-a]pyridine;

(1s,4s)-4-(3-(cyclopropylmethyl)-8-(trifluoromethyl)-[1,2,4]triazolo[4,3-a]pyridin-7-yloxy)-1-(3,4-difluorophenyl)cyclohexanol;

(S)-7-(2-(2-chloro-6-fluorophenyl)propoxy)-3-(cyclopropylmethyl)-8-(trifluoromethyl)-[1,2,4]triazolo[4,3-a]pyridine;

7-(2-chloro-6-fluorophenethoxy)-3-(cyclopropylmethyl)-8-(trifluoromethyl)-[1,2,4]triazolo[4,3-a]pyridine;

3-(cyclopropylmethyl)-7-(((1R,2R)-2-(4-fluorophenyl)cyclopropyl)methoxy)-8-(trifluoromethyl)-[1,2,4]triazolo[4,3-a]pyridine;

(±)-3-(cyclopropylmethyl)-7-(((1S,2S)-2-(4-methoxyphenyl)cyclopropyl)methoxy)-8-(trifluoromethyl)-[1,2,4]triazolo[4,3-a]pyridine;

3-(cyclopropylmethyl)-7-(((1R,2R)-2-(2-methoxyphenyl)cyclopropyl)methoxy)-8-(trifluoromethyl)-[1,2,4]triazolo[4,3-a]pyridine;

(1s,4s)-4-(3-(cyclopropylmethyl)-8-(trifluoromethyl)-[1,2,4]triazolo[4,3-a]pyridin-7-yloxy)-1-(4-fluorophenyl)cyclohexanecarbonitrile;

(±)-3-(cyclopropylmethyl)-7-(((1S,2S)-2-(2-fluorophenyl)cyclopropyl)methoxy)-8-(trifluoromethyl)-[1,2,4]triazolo[4,3-a]pyridine;

3-(cyclopropylmethyl)-7-(2,6-difluorophenethoxy)-8-(trifluoromethyl)-[1,2,4]triazolo[4,3-a]pyridine;

7-(((1S,2S)-2-(4-chlorophenyl)cyclopropyl)methoxy)-3-(cyclopropylmethyl)-8-(trifluoromethyl)-[1,2,4]triazolo[4,3-a]pyridine;

3-(cyclopropylmethyl)-7-((1-phenylcyclohexyl)methoxy)-8-(trifluoromethyl)-[1,2,4]triazolo[4,3-a]pyridine;

3-(cyclopropylmethyl)-7-(((1R,2R)-2-(2-(trifluoromethoxy)phenyl)cyclopropyl)methoxy)-8-(trifluoromethyl)-[1,2,4]triazolo[4,3-a]pyridine;

(±)-3-(cyclopropylmethyl)-7-(((1S,2S)-2-(2,5-difluorophenyl)cyclopropyl)methoxy)-8-(trifluoromethyl)-[1,2,4]triazolo[4,3-a]pyridine;

3-(cyclopropylmethyl)-7-(((1S,2S)-2-(2-(trifluoromethoxy)phenyl)cyclopropyl)methoxy)-8-(trifluoromethyl)-[1,2,4]triazolo[4,3-a]pyridine;

(1s,3s)-3-(3-(cyclopropylmethyl)-8-(trifluoromethyl)-[1,2,4]triazolo[4,3-a]pyridin-7-yloxy)-1-(3,5-difluorophenyl)cyclobutanecarbonitrile;

3-(cyclopropylmethyl)-7-(((1S,2S)-2-(2-fluorophenyl)cyclopropyl)methoxy)-8-(trifluoromethyl)-[1,2,4]triazolo[4,3-a]pyridine;

(1s,3s)-3-(3-(cyclopropylmethyl)-8-(trifluoromethyl)-[1,2,4]triazolo[4,3-a]pyridin-7-yloxy)-1-(4-fluorophenyl)cyclobutanecarbonitrile;

7-(((1R,2R)-2-(4-Chlorophenyl)cyclopropyl)methoxy)-3-(cyclopropylmethyl)-8-(trifluoromethyl)-[1,2,4]triazolo[4,3-a]pyridine;

7-(2-(4-chlorophenyl)-2-methylpropoxy)-3-(cyclopropylmethyl)-8-(trifluoromethyl)-[1,2,4]triazolo[4,3-a]pyridine;

3-(2,2-difluorocyclopropyl)-7-((1s,4s)-4-(4-fluorophenyl)-4-methoxycyclohexyloxy)-8-(trifluoromethyl)-[1,2,4]triazolo[4,3-a]pyridine;

3-(cyclopropylmethyl)-7-(2-fluoro-2-phenylethoxy)-8-(trifluoromethyl)-[1,2,4]triazolo[4,3-a]pyridine;

3-(cyclopropylmethyl)-7-((1r,3r)-3-(4-fluorophenyl)cyclobutoxy)-8-(trifluoromethyl)-[1,2,4]triazolo[4,3-a]pyridine; and (1s,4s)-4-(3-(cyclopropylmethyl)-8-(trifluoromethyl)-[1,2,4]triazolo[4,3-a]pyridin-7-yloxy)-1-(4-fluorophenyl)cyclohexanol;

or a pharmaceutically acceptable salt thereof.

9. A compound of claim 1 selected from (1s,3s)-3-(3-(cyclopropylmethyl)-8-(trifluoromethyl)-[1,2,4]triazolo[4,3-a]pyridin-7-yloxy)-1-(3,5-(di-$^3$H)-2-methoxyphenyl)cyclobutanecarbonitrile and 3-(cyclopropylmethyl)-7-((1s,4s)-4-(4-fluorophenyl)-4-(methoxy-d$_3$)cyclohexyloxy)-8-(trifluoromethyl)-[1,2,4]triazolo[4,3-a]pyridine;

or a pharmaceutically acceptable salt thereof.

10. A composition comprising a compound of claim 1, or a pharmaceutically acceptable salt thereof, and a pharmaceutically acceptable carrier.

11. A method for the treatment of anxiety or schizophrenia, which comprises administering to a patient a therapeutically affective amount of a compound of claim 1.

* * * * *

UNITED STATES PATENT AND TRADEMARK OFFICE
CERTIFICATE OF CORRECTION

PATENT NO. : 9,738,642 B2
APPLICATION NO. : 15/022072
DATED : August 22, 2017
INVENTOR(S) : Marcin et al.

Page 1 of 1

It is certified that error appears in the above-identified patent and that said Letters Patent is hereby corrected as shown below:

On the Title Page

(54) Title
Delete "PYSCHIATRIC" and insert -- PSYCHIATRIC --.

In the Specification

Column 1, Line 3, delete "PYSCHIATRIC" and insert -- PSYCHIATRIC --.

In the Claims

Claim 1, Column 131, Line 23 delete "$R^1$" and insert -- $R^2$ --.

Claim 8, Column 131, Line 58 delete ")[1,2,4]" and insert -- )-[1,2,4] --.

Signed and Sealed this
Sixteenth Day of October, 2018

Andrei Iancu
*Director of the United States Patent and Trademark Office*